United States Patent [19]

Mann et al.

[11] Patent Number: 6,165,469
[45] Date of Patent: Dec. 26, 2000

[54] **RECOMBINANT *ENTAMOEBA HISTOLYTICA* LECTIN SUBUNIT PEPTIDES AND REAGENTS SPECIFIC FOR MEMBERS OF THE 170 KD SUBUNIT MULTIGENE FAMILY**

[75] Inventors: Barbara J. Mann; William A. Petri, both of Charlottesville, Va.

[73] Assignee: University of Virginia, Charlottesville, Va.

[21] Appl. No.: 08/569,214

[22] PCT Filed: Jun. 17, 1994

[86] PCT No.: PCT/US94/06890

§ 371 Date: Apr. 29, 1996

§ 102(e) Date: Apr. 29, 1996

[87] PCT Pub. No.: WO95/00849

PCT Pub. Date: Jan. 5, 1995

Related U.S. Application Data

[63] Continuation of application No. 08/078,476, Jun. 17, 1993, abandoned, and a continuation-in-part of application No. 08/130,735, Oct. 1, 1993, abandoned, said application No. 08/078,476, is a continuation-in-part of application No. 07/615,719, Nov. 21, 1990, Pat. No. 5,260,429, and application No. 08/075,226, Jun. 10, 1993, Pat. No. 5,401,831, said application No. 08/075,226, is a division of application No. 07/479,691, Feb. 13, 1990, Pat. No. 5,272,058, said application No. 07/615,719, is a continuation-in-part of application No. 07/479,691, which is a continuation-in-part of application No. 07/456,579, Dec. 29, 1989, Pat. No. 5,004,608, which is a continuation of application No. 07/143,626, Jan. 13, 1988, abandoned.

[51] Int. Cl.$^7$ ................................................ A61K 39/002
[52] U.S. Cl. ...................................... 424/185.1; 424/269.1
[58] Field of Search .............................. 424/185.1, 269.1

[56] References Cited

U.S. PATENT DOCUMENTS 5,004,608 4/1991 Ravdin et al. .
5,260,429 11/1993 Petri et al. .
5,272,058 12/1993 Petri, Jr. et al. .

FOREIGN PATENT DOCUMENTS

WO 91/12529 8/1991 WIPO .

OTHER PUBLICATIONS

Petri, W.A. et al., *J. Biol. Chem.* (1989), vol. 264, pp. 3007–3012.
Petri, W.A. Jr., et al., *Am. Journal Med. Sci.* (1989), vol. 296, pp. 163–165.
Petri et al., *Infect. Immun.* (1987), vol. 55, pp. 2327–2331.
Petri et al., *J. Immunol.* (1990), vol. 144, pp. 4803–4809.
Schain et al., *Infect. Immun.* (1992), vol. 60, pp. 2143–2146.
Mann, B. et al., *Proc. Natl. Acad. Sci. USA* (1991), vol. 88, pp. 3248–3252.
Tannich, et al. *Proc. Natl. Acad. Sci. USA* (1991), vol. 88, pp. 1849–1853.
Mann, B. et al., *Parasit Today* (1991), vol. 7, pp. 173–176.
Mann, B.J. et al., *Infect. Immun.* (1993), vol. 61, pp. 1772–1778.
Root, et al., *Arch. Invest. Med.* (*Mex*) (1978), vol. 9: Supplement 1:203.
Palacios et al., *Arch. Invest. Med.* (*Mex*) (1978), vol. 9: Supplement 1:203.
Randall et al., *Trans. Roy Soc. Trop. Med. Hygiene* (1984), vol. 78, pp. 593–595.
Grundy, *Trans. Roy. Soc. Trop. Med. Hygiene* (1982), vol. 76, p. 396.
Ungar, *Am. Journal Trop. Med. Hygiene* (1985), vol. 34, pp. 465–472.
Amebiasis: Human Infection by *Entamoeba Histolytica*, J. Ravdin, ed. (1988) Wiley Medical Publishing, pp. 635–649.
Krupp, I.M., *Am. J. Trop. Med. Hygiene*, (1970), vol. 19, pp. 57–62.
Lobel, H.O. et al., *Ann. Rev. Microbiol.* (1978), vol. 32, pp. 327–347.
Ravdin, J.I. et al., *J. Infectious Diseases* (1990), vol. 162, pp. 768–772.
Stanley, Jr. S.L. et al., *Proc. Natl. Acad. Sci. USA* (1990), vol. 87, pp. 4976–4980.
Stanley, Jr. S.L. et al., *JAMA* (1991), vol. 266, pp. 1984–1986.
Zhang, Y. et al., *J. Clin. Micro–Immunol.* (1992), vol. 30, No. 11, pp. 2788–2792.
Plotkin et al., *Vaccines* (1988) W.B. Saunders Company, pp. 568–575.
Purdy et al., *Molecular and Biochemical Parasitol.*, (1993), vol. 62, No. 1, pp. 53–60.
Chung et al., (1992) Abstract, 1992 Meeting of the American Federation of Clinical Researchers (AFCR).

*Primary Examiner*—Anthony C. Caputa
*Assistant Examiner*—Stephen Gucker
*Attorney, Agent, or Firm*—Shmuel Livnat; Rader, Fishman & Grauer PLLC

[57] ABSTRACT

The adhesin 170 kDa subunit of Hm-1:IMSS strain of *Entamoeba histolytica* is encoded by a gene family that includes hgl1, hgl2 and a previously undescribed third gene, hgl3, for which the DNA and protein sequences are disclosed. All three of these heavy subunit genes were expressed in the amebae. Methods and reagents (both nucleic acid and immunological) which are specific for each of the genes, as well as reagents which detect common regions of all three hgl genes or their nucleic acid or protein products, are disclosed. Recombinantly produced heavy chain subunit of *E. Histolytica* Gal/GalNAc adherence lectin or an epitope-bearing portion thereof may be used as antigen in serological analysis for *E. histolytica* infection or as an immunogen for protection against infection. Recombinant production in procaryotic systems provides antigens or immunogens which are immunologically reactive.

19 Claims, 18 Drawing Sheets

```
  1 ATG AAA TTA TTA TTA TTA AAT ATC TTA TTA TTA TGT TGT CTT   42
    M   K   L   L   L   L   N   I   L   L   L   C   C   L

43 GCA GAT AAA CTT GAT GAA TTT TCA GCA GAT AAT GAC TAT TAT   84
    A   D   K   L   D   E   F   S   A   D   N   D   Y   Y

85 GAC GGT GGT ATT ATG TCT CGT GGA AAG AAT GCA GGT TCA TGG  126
    D   G   G   I   M   S   R   G   K   N   A   G   S   W

127 TAT CAT TCT TAC ACT CAC CAA TAT GAT GTT TTC TAT TAT TTA  168
    Y   H   S   Y   T   H   Q   Y   D   V   F   Y   Y   L

169 GCT ATG CAA CCA TGG AGA CAT TTT GTA TGG ACT ACA TGC GAT  210
    A   M   Q   P   W   R   H   F   V   W   T   T   C   D

211 AAA AAT GAT AAT ACA GAA TGT TAT AAA TAT ACT ATC AAT GAA  252
    K   N   D   N   T   E   C   Y   K   Y   T   I   N   E

253 GAT CAT AAT GTA AAG GTT GAA GAT ATT AAT AAA ACA AAT ATT  294
    D   H   N   V   K   V   E   D   I   N   K   T   N   I

295 AAA CAA GAT TTT TGT CAA AAA GAA TAT GCA TAT CCA ATT GAA  336
    K   Q   D   F   C   Q   K   E   Y   A   Y   P   I   E

337 AAA TAT GAA GTT GAT TGG GAC AAT GTT CCA GTT GAT GAA CAA  378
    K   Y   E   V   D   W   D   N   V   P   V   D   E   Q

379 CGA ATT GAA AGT GTA GAT ATT AAT GGA AAA ACT TGT TTT AAA  420
    R   I   E   S   V   D   I   N   G   K   T   C   F   K

421 TAT GCA GCT AAA AGA CCA TTG GCT TAT GTT TAT TTA AAT ACA  462
    Y   A   A   K   R   P   L   A   Y   V   Y   L   N   T

463 AAA ATG ACA TAT GCA ACA AAA ACT GAA GCA TAT GAT GTT TGT  504
    K   M   T   Y   A   T   K   T   E   A   Y   D   V   C

505 AGA ATG GAT TTC ATT GGA GGA AGA TCA ATT ACA TTC AGA TCA  546
    R   M   D   F   I   G   G   R   S   I   T   F   R   S

547 TTT AAC ACA GAG AAT AAA GCA TTT ATT GAT CAA TAT AAT ACA  588
    F   N   T   E   N   K   A   F   I   D   Q   Y   N   T

589 AAC ACT ACA TCA AAA TGT CTT CTT AAT GTA TAT GAT AAT AAT  630
    N   T   T   S   K   C   L   L   N   V   Y   D   N   N

631 GTT AAT ACA CAT CTT GCA ATT ATC TTT GGT ATT ACT GAT TCT  672
    V   N   T   H   L   A   I   I   F   G   I   T   D   S

673 ACA GTC ATT AAA TCA CTT CAA GAG AAT TTA TCT CTT TTA AGT  714
    T   V   I   K   S   L   Q   E   N   L   S   L   L   S

715 CAA CTA AAA ACA GTC AAA GGA GTA ACA CTC TAC TAT CTT AAA  756
    Q   L   K   T   V   K   G   V   T   L   Y   Y   L   K

757 GAT GAT ACT TAT TTT ACA GTT AAT ATT ACT TTA GAT CAA TTA  798
```

FIG. IA

```
          D   D   T   Y   F   T   V   N   I   T   L   D   Q   L
     799 AAA TAT GAT ACA CTT GTC AAA TAC ACA GCA GGA ACA GGA CAA  840
          K   Y   D   T   L   V   K   Y   T   A   G   T   G   Q

841 GTT GAT CCA CTT ATT AAT ATT GCT AAG AAT GAT TTA GCT ACT  882
          V   D   P   L   I   N   I   A   K   N   D   L   A   T

883 AAA GTT GCA GAT AAA AGT AAA GAT AAA AAT GCA AAT GAT AAA  924
          K   V   A   D   K   S   K   D   K   N   A   N   D   K

925 ATC AAA AGA GGA ACT ATG ATT GTG TTA ATG GAT ACT GCA CTT  966
          I   K   R   G   T   M   I   V   L   M   D   T   A   L

967 GGA TCA GAA TTT AAT GCA GAA ACA GAA TTT GAT AGA AAG AAT 1008
          G   S   E   F   N   A   E   T   E   F   D   R   K   N

1009 ATT TCA GTT CAT ACT GTT GTT CTT AAT AGA AAT AAA GAC CCA 1050
          I   S   V   H   T   V   V   L   N   R   N   K   D   P

1051 AAG ATT ACA CGT AGT GCA TTG AGA CTT GTT TCA CTT GGA CCA 1092
          K   I   T   R   S   A   L   R   L   V   S   L   G   P

1093 CAT TAT CAT GAA TTT ACA GGT AAT GAT GAA GTT AAT GCA ACA 1134
          H   Y   H   E   F   T   G   N   D   E   V   N   A   T

1135 ATC ACT GCA CTT TTC AAA GGA ATT AGA GCC AAT TTA ACA GAA 1176
          I   T   A   L   F   K   G   I   R   A   N   L   T   E

1177 AGA TGT GAT AGA GAT AAA TGT TCA GGA TTT TGT GAT GCA ATG 1218
          R   C   D   R   D   K   C   S   G   F   C   D   A   M

1219 AAT AGA TGC ACA TGT CCA ATG TGT TGT GAG AAT GAT TGT TTC 1260
          N   R   C   T   C   P   M   C   C   E   N   D   C   F

1261 TAT ACA TCC TGT GAT GTA GAA ACA GGA TCA TGT ATT CCA TGG 1302
          Y   T   S   C   D   V   E   T   G   S   C   I   P   W

1303 CCT AAA GCT AAA CCA AAA GCA AAG AAA GAA TGT CCA GCA ACA 1344
          P   K   A   K   P   K   A   K   K   E   C   P   A   T

1345 TGT GTA GGC TCA TAT GAA TGT AGA GAT CTT GAA GGA TGT GTT 1386
          C   V   G   S   Y   E   C   R   D   L   E   G   C   V

1387 GTT ACA AAA TAT AAT GAC ACA TGC CAA CCA AAA GTG AAA TGC 1428
          V   T   K   Y   N   D   T   C   Q   P   K   V   K   C

1429 ATG GTA CCA TAT TGT GAT AAT GAT AAG AAT CTA ACT GAA GTA 1470
          M   V   P   Y   C   D   N   D   K   N   L   T   E   V

1471 TGT AAA CAA AAA GCT AAT TGT GAA GCA GAT CAA AAA CCA AGT 1512
          C   K   Q   K   A   N   C   E   A   D   Q   K   P   S

1513 TCT GAT GGA TAT TGT TGG AGT TAT ACA TGT GAC CAA ACT ACT 1554
          S   D   G   Y   C   W   S   Y   T   C   D   Q   T   T

1555 GGT TTT TGT AAG AAA GAT AAA CGA GGT AAA GAA ATG TGT ACA 1596
```

FIG. IA

```
            G   F   C   K   K   D   K   R   G   K   E   M   C   T
     1597 GGA AAG ACA AAT AAT TGT CAA GAA TAT GTT TGT GAT TCA GAA 1638
            G   K   T   N   N   C   Q   E   Y   V   C   D   S   E

1639 CAA AGA TGT AGT GTT AGA GAT AAA GTA TGT GTA AAA ACA TCA 1680
            Q   R   C   S   V   R   D   K   V   C   V   K   T   S

1681 CCA TAC ATT GAA ATG TCA TGT TAT GTA GCC AAG TGT AAT CTC 1722
            P   Y   I   E   M   S   C   Y   V   A   K   C   N   L

1723 AAT ACA GGT ATG TGT GAG AAC AGA TTA TCA TGT GAT ACA TAC 1764
            N   T   G   M   C   E   N   R   L   S   C   D   T   Y

1765 TCA TCA TGT GGT GGA GAT TCT ACA GGA TCA GTA TGT AAA TGT 1806
            S   S   C   G   G   D   S   T   G   S   V   C   K   C

1807 GAT TCT ACA ACT GGT AAT AAA TGT CAA TGT AAT AAA GTA AAA 1848
            D   S   T   T   G   N   K   C   Q   C   N   K   V   K

1849 AAT GGT AAT TAT TGT AAT TCT AAA AAC CAT GAA ATT TGT GAT 1890
            N   G   N   Y   C   N   S   K   N   H   E   I   C   D

1891 TAT ACA GGA ACA ACA CCA CAA TGT AAA GTG TCT AAT TGT ACA 1932
            Y   T   G   T   T   P   Q   C   K   V   S   N   C   T

1933 GAA GAT CTT GTT AGA GAT GGA TGT CTT ATT AAG AGA TGC AAT 1974
            E   D   L   V   R   D   G   C   L   I   K   R   C   N

1975 GAA ACA AGT AAA ACA ACA TAT TGG GAG AAT GTT GAT TGT TCA 2016
            E   T   S   K   T   T   Y   W   E   N   V   D   C   S

2017 AAC ACT AAG ATT GAA TTT GCT AAA GAT GAT AAA TCT GAA ACT 2058
            N   T   K   I   E   F   A   K   D   D   K   S   E   T

2059 ATG TGT AAA CAA TAT TAT TCA ACT ACA TGT TTG AAT GGA AAA 2100
            M   C   K   Q   Y   Y   S   T   T   C   L   N   G   K

2101 TGT GTT GTT CAA GCA GTT GGT GAT GTT TCT AAT GTA GGA TGT 2142
            C   V   V   Q   A   V   G   D   V   S   N   V   G   C

2143 GGA TAT TGT TCA ATG GGA ACA GAT AAT ATT ATT ACA TAT CAT 2184
            G   Y   C   S   M   G   T   D   N   I   I   T   Y   H
```

FIG. IA

```
2185  GAT GAT TGT AAT TCA CGT AAA TCA CAA TGT GGA AAC TTT AAT  2226
       D   D   C   N   S   R   K   S   Q   C   G   N   F   N

2227  GGT AAA TGT ATT AAA GGC AGT GAC AAT TCT TAT TCT TGT GTA  2268
       G   K   C   I   K   G   S   D   N   S   Y   S   C   V

2269  TTT GAA AAA GAT AAA ACT TCT TCT AAA TCA GAT AAT GAT ATT  2310
       F   E   K   D   K   T   S   S   K   S   D   N   D   I

2311  TGT GCT GAA TGT TCT AGT TTA ACA TGT CCA GCT GAT ACT ACA  2352
       C   A   E   C   S   S   L   T   C   P   A   D   T   T

2353  TAC AGA ACA TAT ACA TAT GAC TCA AAA ACA GGA ACA TGT AAA  2394
       Y   R   T   Y   T   Y   D   S   K   T   G   T   C   K

2395  GCA ACT GTT CAA CCA ACA CCA GCA TGT TCA GTA TGT GAA AGT  2436
       A   T   V   Q   P   T   P   A   C   S   V   C   E   S

2437  GGT AAA TTT GTA GAG AAA TGC AAA GAT CAA AAA TTA GAA CGT  2478
       G   K   F   V   E   K   C   K   D   Q   K   L   E   R

2479  AAA GTC ACT TTA GAA AAT GGA AAA GAA TAT AAA TAC ACC ATT  2520
       K   V   T   L   E   N   G   K   E   Y   K   Y   T   I

2521  CCA AAA GAT TGT GTC AAT GAA CAA TGC ATT CCA AGA ACA TAC  2562
       P   K   D   C   V   N   E   Q   C   I   P   R   T   Y

2563  ATA GAT TGT TTA GGT AAT GAT GAT AAC TTT AAA TCT ATT TAT  2604
       I   D   C   L   G   N   D   D   N   F   K   S   I   Y

2605  AAC TTC TAT TTA CCA TGT CAA GCA TAT GTT ACA GCT ACC TAT  2646
       N   F   Y   L   P   C   Q   A   Y   V   T   A   T   Y

2647  CAT TAC AGT TCA TTA TTC AAT TTA ACT AGT TAT AAA CTT CAC  2688
       H   Y   S   S   L   F   N   L   T   S   Y   K   L   H

2689  TTA CCA CAA AGT GAA GAA TTT ATG AAA GAG GCA GAC AAA GAA  2730
       L   P   Q   S   E   E   F   M   K   E   A   D   K   E

2731  GCA TAT TGT ACA TAC GAA ATA ACA ACA AGA GAA TGT AAA ACA  2772
       A   Y   C   T   Y   E   I   T   T   R   E   C   K   T

2773  TGT TCA TTA ATT GAA ACT AGA GAA AAA GTC CAA GAA GTT GAT  2814
       C   S   L   I   E   T   R   E   K   V   Q   E   V   D

2815  TTG TGT GCA GAA GAA ACT AAG AAT GGA GGA GTT CCA TTC AAA  2856
       L   C   A   E   E   T   K   N   G   G   V   P   F   K

2857  TGT AAG AAT AAC AAT TGC ATT ATT GAT CCT AAC TTT GAT TGT  2898
       C   K   N   N   N   C   I   I   D   P   N   F   D   C

2899  CAA CCT ATT GAA TGT AAG ATT CAA GAG ATT GTT ATT ACA GAA  2940
       Q   P   I   E   C   K   I   Q   E   I   V   I   T   E

2941  AAA GAT GGA ATA AAA ACA ACA ACA TGT AAA AAT ACT ACA AAA  2982
       K   D   G   I   K   T   T   T   C   K   N   T   T   K
```

FIG. IA

```
2983  GCA ACA TGT GAC ACT AAC AAT AAG AGA ATA GAA GAT GCA CGT  3024
       A   T   C   D   T   N   N   K   R   I   E   D   A   R

3025  AAA GCA TTC ATT GAA GGA AAA GAA GGA ATT GAG CAA GTA GAA  3066
       K   A   F   I   E   G   K   E   G   I   E   Q   V   E

3067  TGT GCA AGT ACT GTT TGT CAA AAT GAT AAT AGT TGT CCA ATT  3108
       C   A   S   T   V   C   Q   N   D   N   S   C   P   I

3109  ATT ACT GAT GTA GAA AAA TGT AAT CAA AAC ACA GAA GTA GAT  3150
       I   T   D   V   E   K   C   N   Q   N   T   E   V   D

3151  TAT GGA TGT AAA GCA ATG ACA GGA GAA TGT GAT GGT ACT ACA  3192
       Y   G   C   K   A   M   T   G   E   C   D   G   T   T

3193  TAT CTT TGT AAA TTT GTA CAA CTT ACT GAT GAT CCA TCA TTA  3234
       Y   L   C   K   F   V   Q   L   T   D   D   P   S   L

3235  GAT AGT GAA CAT TTT AGA ACT AAA TCA GGA GTT GAA CTT AAC  3276
       D   S   E   H   F   R   T   K   S   G   V   E   L   N

3277  AAT GCA TGT TTG AAA TAT AAA TGT GTT GAG AGT AAA GGA AGT  3318
       N   A   C   L   K   Y   K   C   V   E   S   K   G   S

3319  GAT GGA AAA ATC ACA CAT AAA TGG GAA ATT GAT ACA GAA CGA  3360
       D   G   K   I   T   H   K   W   E   I   D   T   E   R

3361  TCA AAT GCT AAT CCA AAA CCA AGA AAT CCA TGC GAA ACC GCA  3402
       S   N   A   N   P   K   P   R   N   P   C   E   T   A

3403  ACA TGT AAT CAA ACA ACT GGA GAA ACT ATT TAC ACA AAG AAA  3444
       T   C   N   Q   T   T   G   E   T   I   Y   T   K   K

3445  ACA TGT ACT GTT TCA GAA TTC CCA ACA ATC ACA CCA AAT CAA  3486
       T   C   T   V   S   E   F   P   T   I   T   P   N   Q

3487  GGA AGA TGT TTC TAT TGT CAA TGT TCA TAT CTT GAC GGT TCA  3528
       G   R   C   F   Y   C   Q   C   S   Y   L   D   G   S

3529  TCA GTT CTT ACT ATG TAT GGA GAA ACA GAT AAA GAA TAT TAT  3570
       S   V   L   T   M   Y   G   E   T   D   K   E   Y   Y
```

FIG. 1A

3571 GAT CTT GAT GCA TGT GGT AAT TGT CGT GTT TGG AAT CAG ACA 3612
    D   L   D   A   C   G   N   C   R   V   W   N   Q   T

3613 GAT AGA ACA CAA CAA CTT AAT AAT CAC ACC GAG TGT ATT CTC 3654
    D   R   T   Q   Q   L   N   N   H   T   E   C   I   L

3655 GCA GGA GAA ATT AAT AAT GTT GGA GCT ATT GCA GCG GCA ACT 3696
    A   G   E   I   N   N   V   G   A   I   A   A   A   T

3697 ACT GTG GCT GCT GTT ATA GTT GCA GTT GTA GTT GCA TTA ATT 3738
    T   V   A   A   V   I   V   A   V   V   V   A   L   I

3739 GTT GTT TCT ATT GGA TTA TTT AAG ACT TAT CAA CTT GTT TCA 3780
    V   V   S   I   G   L   F   K   T   Y   Q   L   V   S

3781 TCA GCT ATG AAG AAT GCC ATT ACA ATA ACT AAT GAA AAT GCA 3822
    S   A   M   K   N   A   I   T   I   T   N   E   N   A

3823 GAA TAT GTT GGA GCA GAT AAT GAA GCA ACT AAT GCA GCA ACA 3864
    E   Y   V   G   A   D   N   E   A   T   N   A   A   T

3865 TTC AAT GGA TAA GAA CAA TAA TTA AGC C     3892
    F   N   G   Z   E   Q   Z   L   S

FIG. IA

```
  -15         MKLLL  LNILLLCCLA  DKLDEFSADN  DYYDGGIMSR  GKNAGSWYHS
   31  YTHQYDVFYY  LAMQPWRHFV  WTTCDKNDNT  ECYKYTINED  HNVKVEDINK
   81  TNIKQDFCQK  EYAYPIEKYE  VDWDNVPVDE  QRIESVDING  KTCFKYAAKR
  131  PLAYVYLNTK  MTYATKTEAY  DVCRMDFIGG  RSITFRSFNT  ENKAFIDQYN
  181  TNTTSKCLLN  VYDNNVNTHL  AIIFGITDST  VIKSLQENLS  LLSQLKTVKG
  231  VTLYYLKDDT  YFTVNITLDQ  LKYDTLVKYT  AGTGQVDPLI  NIAKNDLATK
  281  VADKSKDKNA  NDKIKRGTMI  VLMDTALGSE  FNAETEFDRK  NISVHTVVLN
  331  RNKDPKITRS  ALRLVSLGPH  YHEFTGNDEV  NATITALFKG  IRANLTERCD
  381  RDKCSGFCDA  MNRCTCPMCC  ENDCFYTSCD  VETGSCIPWP  KAKPKAKKEC
  431  PATCVGSYEC  RDLEGCVVTK  YNDTCQPKVK  CMVPYCDNDK  NLTEVCKQKA
  481  NCEADQKPSS  DGYCWSYTCD  QTTGFCKKDK  RGKEMCTGKT  NNCQEYVCDS
  531  EQRCSVRDKV  CVKTSPYIEM  SCYVAKCNLN  TGMCENRLSC  DTYSSCGGDS
  581  TGSVCKCDST  TGNKCQCNKV  KNGNYCNSKN  HEICDYTGTT  PQCKVSNCTE
  631  DLVRDGCLIK  RCNETSKTTY  WENVDCSNTK  IEFAKDDKSE  TMCKQYYSTT
  681  CLNGKCVVQA  VGDVSNVGCG  YCSMGTDNII  TYHDDCNSRK  SQCGNFNGKC
  731  IKGSDNSYSC  VFEKDKTSSK  SDNDICAECS  SLTCPADTTY  RTYTYDSKTG
  781  TCKATVQPTP  ACSVCESGKF  VEKCKDQKLE  RKVTLENGKE  YKYTIPKDCV
  831  NEQCIPRTYI  DCLGNDDNFK  SIYNFYLPCQ  AYVTATYHYS  SLFNLTSYKL
  881  HLPQSEEFMK  EADKEAYCTY  EITTRECKTC  SLIETREKVQ  EVDLCAEETK
  931  NGGVPFKCKN  NNCIIDPNFD  CQPIECKIQE  IVITEKDGIK  TTTCKNTTKA
  981  TCDTNNKRIE  DARKAFIEGK  EGIEQVECAS  TVCQNDNSCP  IITDVEKCNQ
 1031  NTEVDYGCKA  MTGECDGTTY  LCKFVQLTDD  PSLDSEHFRT  KSGVELNNAC
 1081  LKYKCVESKG  SDGKITHKWE  IDTERSNANP  KPRNPCETAT  CNQTTGETIY
 1131  TKKTCTVSEF  PTITPNQGRC  FYCQCSYLDG  SSVLTMYGET  DKEYYDLDAC
 1181  GNCRVWNQTD  RTQQLNNHTE  CILAGEINNV  GAIAAATTVA  AVIVAVVVAL
 1231  IVVSIGLFKT  YQLVSSAMKN  AITITNENAE  YVGADNEATN  AATFNG
```

FIG. IB

Expression construct for fragments of *hgl1*

```
  1 TTC TGT TAA ATA GGA AAG GCA AGT GAT TTA AAC AAG ACA ATG   42

43 AAC TAG AAA GAC AAA GAT ATG AAA TTA TTA TTA TTA AAT ATC   84
                             M   K   L   L   L   L   N   I

85 TTA TTA TTA TGT TGT CTT GCA GAT AAA CTT AAT GAA TTT TCA  126
     L   L   L   C   C   L   A   D   K   L   N   E   F   S

127 GCA GAT ATT GAT TAT TAT GAC CTT GGT ATT ATG TCT CGT GGA  168
     A   D   I   D   Y   Y   D   L   G   I   M   S   R   G

169 AAG AAT GCA GGT TCA TGG TAT CAT TCT TAT GAA CAT CAA TAT  210
     K   N   A   G   S   W   Y   H   S   Y   E   H   Q   Y

211 GAT GTT TTC TAT TAT TTA GCT ATG CAA CCA TGG AGA CAT TTT  252
     D   V   F   Y   Y   L   A   M   Q   P   W   R   H   F

253 GTA TGG ACT ACT TGT ACA ACA ACT GAT GGC AAT AAA GAA TGT  294
     V   W   T   T   C   T   T   T   D   G   N   K   E   C

295 TAT AAA TAT ACT ATC AAT GAA GAT CAT AAT GTA AAG GTT GAA  336
     Y   K   Y   T   I   N   E   D   H   N   V   K   V   E

337 GAT ATT AAT AAA ACA GAT ATT AAA CAA GAT TTT TGT CAA AAA  378
     D   I   N   K   T   D   I   K   Q   D   F   C   Q   K

379 GAA TAT GCA TAT CCA ATT GAA AAA TAT GAA GTT GAT TGG GAC  420
     E   Y   A   Y   P   I   E   K   Y   E   V   D   W   D

421 AAT GTT CCA GTT GAT GAA CAA CGA ATT GAA AGT GTA GAT ATT  462
     N   V   P   V   D   E   Q   R   I   E   S   V   D   I

463 AAT GGA AAA ACT TGT TTT AAA TAT GCA GCT AAA AGA CCA TTG  504
     N   G   K   T   C   F   K   Y   A   A   K   R   P   L

505 GCT TAT GTT TAT TTA AAT ACA AAA ATG ACA TAT GCA ACA AAA  546
     A   Y   V   Y   L   N   T   K   M   T   Y   A   T   K

547 ACT GAA GCA TAT GAT GTT TGT AGA ATG GAT TTC ATT GGA GGA  588
     T   E   A   Y   D   V   C   R   M   D   F   I   G   G

589 AGA TCA ATT ACA TTC AGA TCA TTT AAC ACA GAG AAT AAA GCA  630
     R   S   I   T   F   R   S   F   N   T   E   N   K   A

631 TTT ATT GAT CAA TAT AAT ACA AAC ACT ACA TCA AAA TGT CTT  672
     F   I   D   Q   Y   N   T   N   T   T   S   K   C   L

673 CTT AAA GTA TAT GAT AAT AAT GTT AAT ACA CAT CTT GCA ATT  714
     L   K   V   Y   D   N   N   V   N   T   H   L   A   I

715 ATC TTT GGT ATT ACT GAT TCT ACA GTC ATT AAA TCA CTT CAA  756
     I   F   G   I   T   D   S   T   V   I   K   S   L   Q
```

FIG. 4A

```
757  GAG AAC TTA TCT CTT TTA AAT AAA TTA ACA ACA GTC AAA GGA  798
      E   N   L   S   L   L   N   K   L   T   T   V   K   G

799  GTA ACA CTC TAC TAT CTT AAA GAT GAT ACT TAT TTT ACA GTT  840
      V   T   L   Y   Y   L   K   D   D   T   Y   F   T   V

841  AAT ATT ACT TTA AAT GAT TTG AAA TAT GAG ACA CTT GTC CAA  882
      N   I   T   L   N   D   L   K   Y   E   T   L   V   Q

883  TAC ACA GCA GGA ACA GGA CAA GTT GAT CCA CTT ATT AAT ATT  924
      Y   T   A   G   T   G   Q   V   D   P   L   I   N   I

925  GCT AAG AAT GAC TTA ACT GCT AAA GTT GCA GAT AAA AGT AAA  966
      A   K   N   D   L   T   A   K   V   A   D   K   S   K

967  GAT AAA AAT GCA AAT GAT AAA ATC AAA AGA GGA ACT ATG ATT 1008
      D   K   N   A   N   D   K   I   K   R   G   T   M   I

1009 GTG TTA ATG GAT ACT GCA CTT GGA TCA GAA TTT AAT GCG GAA 1050
      V   L   M   D   T   A   L   G   S   E   F   N   A   E

1051 ACA GAA TTT GAT AGA AAG AAT ATT TCA GTT CAT ACT GTT GTT 1092
      T   E   F   D   R   K   N   I   S   V   H   T   V   V

1093 CTT AAT AGA AAT AAA GAC CCA AAG ATT ACA CGT AGT GCA TTG 1134
      L   N   R   N   K   D   P   K   I   T   R   S   A   L

1135 AGA CTT GTT TCA CTT GGA CCA CAT TAT CAT GAA TTT ACA GGT 1176
      R   L   V   S   L   G   P   H   Y   H   E   F   T   G

1177 AAT GAT GAA GTT AAT GCA ACA ATC ACT GCA CTT TTC AAA GGA 1218
      N   D   E   V   N   A   T   I   T   A   L   F   K   G

1219 ATT AGA GCC AAT TTA ACA GAA AGA TGT GAT AGA GAT AAA TGT 1260
      I   R   A   N   L   T   E   R   C   D   R   D   K   C

1261 TCA GGA TTT TGT GAT GCA ATG AAT AGA TGC ACA TGT CCA ATG 1302
      S   G   F   C   D   A   M   N   R   C   T   C   P   M

1303 TGT TGT GAG AAT GAT TGT TTC TAT ACA TCC TGT GAT GTA GAA 1344
      C   C   E   N   D   C   F   Y   T   S   C   D   V   E

1345 ACA GGA TCA TGT ATT CCA TGG CCT AAA GCT AAA CCA AAA GCA 1386
      T   G   S   C   I   P   W   P   K   A   K   P   K   A

1387 AAG AAA GAA TGT CCA GCA ACA TGT GTA GGC TCA TAT GAA TGT 1428
      K   K   E   C   P   A   T   C   V   G   S   Y   E   C

1429 AGA GAT CTT GAA GGA TGT GTT GTT AAA CAA TAT AAT ACA TCT 1470
      R   D   L   E   G   C   V   V   K   Q   Y   N   T   S

1471 TGT GAA CCA AAA GTG AAA TGC ATG GTA CCA TAT TGT GAT AAT 1512
      C   E   P   K   V   K   C   M   V   P   Y   C   D   N
```

FIG. 4B

```
1513 GAT AAG AAT CTA ACT GAA GTA TGT AAA CAA AAA GCT AAT TGT 1554
      D   K   N   L   T   E   V   C   K   Q   K   A   N   C

1555 GAA GCA GAT CAA AAA CCA AGT TCT GAT GGA TAT TGT TGG AGT 1596
      E   A   D   Q   K   P   S   S   D   G   Y   C   W   S

1597 TAT ACA TGT GAC CAA ACT ACT GGT TTT TGT AAG AAA GAT AAA 1638
      Y   T   C   D   Q   T   T   G   F   C   K   K   D   K

1639 CGT GGT GAA AAT ATG TGT ACA GGA AAG ACA AAT AAC TGT CAA 1680
      R   G   E   N   M   C   T   G   K   T   N   N   C   Q

1681 GAA TAT GTT TGT GAT GAA AAA CAA AGA TGT ACT GTT CAA GAA 1722
      E   Y   V   C   D   E   K   Q   R   C   T   V   Q   E

1723 AAG GTA TGT GTA AAA ACA TCA CCT TAT ATT GAA ATG TCA TGT 1764
      K   V   C   V   K   T   S   P   Y   I   E   M   S   C

1765 TAT GTA GCC AAG TGT AAT CTC AAT ACA GGT ATG TGT GAG AAC 1806
      Y   V   A   K   C   N   L   N   T   G   M   C   E   N

1807 AGA TTA TCA TGT GAT ACA TAC TCA TCA TGT GGT GGA GAT TCT 1848
      R   L   S   C   D   T   Y   S   S   C   G   G   D   S

1849 ACA GGA TCA GTA TGT AAA TGT GAT TCT ACA ACT AAT AAC CAA 1890
      T   G   S   V   C   K   C   D   S   T   T   N   N   Q

1891 TGT CAA TGT ACT CAA GTA AAA AAC GGT AAT TAT TGT GAT TCT 1932
      C   Q   C   T   Q   V   K   N   G   N   Y   C   D   S

1933 AAT AAA CAT CAA ATT TGT GAT TAT ACA GGA AAA ACA CCA CAA 1974
      N   K   H   Q   I   C   D   Y   T   G   K   T   P   Q

1975 TGT AAA GTG TCT AAT TGT ACA GAA GAT CTT GTT AGA GAT GGA 2016
      C   K   V   S   N   C   T   E   D   L   V   R   D   G

2017 TGT CTT ATT AAG AGA TGT AAT GAA ACA AGT AAA ACA ACA TAT 2058
      C   L   I   K   R   C   N   E   T   S   K   T   T   Y

2059 TGG GAG AAT GTT GAT TGT TCT AAA ACT GAA GTT AAA TTC GCT 2100
      W   E   N   V   D   C   S   K   T   E   V   K   F   A

2101 CAA GAT GGT AAA TCT GAA AAT ATG TGT AAA CAA TAT TAT TCA 2142
      Q   D   G   K   S   E   N   M   C   K   Q   Y   Y   S

2143 ACT ACA TGT TTG AAT GGA CAA TGT GTT GTT CAA GCA GTT GGT 2184
      T   T   C   L   N   G   Q   C   V   V   Q   A   V   G

2185 GAT GTT TCT AAT GTA GGA TGT GGA TAT TGT TCA ATG GGA ACA 2226
      D   V   S   N   V   G   C   G   Y   C   S   M   G   T

2227 GAT AAT ATT ATT ACA TAT CAT GAT GAT TGT AAT TCA CGT AAA 2268
      D   N   I   I   T   Y   H   D   D   C   N   S   R   K
```

FIG. 4C

```
2269 TCA CAA TGT GGA AAC TTT AAT GGT AAG TGT GTA GAA AAT AGT 2310
     S   Q   C   G   N   F   N   G   K   C   V   E   N   S

2311 GAC AAA TCA TAT TCT TGT GTA TTT AAT AAG GAT GTT TCT TCT 2352
     D   K   S   Y   S   C   V   F   N   K   D   V   S   S

2353 ACA TCA GAT AAT GAT ATT TGT GCA AAA TGT TCT AGT TTA ACA 2394
     T   S   D   N   D   I   C   A   K   C   S   S   L   T

2395 TGT CCA GCT GAT ACT ACA TAC AGA ACA TAT ACA TAT GAC TCA 2436
     C   P   A   D   T   T   Y   R   T   Y   T   Y   D   S

2437 AAA ACA GGA ACA TGT AAA GCA ACT GTT CAA CCA ACA CCA GCA 2478
     K   T   G   T   C   K   A   T   V   Q   P   T   P   A

2479 TGT TCA GTA TGT GAA AGT GGT AAA TTT GTA GAA AAA TGC AAA 2520
     C   S   V   C   E   S   G   K   F   V   E   K   C   K

2521 GAT CAA AAA TTA GAA CGT AAA GTT ACT TTA GAA AAT GGA AAA 2562
     D   Q   K   L   E   R   K   V   T   L   E   N   G   K

2563 GAA TAT AAA TAC ACC ATT CCA AAA GAT TGT GTC AAT GAA CAA 2604
     E   Y   K   Y   T   I   P   K   D   C   V   N   E   Q

2605 TGC ATT CCA AGA ACA TAC ATA GAT TGT TTA GGT AAT GAT GAT 2646
     C   I   P   R   T   Y   I   D   C   L   G   N   D   D

2647 AAC TTT AAA TCT ATT TAT AAC TTC TAT TTA CCA TGT CAA GCA 2688
     N   F   K   S   I   Y   N   F   Y   L   P   C   Q   A

2689 TAT GTT ACA GCT ACC TAT CAT TAC AGT TCA TTA TTC AAT TTA 2730
     Y   V   T   A   T   Y   H   Y   S   S   L   F   N   L

2731 ACT AGT TAT AAA CTT CAT TTA CCA CAA AGT GAA GAA TTT ATG 2772
     T   S   Y   K   L   H   L   P   Q   S   E   E   F   M

2773 AAA GAG GCA GAC AAA GAA GCA TAT TGT ACA TAC GAA ATA ACA 2814
     K   E   A   D   K   E   A   Y   C   T   Y   E   I   T

2815 ACA AGA GAA TGT AAA ACA TGT TCA TTA ATT GAA ACT AGA GAA 2856
     T   R   E   C   K   T   C   S   L   I   E   T   R   E

2857 AAA GTC CAA GAA GTT GAT TTG TGT GCA GAA GAG ACT AAG AAT 2898
     K   V   Q   E   V   D   L   C   A   E   E   T   K   N

2899 GGA GGA GTT CCA TTC AAA TGT AAG AAT AAC AAT TGC ATT ATT 2940
     G   G   V   P   F   K   C   K   N   N   N   C   I   I

2941 GAT CCT AAC TTT GAT TGT CAA CCT ATT GAA TGT AAG ATT CAA 2982
     D   P   N   F   D   C   Q   P   I   E   C   K   I   Q

2983 GAG ATT GTT ATT ACA GAA AAA GAT GGA ATA AAA ACA ACA ACA 3024
     E   I   V   I   T   E   K   D   G   I   K   T   T   T
```

FIG. 4D

```
3025 TGT AAA AAT ACC ACA AAA ACA ACA TGT GAC ACT AAC AAT AAG 3066
      C   K   N   T   T   K   T   T   C   D   T   N   N   K

3067 AGA ATA GAA GAT GCA CGT AAA GCA TTC ATT GAA GGA AAA GAA 3108
      R   I   E   D   A   R   K   A   F   I   E   G   K   E

3109 GGA ATT GAG CAA GTA GAA TGT GCA AGT ACT GTT TGT CAA AAT 3150
      G   I   E   Q   V   E   C   A   S   T   V   C   Q   N

3151 GAT AAT AGT TGT CCA ATT ATT ACT GAT GTA GAA AAA TGT AAT 3192
      D   N   S   C   P   I   I   T   D   V   E   K   C   N

3193 CAA AAC ACA GAA GTA GAT TAT GGA TGT AAA GCA ATG ACA GGA 3234
      Q   N   T   E   V   D   Y   G   C   K   A   M   T   G

3235 GAA TGT GAT GGT ACT ACA TAT CTT TGT AAA TTT GTA CAA CTT 3276
      E   C   D   G   T   T   Y   L   C   K   F   V   Q   L

3277 ACT GAT GAT CCA TCA TTA GAT AGT GAA CAT TTT AGA ACT AAA 3318
      T   D   D   P   S   L   D   S   E   H   F   R   T   K

3319 TCA GGA GTT GAA CTT AAC AAT GCA TGT TTG AAA TAT AAA TGT 3360
      S   G   V   E   L   N   N   A   C   L   K   Y   K   C

3361 GTT GAG AGT AAA GGA AGT GAT GGA AAA ATC ACA CAT AAA TGG 3402
      V   E   S   K   G   S   D   G   K   I   T   H   K   W

3403 GAA ATT GAT ACA GAA CGA TCA AAT GCT AAT CCA AAA CCA AGA 3444
      E   I   D   T   E   R   S   N   A   N   P   K   P   R

3445 AAT CCA TGC GAA ACC GCA ACA TGT AAT CAA ACA ACT GGA GAA 3486
      N   P   C   E   T   A   T   C   N   Q   T   T   G   E

3487 ACT ATT TAC ACA AAG AAA ACA TGT ACT GTT TCA GAA GAA TTC 3528
      T   I   Y   T   K   K   T   C   T   V   S   E   E   F

3529 CCA ACA ATC ACA CCA AAT CAA GGA AGA TGT TTC TAT TGT CAA 3570
      P   T   I   T   P   N   Q   G   R   C   F   Y   C   Q

3571 TGT TCA TAT CTT GAC GGT TCA TCA GTT CTT ACT ATG TAT GGA 3612
      C   S   Y   L   D   G   S   S   V   L   T   M   Y   G

3613 GAA ACA GAT AAA GAA TAT TAT GAT CTT GAT GCA TGT GGT AAT 3654
      E   T   D   K   E   Y   Y   D   L   D   A   C   G   N

3655 TGT CGT GTT TGG AAT CAG ACA GAT AGA ACA CAA CPA CTT AAT 3696
      C   R   V   W   N   Q   T   D   R   T   Q   Q   L   N

3697 AAT CAC ACC GAG TGT ATT CTC GCA GGA GAA ATT AAT AAT GTT 3738
      N   H   T   E   C   I   L   A   G   E   I   N   N   V

3739 GGA GCT ATT GCA GCG GCA ACT ACT GTG GCT GTA GTT GTA GTT 3780
      G   A   I   A   A   A   T   T   V   A   V   V   V   V
```

FIG. 4E

```
3781 GCA GTC GTA GTT GCA TTA ATT GTT GTT TCT ATT GGA TTA TTT 3822
     A   V   V   V   A   L   I   V   V   S   I   G   L   F

3823 AAG ACT TAT CAA CTT GTT TCA TCA GCT ATG AAG AAT GCC ATT 3864
     K   T   Y   Q   L   V   S   S   A   M   K   N   A   I

3865 ACA ATA ACT AAT GAA AAT GCA GAA TAT GTT GGA GCA GAT AAT 3906
     T   I   T   N   E   N   A   E   Y   V   G   A   D   N

3907 GAA GCA ACT AAT GCA GCA ACA TTC AAT GGA TAA GAA CAA TAA 3948
     E   A   T   N   A   A   T   F   N   G   Z

3949 TTA AGA GAA TTG AAT AAC ATT TTA TGT TTT TAG ATT AAA AAT 3990

3991 AAA AAG AAG AAT AAA TTG AGT GAT AAA CAA TGA ATA AAA TAA 4032

4033 ATA AAA ATA AAC AAG AAT AAA GTG AAC ATC ATT TTT ATT TTC 4074

4075 ATA TTT TAA CAA CAC T 4090
```

FIG. 4F

```
 -15  MKLLLNILL  LCCLADKLNE  FSADIDYYDL  GIMSRGKNAG  SWYHSYEHQY  DVFYYLAMQP  WRHFVWTTCT  TTDGNKECYK
  66  YTINEDHNVK  VEDINKTDIK  QDFCQKEYAY  PIEKYEVDWD  NVPVDEQRIE  SVDINGKTCF  KYAAKRPLAY  VYLNTKMTYA
 146  TKTEAYDVCR  MDFIGGRSIT  FRSFNTENKA  FIDQYNTNTT  SKCLLKVYDN  NVNTHLAIIF  GITDSTVIKS  LQENLSLLNK
 226  LTTVKGVTLY  YLKDDTYFTV  NITLNDLKYE  TLVQYTAGTG  QVDPLINIAK  NDLTAKVADK  SKDKNANDKI  KRGTMIVLMD
 306  TALGSEFNAE  TEFDRKNISV  HTVLNRNKD   PKITRSALRL  VSLGPHYHEF  TGNDEVNATI  TALFKGIRAN  LTERCDRDKC
 386  SGFCDAMNRC  TCPMCCENDC  FYTSCDVETG  DQKPSSDGYC  WSYTCDQTTG  FCKKDKRGEN  MCTGKTNNCQ  CEPKVKCMVP
 466  YCDNDKNLTE  VCKQKANCEA  DQKPSSDGYC  WSYTCDQTTG  SCGGDSTGSV  CKCDSTTNNQ  EYVCDEKQRC  TVQEKVCVKT
 546  SPYIEMSCYV  AKCNLNTGMC  BGCLIKRCNE  TSKTTYWENV  DCSKTEVKFA  QDGKSENMCK  CQCTQVKNGN  YCDSNKHQIC  DYTGKTPQCK
 626  VSNCTEDLVR  DCNSRKSQCG  NFNGKCVENS  DKSYSCVFNK  PKDCVNEQCI  QYYSTTCLNG  QCVVQAVGDV  SNVGGCYCSM
 706  GTDNIITYHD  ESGKFVEKCK  DQKLERKVTL  ENGKEYKYTI  ECKTCSLIET  PRTYIDCLGN  CAKCSSLTCP  ADTTYRTYTY  DSKTGTCKAT
 786  VQPTPACSVC  TSYKLHLPQS  EEFMKEADKE  AYCTYEITTR  NTTKTTCDTN  REKVQEVDLC  NKRIEDARKA  DDNFKSIYNF  YLPCQAYVTA
 866  TYHYSSLFNL  CKIQEIVITE  KDGIKTTTCK  DGTTYLCKFV  QLTDDPSLDS  EHFRTKSGVE  FIEGKEGIEQ  AEETKNGGVP  FKCKNNNCII
 946  DPNFDCQPIE  YGCKAMTGEC  CETATCNQTT  GETIYKKTC   TVSEEFPTIT  PNQGRCFYCQ  LNNACLKYKC  VECASTVCQN  DNSCPIITDV
1026  EKCNQNTEVD  SNANPKPRNP  CETATCNQTT  GETIYKKTC   TVSEEFPTIT  PNQGRCFYCQ  CSYLDGSSVL  VESKGSDGKI  THKWEIDTER
1106  SNANPKPRNP  LNNHTECILA  GEINNVGAIA  AATTVAVVVV  AVVALIVVS   IGLFKTYQLV  SSAMKNAITI  TMYGETDKEY  YDLDACGNCR
1186  VWNQTDRTQQ  LNNHTECILA  GEINNVGAIA  AATTVAVVVV  AVVALIVVS   IGLFKTYQLV  SSAMKNAITI  TNENAEYVGA
1266  DNEATNAATF  NG
```

RECOMBINANT ENTAMOEBA HISTOLYTICA LECTIN SUBUNIT PEPTIDES AND REAGENTS SPECIFIC FOR MEMBERS OF THE 170 KD SUBUNIT MULTIGENE FAMILY

CROSS-REFERENCE TO RELATED APPLICATIONS

This application is national stage filing of PCT/US94/06890, filed Jun. 17, 1994, which claimed priority from two U.S. application Ser. Nos.: a continuation of U.S. Ser. No. 08/078,476, filed Jun. 17, 1993 (now abandoned) and its continuation-in-part, U.S. Ser. No. 08/130,735, filed Oct. 1, 1993 (now abandoned).

U.S. Ser. No. 08/078,476 (noted above) was a continuation-in-part of two application Ser. Nos.: U.S. Ser. No. 07/615,719, filed Nov. 21, 1990 (issued as U.S. Pat. No. 5,260,429) and U.S. Ser. No. 08/075,226 filed Jun. 10, 1993 (issued as U.S. Pat. No. 5,401,831). U.S. Ser. No. 08/075,226 and U.S. Ser. No. 07/615,719 both claimed priority (as a division and as a continuation-in-part, respectively) from U.S. Ser. No. 07/479,691, filed Feb. 13, 1990 (issued as U.S. Pat. No. 5,272,058), which was a continuation-in-part of U.S. Ser. No. 07/456,579, filed Dec. 29, 1989 (issued as U.S. Pat. No. 5,004,608), which was a continuation of U.S. Ser. No. 07/143,626, filed Jan. 13, 1988 (abandoned). All the applications cited above are hereby incorporated by reference in their entireties.

This invention was made, in part, with support supplied by the U.S. Government under Contracts AI 18841 and AI 26649 awarded by the National Institutes of Health. The U.S. Government has certain rights in this invention.

FIELD OF THE INVENTION

The invention concerns the use of epitope-bearing regions of the 170 kD subunit of Entamoeba histolytica Gal/GalNAc adherence lectin which are produced recombinantly in procaryotic systems in diagnosis and as vaccines. Thus, the invention relates to the determination of the presence, absence or amount of antibodies raised by a subject in response to infection by E. histolytica using these peptides and to vaccines incorporating them. This invention also particularly relates to reagents specific for a novel variant of the 170 kD subunit of E. histolytica Gal/GalNAc adherence lectin and to the gene (hgl3) which encodes this novel subunit form, which represents the third member of the multigene family encoding this 170 kD subunit.

BACKGROUND ART

Entamoeba histolytica infection is extremely common and affects an estimated 480 million individuals annually. However, only about 10% of these persons develop symptoms such as colitis or liver abscess. The low incidence of symptom occurrence is putatively due to the existence of both pathogenic and nonpathogenic forms of the amoeba. As of 1988, it had been established that the subjects who eventually exhibit symptoms harbor pathogenic "zymodemes" which have been classified as such on the basis of their distinctive hexokinase and phosphoglucomutase isoenzymes. The pathogenic forms are not conveniently distinguishable from the nonpathogenic counterparts using morphogenic criteria, but there is an almost perfect correlation between infection with a pathogenic zymodeme and development of symptoms and between infection with a non-pathogenic zymodeme and failure to develop these symptoms.

It is known that E. histolytica infection is mediated at least in part by the "Gal/GalNAc" adherence lectin which was isolated from a pathogenic strain and purified 500 fold by Petri, W. A., et al., J Biol Chem (1989) 264:3007–3012. The purified "Gal/GalNAc" lectin was shown to have a nonreduced molecular weight of 260 kD on SDS-PAGE; after reduction with beta-mercaptoethanol, the lectin separated into two subunits of 170 and 35 kD MW. Further studies showed that antibodies directed to the 170 kD subunit were capable of blocking surface adhesion to test cells (Petri, et al. J Biol Chem (1989) supra). Therefore, the 170 kD subunit is believed to be of primary importance in meditating adhesion.

In addition, the 170 kD subunit is described as constituting an effective vaccine to prevent E. histolytica infection in U.S. Pat. No. 5,004,608 issued Apr. 2, 1991.

Studies of serological cross-reactivity among patients having symptomology characteristic of E. histolytica pathogenic infection, including liver abscess and colitis, showed that the adherence lectin was recognized by all sera tested (Petri, Jr., W. A., et al., Am J Med Sci (1989) 296:163–165). The lectin heavy subunit is almost universally recognized by immune sera and T-cells from patients with invasive amebiasis (Petri, et al., Infect Immun (1987) 55:2327–2331; Schain, et al., Infect Immun (1992) 60:2143–2146).

DNA encoding both the heavy (170 kD) and light (35 kD) subunits have been cloned. The heavy and light subunits are encoded by distinct mRNAs (Mann, B., et al., Proc Natl Acad Sci USA (1991) 88:3248–3252) and these subunits have different amino acid compositions and amino terminal sequences. The sequence of the cDNA encoding the 170 kD subunit suggests it to be an integral membrane protein with a large cysteine-rich extracellular domain and a short cytoplasmic tail (Mann, B., et al., Proc Natl Acad Sci USA (1991) supra; Tannich, et al., Proc Natl Acad Sci USA (1991) 88:1849–1853). The derived amino acid sequence of the 170 kD lectin shows that the extracellular domain can be divided into three regions on the basis of amino acid composition. The amino terminal amino acids 1–187 are relatively rich in cysteine (3.2%) and tryptophan (2.1%). Amino acid sequence at positions 188–378 does not contain cysteine, and the amino acid sequence at positions 379–1209 contains 10.8% cysteine residues. The obtention of clones encoding the heavy chain subunit is further described in U.S. Pat. No. 5,260,429 issued Nov. 9, 1993, the disclosure of which is incorporated herein by reference. In that patent, diagnostic methods for the presence of E. histolytica based on the polymerase chain reaction and the use of DNA probes is described.

The heavy subunit is considered to be encoded by a multigene family (Mann, B., et al., Parasit Today (1991) 1:173–176). Two different heavy subunit genes, hgl1 and hgl2, have been sequenced by separate laboratories. While hgl2 was isolated from an HM-1:IMSS CDNA library in its entirety (Tannich, E. et al. Proc Natl Acad Sci USA (1991) 88:1849–1853), hgl1 was isolated in part from an H-302:NIH cDNA library and in part by PCR amplification of the gene from the HM-1:IMSS genome (Mann, B. J. et al. Proc Natl Acad Sci USA (1991) 88:3248–3252). As the amino acid sequence of these two genes is 87.6% identical (Mann, B. J. et al. Parasit Today (1991) 7:173–176), the differences could be explained by strain variation alone. The presence of multiple bands hybridizing to an hgl probe on Southern blots, however, in consistent with the existence of a 170 kDa subunit gene family (Tannich, E. et al. Proc Natl Acad Sci USA (1991) 88:1849–1853).

Monoclonal antibodies specifically immunoreactive with various epitope-bearing regions of the 170 kD heavy chain subunit have also been disclosed in U.S. Pat. No. 5,272,058 issued Dec. 21, 1993, the disclosure of which is incorporated herein by reference in its entirety. This application also describes use of these antibodies to detect the 170 kD heavy chain and the use of the 170 kD subunit to detect antibodies in serum or other biological samples. The experimental work described utilizes the native protein. Further characterization of these antibodies is described in a publication by Mann, B. J., et al., *Infect Immun* (1993) 61:1772–1778 also incorporated herein by reference.

Various immunoassay techniques have been used to diagnose *E. histolytica* infection. ELISA techniques have been used to detect the presence or absence of *E. histolytica* antigens both in stool specimens and in sera, though these tests do not seem to distinguish between the pathogenic and nonpathogenic strains. In a seminal article, Root, et al., *Arch Invest Med* (Mex) (1978) 9: Supplement 1:203, described the use of ELISA techniques for the detection of amoebic antigen in stool specimens using rabbit polyclonal antiserum, and various forms of this procedure have been used, some in conjunction with microscopic studies. Palacios et al., *Arch Invest Med* (Mex) (1978) 9: Supplement 1:203; Randall et al., *Trans Roy Soc Trop Med Hyg* (1984) 78:593; Grundy, *Trans Roy Soc Trop Med Hyg* (1982) 76:396; Ungar, *Am J Trop Med Hyg* (1985) 34:465. These studies on stool specimens and on other biological fluids are summarized in *Amebiasis: Human Infection by Entamoeba Histolytica,* J. Ravdin, ed. (1988) Wiley Medical Publishing, pp. 646–648.

Conversely, amebic serology is also a critical component in the diagnosis of invasive amebiasis. One approach utilizes conventional serologic tests, such as the indirect hemagglutinin test. These tests are very sensitive but seropositivity is persistent for years (Krupp, I. M., *Am J Trop Med Hyg* (1970) 19:57–62; Lobel, H. O. et al., *Ann Rev Microbiol* (1978) 32:379–347). Thus, healthy subjects may give positive responses to the assay, creating an undesirable high background. Similar problems with false positives are found in using immunoassay tests involving a monoclonal antibody and purified native 170 kD protein (Ravdin, J. I., et al., *J Infect Dis* (1990) 162:768–772.)

Recombinant *E. histolytica* proteins other than the 170 kD subunit have been used as the basis for serological tests. Western blotting using a recombinant form of the "52 kD serine-rich protein" was highly specific for invasive disease and had a higher predictive value (92 vs. 65%) than an agar gel diffusion test for diagnosis of acute amebiasis (Stanley, Jr., S. L., et al., *Proc Natl Acad Sci U.S.A.* (1990) 87:4976–4980; Stanley, Jr., S. L., et al., *JAMA* (1991) 266:1984–1986). However, the overall sensitivity was lower than for the conventional agar gel test (82% vs. 90–100%).

Thus, there remains a need for serological tests which will provide optimum sensitivity while minimizing the number of false positives retained. The present invention provides such a test by utilizing, as antigen, epitope-bearing portions of the 170 kD subunit of the adherence lectin produced recombinantly in procaryotic systems.

It is particularly advantageous to use recombinantly produced, nonglycosylated peptides or proteins in this assay since these peptides are easily and efficiently obtained and are easily standardized. Furthermore, since selected portions of the lectin heavy chain subunit can be produced, epitopes characteristic of the pathogenic or nonpathogenic forms of *E. histolytica* can be produced and used to distinguish these forms in the assays. Subsequent to the invention herein, a report of immunoreactivity of recombinant 170 kd lectin with immune sera was published by Zhang, Y, et al. *J. Clin Micro-immunol* (1992) 2788–2792. Applicants incorporate by reference their own publication: Mann, B. J et al. *Infect and Immun* (1993) 61: 1772–1778.

Similarly, although it is known that the 170 kD subunit may be used as a vaccine as described in the above-referenced U.S. Pat. No. 5,004,608, recombinantly produced forms of the 170 kD subunit, specifically those obtained from procaryotic cells that lack glycosylation may offer advantages in reproducibility of product and in ease of preparation of subunit vaccines. The present invention is directed to this desirable result.

DISCLOSURE OF THE INVENTION

The invention provides diagnostic tests which permit the assessment of patients for invasive *E. histolytica* infection and vaccines for prevention of infection. The invention also provides a novel third variant of the 170 kD subunit of the Gal/GalNAc adherence lectin and a gene (hgl3) which encodes this novel protein. Accordingly, the diagnostic tests of the invention are based on the genetic sequences of all three variants of the 170 kD subunit of the Gal/GalNAc adherence lectin which are encoded by three different genes in a multigene family.

Pathogenic and nonpathogenic strains can be distinguished by use of the invention diagnostic method, if desired. The tests use, as antigen, an epitope-bearing portion of the 170 kD subunit of the Gal/GalNAc adherence lectin recombinantly produced in procaryotic systems. Despite the absence of glycosylation from such portions and despite the lack of post-translational modifications characteristic of the native protein or peptide, the recombinantly produced proteins are effective antigens in these assays.

Thus, in one aspect, the invention is directed to a method to detect the presence or absence of antibodies immunoreactive with pathogenic and/or nonpathogenic *E. histolytica* in a biological sample which method comprises contacting the fluid with an epitope-bearing portion of the 170 kD heavy chain of the Gal/GalNAc adherence lectin wherein the lectin is nonglycosylated and in a form obtainable from procaryotic cells. If distinction between antibodies to the pathogenic and nonpathogenic forms is desired, the portion may be chosen so as to be characteristic of the pathogenic or nonpathogenic form. Alternatively, the assay may be conducted as a competition assay using MAbs with such characteristics. The contacting is conducted under conditions where the epitope-bearing portion forms complexes with any antibodies present in the biological fluid which are immunoreactive with an epitope on the portion. The presence, absence or amount of such complexes is then assessed, either directly or in a competition format, as a measure of the antibody contained in the biological sample. The invention is also directed to materials and kits suitable for performing the methods of the invention.

In a second aspect, the invention is directed to methods to prevent *E. histolytica* infection using vaccines containing, as active ingredient, epitope-bearing portions of the 170 kD subunit produced recombinantly in procaryotic systems, as described above. The invention is also directed to vaccines containing this active ingredient.

In other aspects, the invention is directed to epitope-bearing portions of the 170 kD subunit produced recombinantly in procaryotic systems and thus in a form characteristic of such production. One characteristic is lack of glycosylation; in addition, secondary structure of proteins produced by procaryotic hosts differs from that of proteins produced by the natural source.

In yet another aspect, the invention is directed to a DNA in purified and isolated form which consists essentially of a DNA encoding the 170 kd heavy chain subunit of pathogenic *E. histolytica* Gal/GalNAc adherence lectin, which subunit is encoded by the hgl3 gene for which the nucleotide sequence and deduced amino acid sequence are shown in FIGS. 4A–4F (SEQ ID NO:4 and SEQ ID NO:5). In further aspects, the invention is directed to both nucleic acid and immunological reagents which are enabled by the discovery of the hgl3 gene, reagents which are specific for each of the hgl1, hgl2 or hgl3 genes, as well as reagents which detect common regions of all three hgl genes or their nucleic acid or protein products. For example, oligonucleotide probes specific for any one of these three genes or for a sequence common to all three genes may be identified by one of ordinary skill in the art, using conventional nucleic acid probe design principles, by comparisons of the three DNA sequences for these genes. See Example 6.

In still further aspects, the invention is directed to a method to detect the presence, absence, or amount of a pathogenic or nonpathogenic form of *Entamoeba histolytica,* where *E. histolytica* has both pathogenic and nonpathogenic forms, in a biological sample, which method comprises contacting the sample with a monoclonal antibody immunospecific for an epitope of the 170 kd subunit of Gal/GalNAc lectin unique to the pathogenic or to the nonpathogenic form, or shared by the pathogenic and nonpathogenic forms of *E. histolytica,* to form an immunocomplex when the pathogenic and/or nonpathogenic form is present, and detecting the presence, absence or amount of the immunocomplex. In this method, the epitope is selected to be specific for one of 170 kD subunits encoded by the hgl1, hgl2 or hgl3 genes, or for a common region of the subunits from all three hgl genes. In another aspect, the invention is directed to a method to determine the presence, absence or amount of antibodies specifically immunoreactive with the Gal/GalNAc lectin derived from *E. histolytica,* which method comprises contacting a biological sample with the Gal/GalNAc lectin or the 170 kd subunit thereof in purified and isolated form, under conditions wherein antibodies immunospecific for said lectin or subunit will forma complex, and detecting the presence, absence or amount of the complex, wherein the purified and isolated Gal/GalNAc lectin or subunit is derived from either a pathogenic or nonpathogenic form of *E. histolytica,* and is a 170 kD subunit encoded by one of the hgl1, hgl2 or hgl3 genes. Detailed descriptions of these and related methods for detecting pathogenic or nonpathogenic forms of *E. histolytica* and antibodies specifically immunoreactive with the Gal/GalNAc lectin derived from *E. histolytica,* as well as reagent kits suitable for the conduct of such methods, are disclosed in U.S. Pat. No. 5,272,058, the entire disclosure of which is incorporated herein by reference.

BRIEF DESCRIPTION OF THE DRAWINGS

FIGS. 1A-1 through 1A-5 (SEQ ID NO:1 and SEQ ID NO:2) shows the DNA and amino acid sequence deduced from the nucleotide sequence corresponding to the 170 kD heavy chain of the adherence lectin from pathogenic strain HM1:IMSS, designated hgl1.

FIG. 1B (SEQ ID NO:3) shows the deduced amino acid sequence of hgl1 with the amino-terminal amino acid of the mature protein designated as amino acid number 1.

FIG. 3 is a diagram of the location of human B cell epitopes and pathogenic-specific epitopes on the 170 kD heavy chain.

FIGS. 4A–4F (SEQ ID NO:4 and SEQ ID NO:5) shows the DNA and amino acid sequence deduced from the nucleotide sequence corresponding to the 170 kD heavy chain of the adherence lectin from pathogenic strain HM1:IMSS, designated hgl3.

FIG. 5 (SEQ ID NO:6) shows the deduced amino acid sequence of hgl3 with the amino-terminal amino acid of the mature protein designated as amino acid number 1. The putative signal sequence and transmembrane domains are overlined and underlined respectively. Conserved cysteine residues (●) and potential sites of glycosylation (*) are indicated.

MODES OF CARRYING OUT THE INVENTION

Figure 2A:
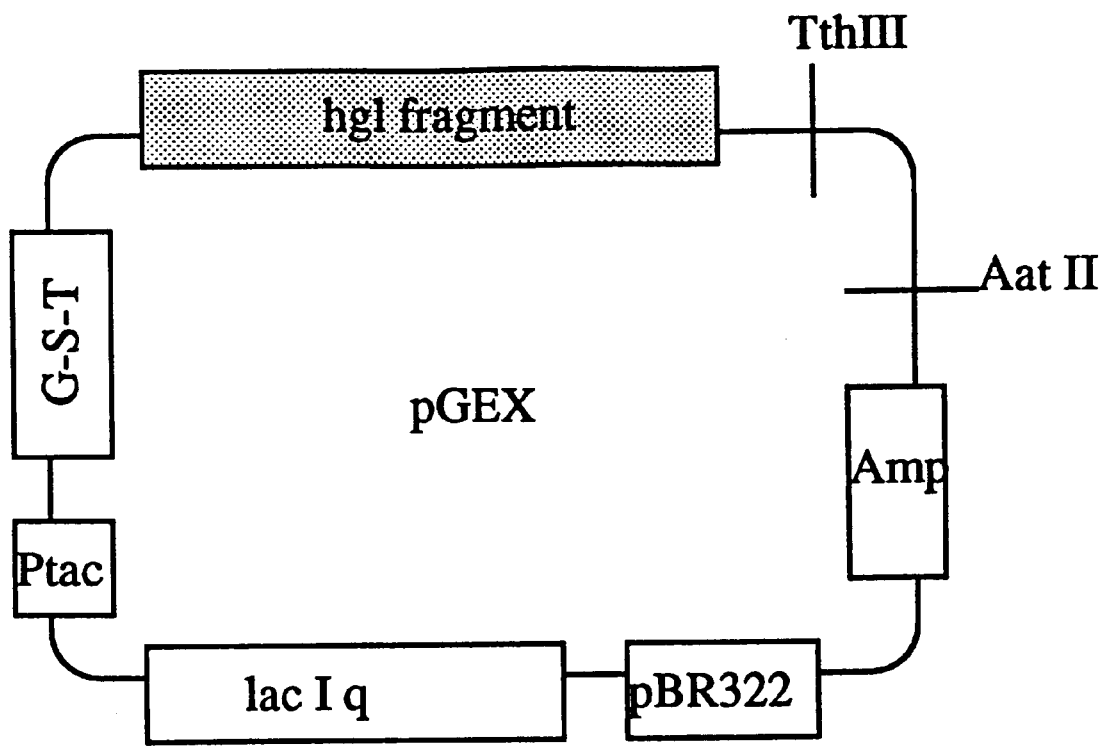
FIG. 2A is a diagram of the construction of expression vectors for recombinant production of specified portions of the 170 kD subunit.

The invention provides methods and materials which are useful in assays to detect antibodies directed to pathogenic and/or nonpathogenic forms of *E. histolytica* and in vaccines. The diagnostic assays can be conducted on biological samples derived from subjects at risk for infection or suspected of being infected. The assays can be designed to distinguish pathogenic from nonpathogenic forms of the amoeba if desired. The vaccines are administered to subjects at risk for amebic infections.

The assays of the invention rely on the ability of an epitope-bearing portion of the 170 kD subunit produced recombinantly in procaryotic cultures to immunoreact with antibodies contained in biological samples obtained from individuals who have been infected with *E. histolytica.* Even though the relevant peptide or protein is produced in a procaryotic system, and is thus not glycosylated or processed after translation in a manner corresponding to the native protein, the epitope-bearing portions thus prepared are useful antigens in immunoassays performed on samples prepared from biological fluids, cells, tissues or organs, or their diluted or fractionated forms. Similarly, these peptides are also immunogenic.

The use of recombinant forms of the antigen or offers advantages of cost-effective, reliable production of pure antigen, thus assuring the uniformity of the assay materials. Recombinant production in bacteria is a particularly efficient and useful method. It is surprising that such procaryotic systems can produce successful antigens and immunogens, since the peptides produced are not processed in a manner analogous to the reactive native forms.

Furthermore, recombinant production facilitates the preparation of specific epitopes, thus providing a means for detecting antibodies specifically immunoreactive with pathogenic or nonpathogenic forms of the amoeba, as well as offering the opportunity to provide subunit vaccines.

Thus, the invention is directed to methods to detect antibodies in biological samples and to immunize subjects at risk using these recombinantly produced epitope-bearing portions as antigens or immunogens as well as to the recombinantly produced peptides themselves and to materials useful in performing the assays and in administering the vaccines.

DEFINITIONS

The diagnostic assays may be designed to distinguish antibodies raised against nonpathogenic or pathogenic forms of the amoeba. "Pathogenic forms" of *E. histolytica* refers to those forms which are invasive and which result in symptomology to infected subjects. "Nonpathogenic forms" refers to those forms which may be harbored asymptomatically by carriers.

The assays and vaccines of the invention utilize an epitope-bearing portion of the 170 kD subunit of the Gal/GalNAc lectin. "Gal/GalNAc lectin" refers to glycoprotein found on the surface of *E. histolytica* which mediates the adherence of the amoeba to target cells, and which mediation is inhibited by galactose or N-acetylgalactosamine. The Gal/GalNAc lectin refers specifically to the lectin reported and isolated by Petri, et al. (supra) from the pathogenic strain HMI-IMSS, and to the corresponding lectin found in other strains of *E. histolytica*. The "170 kD subunit" refers to the large subunit, upon reduction of the Gal/GalNAc lectin, such as that obtained by Petri, et al. and shown in FIGS. 1A-1 to 1A-6 and FIG. 1B as well as to its corresponding counterparts in other strains.

DIAGNOSTIC ASSAYS

With respect to the diagnostic assays of the invention, the complete 170 kD antigen or an epitope-bearing portion thereof can be used in the assays. Such epitope-bearing portions can be selected as characteristic of pathogens or nonpathogens or common to both.

As shown hereinbelow, the portion of the 170 kD protein which contains epitopes for all monoclonal antibodies prepared against the lectin is found at amino acid positions 596–1138. There appears to be an epitope characteristic of pathogens between each of amino acid positions 596–818, 1082–1138, and 1033–1082. Positions 895–998 contain epitopes which are shared by pathogens and nonpathogens as well as epitopes characteristic of pathogenic strains. Thus, to utilize fragments of the recombinantly produced protein for detection of antibodies, a peptide representing positions 596–818, 1033–1082 or 1082–1138 may be used to detect antibodies raised against pathogens by hosts in general; however, the epitope at positions 596–816 is not recognized by human antisera. Mixtures of these peptides could also be used. Alternatively, longer forms of the antigen can be used by selecting the appropriate positions depending on whether pathogenic and nonpathogenic amoebae are to be distinguished.

As shown in Example 4, below, epitope-bearing portions relevant for human testing include portions 2–482, 1082–1138, 1032–1082 and 894–998. Only the portions represented by 1082–1138 and 1032–1082 appears specific for antibodies against pathogenic ameba. These epitope-bearing portions may be used as single peptides, as uniquely lectin-derived portions of chimeric proteins, as mixtures of peptides or of such proteins, or as portions of a single, multiple-epitope-bearing protein. Procedures for preparing recombinant peptide proteins containing only a single epitope-bearing portion identified above, or multiples of such portions (including tandem repeats) are well understood in the art.

The assays are designed to detect antibodies in biological samples which are "immunospecific" or "immunoreactive" with respect to the epitope-bearing portion—i.e. with respect to at least one epitope contained in this portion. As used herein, "immunospecific" or "immunoreactive" with respect to a specified target means that the antibody thus described binds that target with significantly higher affinity than that with which it binds to alternate haptens. The degree of specificity required may vary with circumstances, but typically an antibody immunospecific for a designated target will bind to that target with an affinity which is at least one or two, or preferably several orders or magnitude greater than with which it binds alternate haptens.

The assays can be performed in a wide variety of protocols depending on the nature of the sample, the circumstances of performing the assays, and the particular design chosen by the clinician. The biological sample is prepared in a manner standard for the conduct of immunoassays; such preparation may involve dilution if the sample is a biological fluid, fractionation if the sample is derived from a tissue or organ, or other standard preparation procedures which are known in the art. Thus, "biological sample" refers to the sample actually used in the assay which is derived from a fluid, cell, tissue or organ of a subject and prepared for use in the assay using the standard techniques. Normally, plasma or serum is the source of biological sample in these assays.

The assays may be conducted in a competition format employing a specific binding partner for the epitope-bearing portion. As used herein, "specific binding partner" refers to a substance which is capable of specific binding to a targeted substance, such as the epitope-bearing portion of the 170 kD subunit. In general, such a specific binding partner will be an antibody, but any alterative substance capable of such specific binding, such as a receptor, enzyme or arbitrarily designed chemical compound might also be used. In such contexts, "antibody" refers not only to immunoglobulin per se, but also to fragments of immunoglobulin which retain the immunospecificity of the complete molecule. Examples of such fragments are well known in the art, and include, for example, Fab, Fab', and F(ab')$_2$ fragments. The term "antibody" also includes not only native forms of immunoglobulin, but forms of the immunoglobulin which have been modified, as techniques become available in the art, to confer desired properties without altering the immunospecificity. For example, the formation of chimeric antibodies derived from two species is becoming more practical. In short, "antibodies" refers to any component of or derived form of an immunoglobulin which retains the immunospecificity of the immunoglobulin per se.

A particularly useful form of specific binding reagents useful in the assay methods of the invention is as monoclonal antibodies. Three categories of monoclonal antibodies have been prepared to the 170 kD subunit. One category of antibody is immunospecific for epitopes "unique" to pathogenic forms. These antibodies are capable, therefore, of immunoreaction to a significant extent only with the pathogenic forms of the amoeba or to the 170 kD subunit of lectin isolated from pathogenic forms. A second set of monoclonal antibodies is immunoreactive with epitopes which are "unique" to nonpathogenic forms. Thus, these antibodies are immunoreactive to a substantial degree only with the nonpathogenic amoeba or their lectins and not to the pathogenic forms. A third category of monoclonal antibodies is immunoreactive with epitopes common to pathogenic and nonpathogenic forms and these antibodies are capable of immunoreaction with the subunit or with the amoeba regardless of pathogenicity.

With respect to the monoclonal antibodies described herein, those immunoreactive with epitopes 1 and 2 of the 170 kD subunit isolated from the pathogenic-strain exemplified are capable of reacting, also, with the corresponding epitopes on nonpathogens. On the other hand, those immunoreactive with epitopes 3–6 are capable of immunoreaction only with the 170 kD subunit of pathogenic strains. By applying the techniques for isolation of the pathogenic 170 kD subunit to amoeba which are nonpathogenic, a 170 kD subunit can be obtained for immunization protocols which permit the analogous preparation of MAbs immunoreactive with counterpart epitopes 3–6 in the nonpathogenic forms.

Of course, with respect to antibodies found in the biological sample, in general, these will be found in the form of immunoglobulins. However, pretreatment of the sample with an enzyme, for example, to remove the $F_C$ portions of the antibodies contained therein, does not debilitate the sample with respect to its ability to respond to the assay.

ASSAY PROCEDURE

For the conduct of the assays of the invention, in general, the biological sample is contacted with the epitope-bearing portion used as an antigen in the immunoassay. The presence, absence or amount of the resulting complex formed between any antibody present in the sample and the epitope-bearing portion is measured directly or competitively.

As is well understood in the art, once the biological sample is prepared, there is a multiplicity of alternative protocols for conduct of the actual assay. In one rather straightforward protocol, the epitope-bearing portion provided as antigen may be coupled to a solid support, either by adsorption or by covalent linkage, and treated with the biological sample. The ability of any antibodies in the sample to bind to coupled antigen is then determined.

This ability may be determined in a "direct" form of the assay in which the level of complex formation by the antibody is measured directly. In one particularly convenient format of this approach, the antigen may be supplied as a band on a polyvinylidene difluoride (PVDF) and contacted with the biological sample; any resulting complexes formed with antibody on the PVDF membrane are then detected as described above for Western blot procedure. This protocol is substantially a Western Blot procedure. Alternatively, microtiter plates or other suitable solid supports may be used. The binding of antibody to the antigen coupled to support can then be detected as described above for Western blot procedure using conventional techniques generally involving secondary labeling using, for example, antibodies to the species from which the biological sample is derived. Such labels may include radioisotopes, fluorescent tags, enzyme labels and the like, as is conventionally understood.

The assay may also be formatted as a competition assay wherein the antigen coupled to solid support is treated not only with the biological sample but also with competing specific binding partner immunospecific for at least one epitope contained in the antigen. The competing binding partner is preferably an antibody. The competing antibody may be polyclonal or monoclonal and may itself be labeled or may be capable of being labeled in a secondary reaction. In a typical conduct of such a competitive test, a competitive specific binding partner for the antigen is generally supplied in labeled form and the success of the competition from the biological sample is measured as a reduction in the amount of label bound in the resulting complex or increased levels of label remaining in the supernatant. If monoclonal antibodies are used, the assay can readily be made specific for pathogenic or nonpathogenic reacting antibodies, if desired, by choosing antibodies of the appropriate specificity. Thus, if the assay is to be made specific for antibodies raised against pathogenic forms of E. histolytica, the competition will be provided by a monoclonal antibody specific for an epitope characteristic of pathogenic strains.

Another manner in which the assay may be made specific for pathogenic or nonpathogenic forms is in the choice of the epitope-bearing portion. If antibodies specific to the pathogens are to be detected, an epitope-bearing portion is chosen which bears only epitopes characteristic of pathogenic strains. Conversely, antibodies immunospecific for nonpathogens can be conducted by utilizing as antigen only portions of the subunit which contain epitopes characteristic of nonpathogens. Where characterization as pathogen or nonpathogen-specific antibodies is unnecessary, antigen containing both such epitopes or epitopes shared by both forms may be used.

Additional ways to distinguish between antibodies immunospecific for pathogens and for nonpathogens employ competition assays with monoclonal antibodies of such specificities, as described above.

Alternatively, the biological sample can be coupled to solid support and the desired epitope-bearing portion added under conditions where a complex can be formed to the epitope-bearing portion, which is then used to treat the support. Subsequent treatment of the support with antibodies known to immunoreact with the antigen can then be used to detect whether antigen has been bound.

Thus, the biological sample to be tested is contacted with the epitope-bearing portion, which is derived either from a pathogenic or nonpathogenic from one both of E. histolytica so that a complex is formed. The complex is then detected by suitable labeling, either by supplying the antigen in labeled from, or by a secondary labeling process which forms a ternary complex. The reaction is preferably conducted using a solid phase to detect the formation of the complex attached to solid support, or the complex can be precipitated using conventional precipitating agents such as polyethylene glycol.

In a more complex form of the assay, competitive assays, can be used wherein the biological sample, preferably serum or plasma, provides the cold antibody to compete with a specific binding partner, such as a labeled monoclonal antibody preparation known to bind specifically to an epitope unique to the Gal/GalNAc lectin or its 170 kD subunit of a pathogenic or nonpathogenic from. In this embodiment, the binding to labeled specific monoclonal antibody is conducted in the presence and absence of biological sample, and the diminution of labeling of the resulting complex in the presence of sample is used as an index to determine the level of competing antibody.

Kits suitable for the conduct of these methods include the appropriate labeled antigen or antibody reagents and instructions for conducting the test. The kit may include the antigen coupled to solid support as well as additional reagents.

METHODS OF PROTECTION AND VACCINES

The recombinant 170 kD subunit or an epitope-bearing portion thereof may be used as active ingredient. Preferred regions include positions 482–1138, 596–1138, 885–998, 1033–1082 and 1082–1138.

The 170 kD subunit or its epitope-bearing regions may also be produced recombinantly in procaryotic cells for the formulation of vaccines. The recombinantly produced 170 kD protein or an epitope-bearing region thereof can be used as an active ingredient in vaccines for prevention of *E. histolytica* infection in subjects who are risk for such condition. Sufficiently large portions of the 170 kD protein can be used per se; if only small regions of the molecules for example containing 20 amino acids or less or to be used, it may advantageous to couple the peptide to a neutral carrier to enhance its immunogenicity. Such coupling techniques are well known in the art, and include standard chemical coupling techniques optionally effected through linker moieties such as those available from Pierce Chemical Company, Rockford, Ill. Suitable carriers may include, for example, keyhole limpid hemocyanin (KLH) *E. coli* pilin protein k99, BSA, or the VP6 protein of rotavirus. Another approach employs production of fusion proteins which include the epitope-bearing regions fused to additional amino acid sequence. In addition, because of the ease with which recombinant materials can be manipulated, the epitope-bearing region may be included in multiple copies in a single molecule, or several epitope-bearing regions can be "mixed and matched" in a single molecule.

The active ingredient, or mixture of active ingredients, in the vaccine is formulated using standard formulation for administration of proteins or peptides and the compositions may include an immunostimulant or adjuvant such as complete Freund's adjuvant, aluminum hydroxide, liposomes, ISCOMs, and the like. General methods to prepare vaccines are described in *Remingtons's Pharmaceutical Science;* Mack Publishing Company Easton, Pa. (latest edition). The compositions contain an effective amount of the active ingredient peptide or peptides together with a suitable amount of carrier vehicle, including, if desired, preservatives, buffers, and the like. Other descriptions of vaccine formulations are found in "New Trends and Developments in Vaccines", Voller, A., et al., University Park Press, Baltimore, Md. (1978).

The vaccines are administered as is generally understood in the art. Ordinarily, administration is systemic through injection; however, other effective means of administration are included. With suitable formulation, for example, peptide vaccines may be administered across the mucus membrane using penetrants such as bile salts or fusidic acids in combination, usually, with a surfactant. Transcutaneous means for administering peptides are also known. Oral formulations can also be used. Dosage levels depend on the mode of administration, the nature of the subject, and the nature of carrier/adjuvant formulation. Typical amounts of protein are in the range of 0.01 $\mu$g–1 mg/kg. However, this is an arbitrary range which is highly dependent on the factors cited above. In general, multiple administrations in standard immunization protocols are preferred; such protocols are standard in the art.

A preferred epitope-bearing region of the 170 kD subunit is that represented by amino acids 482–1138 which includes the cysteine-rich domain. This region is encoded by nucleotides 1492–3460 shown in FIGS. 1A-1 to 1A-5V herein. Preferred regions include those bearing epitopes which are specific for antibodies against pathogenic amoeba—i.e., regions 1082–1138 and 1032–1082. However, the epitope-bearing region at positions 894–998 may also be used. For regions of this length, production of peptides with multiple copies of the epitope-bearing regions is particularly advantageous.

Production of Recombinant Epitope-bearing Portions

The epitope-bearing portions of the 170 kD subunit can be conveniently prepared in a variety of procaryotic systems using control sequences and hosts ordinarily available in the art. The portions may be provided as fusion proteins or as mature proteins and may be produced intracellularly or secreted. Techniques for constructing expression systems to effect all of these outcomes is well understood in the art. If the epitope-bearing portion is secreted, the medium can be used directly in the assay to provide the antigen, or the antigen can be recovered from the medium and further purified if desired. If the protein is produced intracellularly, lysates of cultured cells may be used directly or the protein may be recovered and further purified. In the Examples below, the epitope-bearing portion is provided as a fusion protein using the commercially available expression vector pGEX. Alternative constructions and alternative hosts can also be used as is understood in the art.

Reagents and assays for a novel 170 kD lectin subunit p To determine the existence and complexity of the 170 kDa subunit gene family, hgl, an amebic genomic library in lambda phage was hybridized with DNA fragments from the 5' or 3' ends of hgl1. Termini from three distinct heavy subunit genes were identified including hgl1, hgl2, and a third, unreported gene designated hgl3. The open reading frame of hgl3 was sequenced in its entirety FIGS. 4A–4F (SEQ ID NO:4 and (SEQ ID NO:5). Nonstringent hybridization of a genomic Southern blot with heavy subunit specific DNA labeled only those bands predicted by hgl1–3. The amino acid sequence of hgl3 (FIG. 4B) was 95.2% identical to hgl1 and 89.4% identical to hgl2. All 97 cysteine residues present in the heavy subunit were conserved in hgl1–3. Analysis of amebic RNA showed that all three heavy subunit genes were expressed in the amebae and that hgl message became less abundant as the amebae entered a stationary growth phase.

Accordingly, the present invention provides both nucleic acid and immunological reagents specific for 170 kDa subunits encoded by each of the hgl1, hgl2 or hgl3 genes, as well as reagents which detect common regions of all three hgl genes and their nucleic acid or protein products. For example, oligonucleotide probes specific for any one of these three genes may be identified by one of ordinary skill in the art, using conventional nucleic acid probe design principles, by comparisons of the three DNA sequences for these genes, which sequences are disclosed in FIGS. 1A-1 to 1A-6 (SEQ ID NO:1) and FIGS. 4A–4F (SEQ ID NO:4) for hgl1 and hgl3, respectively, and for hgl2, in Tannich, E. et al. *Proc Natl Acad Sci USA* (1991) 88:1849–1853, the entire disclosure of which is hereby incorporated herein by reference. Example 6 illustrates the use of oligonucleotide probes specific for each of the three hgl genes, for determining the level of expression of RNA from each gene using Northern blot analyses. Other methods of using hgl-specific nucleic acids for diagnostic purposes, for pathogenic and/or non-pathogenic forms of *E. histolytica*, are described in U.S. Pat. No. 5,260,429, the entire disclosure of which is incorporated herein by reference.

The following Examples are intended to illustrate but not to limit the invention.

EXAMPLE 1

Construction of Expression Vectors

The 170 kD subunit of the galactose lectin is encoded by at least two genes. The DNA used for all of the constructions described h n encodes the 170 kD lectin designated hgl1

(FIGS. 1A-1 to 1A-6 (SEQ ID NO:1)). The nucleotide position designations refer to the numbering in FIG. 1A.

The DNA sequence encoding hgll was expressed in three portions:

fragment C (nucleotides 46–1833) included the cysteine- and tryptophan-rich region, the cysteine-free region, and 277 amino acids of the cysteine-rich domain, i.e. amino acid residues 2–596;

fragment A (nucleotides 1492–3460) encoded the majority of the cysteine-rich domain, i.e. amino acid residues 482–1138;

fragment B (3461–3892) included 70 amino acids of the cysteine-rich domain, the putative membrane-spanning region, and the cytoplasmic tail, i.e. amino acid residues 1139–1276.

Figure 2B:
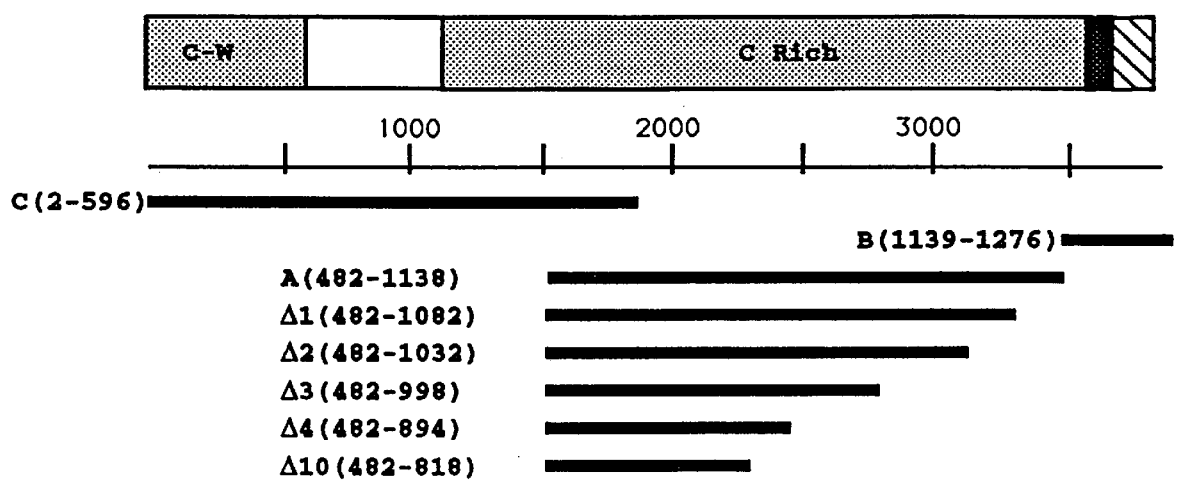
FIG. 2B shows the pattern of deletion mutants.

See FIG. 2B.

Each of these three fragments was inserted in frame by ligation into pGEX2T or pGEX3X to obtain these proteins as GST fusions. A diagram of the vectors constructed is shown in FIG. 2A.

Fragment C was produced by PCR amplification. Primers were designed so that a BamHI site was added to the 5' end and an EcoRI site was added to the 3' end during the PCR process. The PCR product, fragment C, was then digested with restriction enzymes BamrI and EcoRI, purified, and ligated into similarly digested pGEX3X. Fragments A and B were produced by digestion with EcoRI from plasmid clones (Mann, BJ et al. *Proc Natl Acad Sci USA* (1991) 88:3248–3252) and ligated into pGEX2T that had been digested with EcoRI. In the PGEX expression system a recombinant protein is expressed as a fusion protein with glutathione S-transferase (GST) from *Schistosoma japonicum* and is under the control of the tac promoter. The tac promoter is inducible by IPTG. The construction of the vectors and subsequent expression is further described in Mann, BJ et al. *Infec and Immun* (1993) 61:1772–1778, referenced above, and incorporated herein by reference.

Expression in the correct reading frame was verified for all constructs by sequencing and Western immunoblot analysis by testing for reactivity with anti-adhesion antisera (data not shown). Expression of the hgll fusion proteins was shown to be inducible by IPTG. The GST protein produced from the original pGEX2T did not react with the anti-adhesion sera. The GST portion of the fusion protein has a molecular mass of 27.5 kD.

EXAMPLE 2

Production of Recombinant Protein

The four vectors described above, as well as the host vector were transfected into competent *E. coli* hosts and expression of the genes encoding the fusion proteins was effected by induction with IPTG. Production of the fusion proteins was determined by Western blot SDS-PAGE analysis of the lysates.

EXAMPLE 3

Reactivity of Recombinant 170 kD Subunit Fusion Proteins with MAbs

Induced cultures containing bacterial strains expressing hgl1 fragment A, B, or C were harvested, lysed in sample buffer, and applied to an SDS-polyacrylamide gel. After electrophoresis, the proteins were transferred to Immobilon and incubated with anti-170-kD Mabs, specific for seven different epitopes. Characteristics of the individual MAbs are shown in Table 1. It will be noted that all the known epitopes are in the region of amino acids 596–1138.

TABLE 1

Characteristics of monoclonal antibodies directed against the galactose adhesion 170 kD subunit

| Epitope # | Designation | Isotype[1] | Adherence[1] | Cytotoxicity[2] | C5b9 Resistance[3] | P[4] | NP[4] | Location[5] |
|---|---|---|---|---|---|---|---|---|
| 1 | 3F4 | IgG$_1$ | Increases | Decreases | No effect | + | + | 895–998 |
| 2 | 8A3 | IgG$_1$ | Increases | No effect | Decreases | + | + | 895–998 |
| 3 | 7F4 | IgG$_{2b}$ | No effect | No effect | Decreases | + | – | 1082–1138 |
| 4 | 8C12 | IgG$_1$ | Inhibits | Inhibits | Decreases | + | – | 895–998 |
| 5 | 1G7 | IgG$_{2b}$ | Inhibits | Inhibits | Decreases | + | – | 596–818 |
| 6 | H85 | IgG$_{2b}$ | Inhibits[6] | Inhibits | Blocks | + | – | 1033–1082 |
| 7 | 3D12 | IgG$_1$ | No effect | Not tested | Blocks | + |  | 895–998 |

[1]Adherence was assayed by the binding of Chinese hamster ovary (CHO) cells to *E. histolytica* trophozoites and by binding of $^{125}$I labeled purified colonic mucins to trophozoites. Petri, W.A. Jr., et al., J Immunol (1990) 144:4803–4809.
[2]The assay for cytotoxicity was CHO cell killing by *E. histolytica* trophozoites as measured by $^{51}$Cr release from labeled CHO cells. Saffer, L.D., et al. Infect Immun (1991) 59:4681–4683.
[3]C5b9 resistance was assayed by the addition of purified complement components to *E. histolytica* trophozoites. The percent of amebic lysis was determined microscopically. Braga, L.L., et al. J Clin Invest (1992) 90:1131–1137.
[4]P and NP refer to reactivity of the MAb with pathogenic (P) and nonpathogenic (NP) species of *E. histolytica* as determined in an Elisa assay. Petri, W.A. Jr., et al. Infect Immun (1991) 58: 1802–1806.
[5]Location of antibody binding site by amino acid number. Results presented herein.
[6]Inhibits adherence to CHO cells but not human colonic mucin glycoproteins. Petri, W.A. Jr., et al., J Immunol (1990) 144:4803–4809.

Fusion proteins B and C failed to react with any of the seven MAbs (data not shown). Fusion protein A, representing positions 482–1132, reacted with all seven MAbs representing all 7 epitopes and not a negative control developed with an irrelevant MAb, MOPC21. The MAbs were used at 10 μg/ml and polyclonal antibodies at 1:1000 dilution. These results indicated that these seven epitopes were contained within the 542 amino acids of the cysteine-rich extracellular domain of the 170 kD subunit.

The generation of 3' deletions by controlled ExoIII digestion of fragment A of the 170 kD subunit is outlined in FIG. 2B. Δ1 contains amino acid residues 482–1082; Δ2 contains amino acid residues 482–1032; Δ3 contains amino acid residues 482–998. The reactivities of the fusion proteins that include fragment A or either of two carboxy-terminal deletions (Δ3 and Δ4) with the seven distinct 170 kD-specific MAbs were determined. Deletion 3 reacted with MAb against epitopes 1–2, 4–5, and 7 but failed to react with MAbs recognizing epitopes 3 and 6; Deletion 4 which contains residues 498–894 reacted only with the MAb which recognizes epitope 5.

Figure 3:
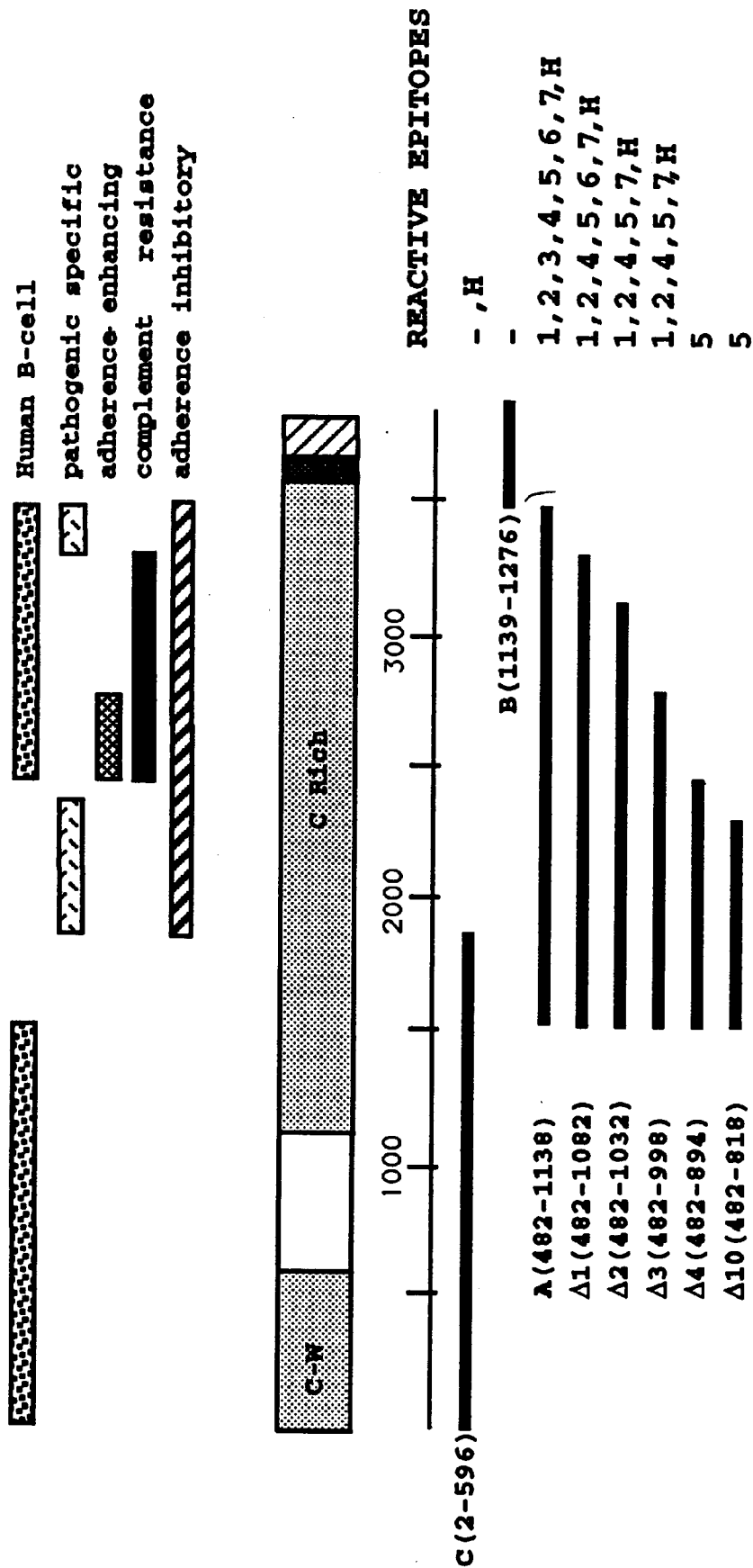
Figure 6:
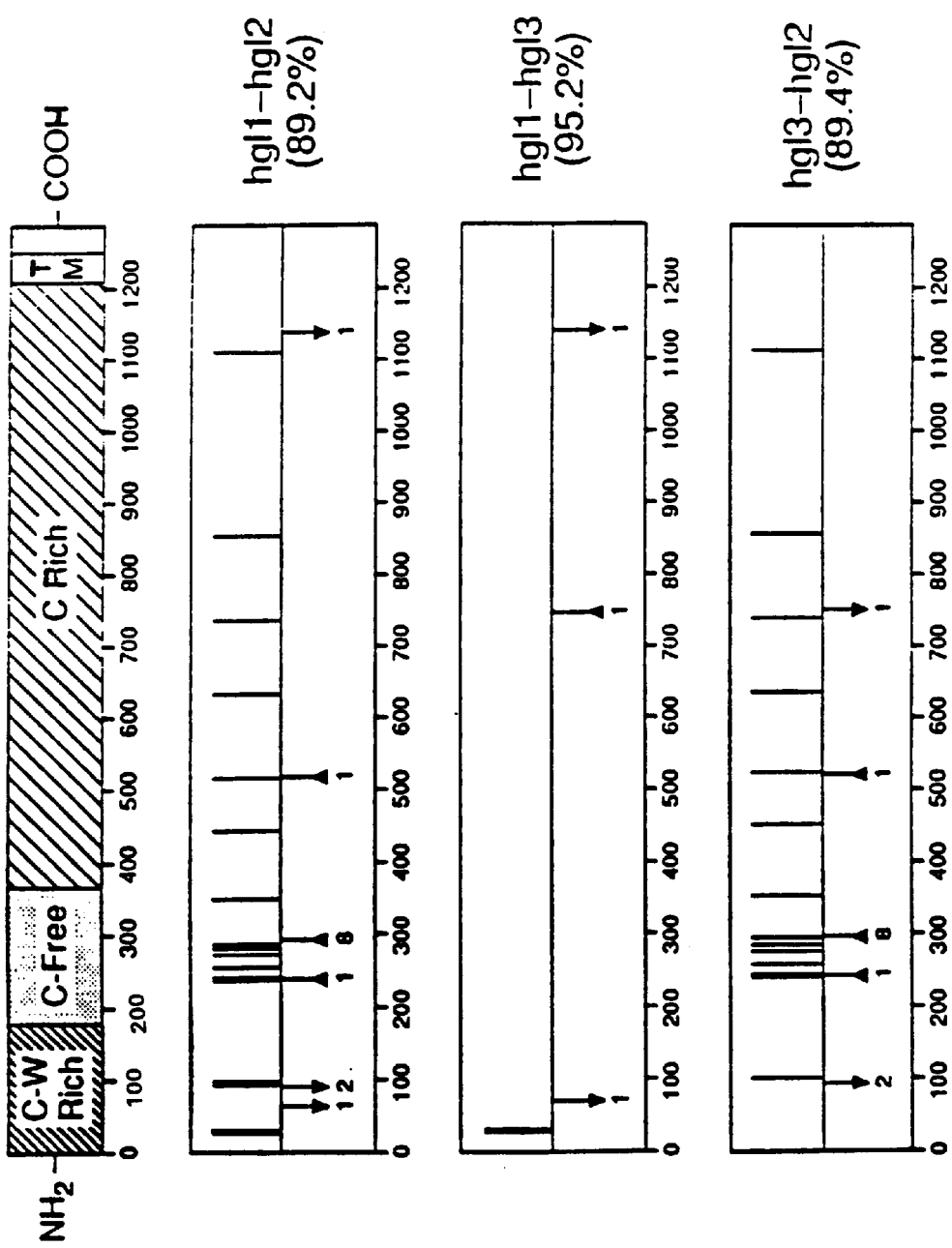
FIG. 6 shows in schematic form a comparison of amino acid sequences of three heavy subunit genes. The top diagram represents a schematic representation of a heavy subunit gene. Starting at the amino terminus, regions include the cysteine/tryptophan (C-W) rich domain, the cysteine-free (C-free) domain, the cysteine-rich (C-rich) domain, and the putative transmembrane (TM) sequence and cytosolic domains (Mann, B. J. et al. *Parasit Today* (1991) 7:173–176). Amino acid sequence comparisons of hgl1, hql2 and hgl3 are shown. Upright lines indicate nonconservative amino acid substitutions in the amino acid sequence of the second gene as compared to the first gene listed to the right. Downward arrowheads indicate a deletion while upright arrowheads indicate an insertion. The number of residues inserted or deleted are listed below the arrowheads and the total percent amino acid sequence identity is listed at right.

The five deletion derivatives of fusion protein A shown in FIG. 2B, ranging in estimated size from 35 to 68 kD, were tested for reactivity to each MAb, and the reactivities of the deletions with each MAb are summarized in FIG. 3. The endpoints of the various deletions were determined by DNA sequencing with primers specific for the remaining hgl1 sequence. MAbs recognizing epitopes 1 and 2, which increase amebic adherence to target cells, failed to react with recombinant lectin fusion proteins lacking amino acids 895 to 998. Similarly, MAbs recognizing epitope 4, an inhibitory epitope, and epitope 7, which has the effect of abrogating amebic lysis by complement, failed to react with deletion mutants lacking this region. The MAb specific for epitope 6, which has inhibitory effects on amebic adherence and abrogates amebic lysis by complement, did not react with a recombinant protein missing amino acids 1033 to 1082. Recombinant proteins lacking amino acids 1082 to 1138 did not react with a MAb which is specific for the neutral epitope 3. Finally, a construct containing amino acids 482 to 818 was recognized only by the adherence-inhibitory epitope 5 MAb. The thus predicted locations of the MAb epitopes are listed in Table 1 above.

EXAMPLE 4

Reactivity of 170 kD Fusion Proteins with Human Immune Sera

Since the galactose adhesion is a major target of the humoral immune response in the majority of immune individuals, the mapping of human B-cell epitopes of the 170 kD subunit was undertaken. The recombinant fusion proteins and ExoIII-generated deletion constructs of the 170 kD subunit were tested for reactivity with pooled human immune sera in the same manner as described for MAb reactivity. Nonimmune sera was used as a control. Fusion proteins A and C reacted with immune sera, whereas fusion protein B did not (data not shown). Human immune sera also reacted with deletion constructs Δ1, Δ2, and Δ3 but not with Δ4 or Δ10. Reactivity of immune sera with the different deletions localized major human B-cell epitopes to be within the first 482 amino acids and between amino acids 895 and 1138 (FIG. 3). This second region is the same area which contains six of the MAb epitopes. These results are consistent with a report by Zhang et al. supra, who found that sera from immune individuals reacted primarily with recombinant adhesion constructs containing amino acids 1 to 373 and 649 to 1202.

Thus, for use in assays to detect human antisera against *E. histolytica,* the useful epitope-bearing portions are as shown in Table 2.

TABLE 2

| Positions | Epitope # | P/NP |
|---|---|---|
| 2–482 | ? | ? |
| 1082–1138 | 3 | P |
| 1033–1082 | 6 | P |
| 895–998 | 1,2,4,7 | both |

The epitope-bearing portions indicated can be used alone, as fragments or as portions of chimeric or fusion proteins, or any combination of these epitope-bearing portions can be used.

EXAMPLE 5

Immunization Using Recombinant Subunit Protein

A GST fusion protein with fragment A was prepared in *E. coli* as described in Example 1 above. This peptide contains an upstream GST derived peptide sequence followed by and fused to amino acids 432–1138 encoded by nucleotides 1492–3460 in FIGS. 1A-1 to 1A6 (SEQ ID NO:1) herein. The protein is produced intracellularly; the cells were harvested and lysed and the lysates subjected to standard purification techniques to obtain the purified fusion protein.

Gerbils were immunized by intraperitoneal injection with 30 μg of purified fusion protein in complete Freund's adjuvant and then boosted at 2–4 weeks with 30 μg of the fusion protein in incomplete Freund's adjuvant.

The gerbils were challenged at 6 weeks by intrahepatic injection of $5\times10^5$ amebic trophozoites and sacrificed 8 weeks later. The presence and size of amoebic liver abscesses was determined.

The results of the two experiments described above are shown in the tables below. The administration of the fusion protein reduced the size of abscesses in a statistically significant manner.

In experiment 1, six animals were used as controls and nine were administered the fusion protein; in experiment 2, seven animals were used as controls and seven were provided the fusion protein.

| | Experiment 1 | | Experiment 2 | |
|---|---|---|---|---|
| | Abscess Weight | % with Abscess | Abscess Weight | % with Abscess |
| Control | 1.44 ± 1.64 | 71% | 4.76 ± 1.78 | 100% |
| GST - (482–1138) | 0.81 ± 0.10* | 100% | 2.35 ± 1.99 | 100% |

*P < 0.03 compared to control.
+P < 0.24 compared to control.

EXAMPLE 6

Analysis of the Gene Family Encoding the 170 kD Subunit of *E. histolytica* Gal/GalNAc Adherence Lectin This Example shows that the adhesin 170 kDa subunit of HM-1:IMSS strain *E. histolytica* is encoded by a gene family that includes hgl1, hgl2 and a previously undescribed third gene herein designated hgl3. Since hgl1 and hgl2 were originally sequenced, in part, from different cDNA libraries, it was possible that they represented strain differences of a single gene. However, in this report both 5' and 3' termini of hgl1, hgl2, and hgl3 were isolated and sequenced from the same lambda genomic library demonstrating unambiguously that hgl is a gene family.

The Nortern data indicated that all three genes were expressed in the amebae. As the messages of hgl1–3 are predicted to comigrate at 4.0 k.b, differential hybridization was required to ascertain expression of individual genes. Due to the high degree of identity between hgl1–3, relatively short oligonucleotides (17–21 bases) were synthesized specific for regions where the three genes diverge. Each probe was compated by computer analysis to the other hgl genes to be certain that they were sufficiently divergent to prevent cross highly stringent for such A/T rich probes and were done at temperatures 5° C. or less below the predicted Tm based upon nearest neighbor analysis. While it is impossible to rule out cross hybridization with other hgl gene members, these precautions make such an event less likely.

The Northern blot also indicates that abundance of mRNA for all three genes decreased as the amebae progressed from log to stationary growth. This finding correlates with data which indicates that late log and stationary phase amebae have a decreased ability to adhere to, lyse, and phagocytose target cells (Orozco, E. et al. (1998) "The role of phagocytosis in the pathogenic mechanism of Entamoeba histolytica. In: *Amebiasis: Human infection by Entamoeba histolytica* (Ravdin J.I., ed), pp. 326–33. John Wiley & Sons, Inc., New York.

Details of the experimental methods and results of the characterization of the hgl multigene family are presented below.

*Library Screen.* A lambda Zap® II library containing randomly sheared 4–5 kb fragments of genomic DNA from HM-1:IMSS strain *E. histolytica* was kindly provided by Dr. J. Samuelson at Harvard University (Kumar, A. et al. *Proc Natl Acad Sci USA* (1992) 89:10188–10192). Over 80,000 plaques from the library were screened on a lawn of XL-1 Blue *E. coli* (Strategene, La Jolla, Calif.). Duplicate plaque lifts, using Hybond-N membranes (Amersham, Arlington Heights, Ill.), were placed in a prehybridization solution consisting of 6×SSC (0.89 M sodium chloride and 90 mM sodium citrate), 5×Denhardts solution, 0.5% SDS, 50 mM $NaPO_4$ (pH 6.7), and 100 μg/ml salmon sperm DNA for minimum of 4 hours at 55° C. A 5'and 3'DNA fragment of hgl1 (nucleotides 106–1946 and 3522–3940 respectively) were [$\alpha$-$^{32}$P]dCTP (Amersham) labeled using the Random Prime DNA labeling Kit according to the manufacturer's instructions (Boehringer Mannheim, Mannheim, Germany) and hybridized seperately to the membranes overnight at 55° C. in prehybridization solution. Membranes were rinsed once and washed once for 15 minutes at room temperature in 2×SSC, 0.1% SDS, then washed once for 15 minutes at room temperature, and twice at 55° C. for 20 minutes in 0.1% SDS, then washed once for 15 minutes at room temperature, and twice at 55° C. for 20 minutes in 0.1×SSC, 0.1% SDS. Plaques that hybridized with the 5' or the 3 radiolabeled probe on both duplicate filters were isolated and purified.

Northern blot and hybridization. Total RNA was harvested from amebae using the guanidinium isothiocyanate method (RNagen, Promega, Madison, Wis.). Polyadenylated RNA was purified from total RNA using PolyATract System 1000 (Promega). RNA was electrophoresed through a formaldehyde gel and transferred to a nylon Zetabind membrane (Cuno) using 25 mM phosphate buffer (pH 7.5) as described (Sambrook, J. et al. (1989) *Molecular Cloning: A laboratory manual,* Cold Spring Harbor Laboratory Press, Cold Spring Harbor, N.Y.). The membrane was incubated in prehybridization solution and incubated at 37° C. for at least two hours. Oligonucleotides (18–22 nucleotides long) were end-labeled using polynucleotide kinase and [$\gamma$-$P^{32}$]ATP (Sambrook, J. et al. (1989) *Molecular Cloning: A laboratory manual,* Cold Spring Harbor Laboratory Press, Cold Spring Harbor, N.Y.), added to the hybridization mixture and the membrane, and incubated at 37° C. overnight. The membrane was then washed once at room temperature for 10 minutes, once at 37° C. for 10 minutes; and twice at 40–44° C. for 15 minutes each in 2×SSC, 0.1% SDS. The radiolabeled probes used were:

5'-TTTGTCACTATTTTCTAC-3'(SEQ ID NO:7) hgl1;
5'-TATCTCCATTTGGTTGA- 3' (SEQ ID NO:8) hgl2;
5'-TTTGTCACTATTTTCTAC-3'(SEQ ID NO:9), hgl3; and 5'-CCCAAGCATATTTGAATG-3'(SEQ ID NO:10), EF-1α (Plaimauer, B. et al. *DNA Cell Biol* (1993) 12:89–96).

Characterization of the hgl3 gene. The hgl3 open reading frame was 3876 bases and would result in a predicted translation product of 1292 amino acids (FIG. 4). The predicted translation products of hgl1 and hgl2 would be 1291 and 1285 amino acids respectively. A putative signal sequence and a transmembrane domain were identified in the amino acid sequence of hgl3 similar to hgl1 and hgl2. The amino-terminal amino acid sequence of the mature hgl3 protein, determined by Edman degradation (Mann, B. J. et al. *Proc Natl Acad Sci USA* (1991) 88:3248–3252), was assigned residue number 1. Previous analysis of hgl1 and hgl2 identified a large, conserved, extracellular region which was 11% cysteine, designated the cysteine-rich domain (Mann, B. J. et al. *Parasit Today* (1991) 7:173–176) (FIG. 2). Sequence analysis of hgl3 revealed that all 97 cysteine residues present within this region were also conserved in both of the previously reported heavy subunit genes.

A schematic comparison (FIG. 6) of heavy subunit gene sequences revealed a high degree of amino acid sequence identity. However, seven sites, ranging from 3–24 nucleotides, were found where an insertion or deletion had occurred in one subunit relative to another, all of which maintained the open reading frame. Both hgl1 and hgl3 contained a large number of nonconservative amino acid substitutions when compared to hgl2, making them 89.2% and 89.4% identical to hgl2 respectively. While the comparison of hgl1 and hgl3 revealed only two nonconservative substitutions, 57 conservative amino acid substitutions and 3 single residue insertion/deletions making them 95.2% identical.

All 16 potential sites of glycosylation present in hgl1 were conserved in hgl3. A sequence analysis of hgl2 indicated that it contained only 9 such sites, although all 9 were present in hgl1 and hgl3. Glycosylation appears to account for approximately 6% of the heavy subunits' apparent molecular mass (Mann, B. J. et al. *Proc Natl Acad Sci USA* (1991) 88:3248–3252).

All three heavy subunits are expressed. Since hgl3 was isolated from a genomic library, it was unknown if this gene was transcribed. Polyadenylated RNA was harvested from amebae in both log and stationary phase growth. Probes specific for hgl1, hgl2, or hgl3 were hybridized to a Northern blot and identified an RNA band of the predicted size of 4.0 kb.

As the messages of hgl1–3 are predicted to comigrate at 4.0 kb, differential hybridization was required to ascertain expression of individual genes using Northern blots. Due to the high degree of identity between hgl1–3, relatively short oligonucleotides (17–21 bases) were synthesized specific for regions where the three genes diverge. Each probe was compared by computer analysis to the other hgl genes to be certain that they were sufficiently divergent to prevent cross hybridization. Hybridization and wash conditions were highly stringent for such A/T rich probes and were done at temperatures 5° C. or less below the predicted Tm based upon nearest neighbor analysis. While it is impossible to rule out cross hybridization with other hgl gene members, these precautions make such an event less likely.

The message abundance decreased significantly as the amebic trophozoites passed from log phase growth (lane A) to stationary phase growth (lane B) while the control gene, EF-1α, either remained constant or increased slightly. This finding correlates with data indicating that late log and stationary phase amebae have a decreased ability to adhere to, lyse, and phagocytose target cells (Orozco, E. et al. (1988) "The role of phagocytosis in the pathogenic mechanism of *Entamoeba histolytica*. In: *Amebiasis: Human infection by Entamoeba histolytica* (Ravdin J. I., ed), pp. 326–338. John Wiley & Sons, Inc., New York.

Estimation of the number of heavy subunit genes. The observations herein confirm that the adhesin 170 kDa subunit of HM-1:IMSS strain *E. histolytica* is encoded by a gene family that includes hgl1, hgl2 and a previously undescribed third gene which is designated hgl3. Since hgl1 and hgl2 were originally sequenced, in part, from different cDNA libraries, it was possible that they represented strain differences of a single gene. However, in the present work both 5' and 3' termini of hgl1, hgl2, and hgl3 were isolated and sequenced from the same lambda genomic library, demonstrating unambiguously that hgl is a gene family.

Comparison of the amino acid sequences of the three heavy subunit genes found that hgl1 and hgl2 are 89.2% identical, hgl1 and hgl3 are 95.2% identical, and hgl2 and hgl3 are 89.4% identical. Sequence variation within the gene family, however, appears to be nonrandomly distributed within the coding sequence. The majority of the nonconservative amino acid substitutions as well as insertions and deletions occur in the amino third of the molecule. Comparison of the amino acid sequences of hgl2 and hgl3 reveal that 11 of the 19 nonconservative amino acid substitutions and 11 of the 13 residues inserted or deleted reside within the first 400 amino acid residues. A similar pattern of variation is present when hgl1 and hgl2 are compared. While hgl1 and hgl3 contain only two nonconservative substitutions, both are found within the first 400 residues although the 57 conservative substitutions appear to be more randomly distributed throughout the coding sequence. The high degree of sequence conservation between hgl3 and hgl1 suggest that they may have arisen from a recent gene duplication event.

All 97 cysteine residues were maintained in the three heavy subunit genes. The hgl2 gene was originally reported lacking a single cysteine present in both hgl1 and hgl3. However, this discrepancy has since been recognized as a sequencing error (Dr. E. Tannich, Bernhard Nocht Institute, Hamburg, Germany, personal communication). The cysteine residues are nonrandomly distributed throughout the gene (FIG. 1) with the highest concentration within the cysteine-rich domain between amino acid residues 379–1210. All seven identified epitopes recognized by murine monoclonal antibodies map to this region (Mann, B. J. et al. *Infect Immun* (1993) 61:1772–1778). As these monoclonal antibodies can block target cell adhesion, target cell lysis (Saffer, L. D. et al. *Infect Immun* (1991) 59:4681–4683), and/or resistance to host complement-mediated lysis (Braga, L. L. et al. *J Clin Invest* (1992) 90:1131–1137), the conservation of cysteine residues may play an important role in maintaining the conformation of this important region of hgl.

A minimum of three genes have been shown to make up the heavy subunit gene family, as described herein. While it is not possible to rule out the existence of additional hgl genes, Southern blot analyses and library screen data can best be explained by a gene family of three members. For Southern blots, two restriction enzymes were identified, DdeI and HindIII, that cut genomic DNA to completion and resulted in analyzable restriction fragments. As the membrane was hybridized with a fragment of hgl1 corresponding to nucleotides 1556 to 3522, two bands of >976 and 1965 nucleotides should have been present from hgl3. This central hgl1 radioprobe would hybridize with three bands of 1158, 810 and >1080 nucleotides from hgl1 and would hyribidze with five bands of 819, 312, 55, 755, and >1080 nucleotides from hgl2. The Southern blot showed 7 bands for genomic DNA disgested with DdeI, at 4200, 3700, 2100, 1800, 1300, 840, and 760 nucleotides. As the 819 and 810 nucleotide bands would be expected to comigrate, all the bands observed with DdeI digestion are explained by the restriction maps of hgl1–3.

HindIII has no restriction sites in hgl1–3 within the coding region and would result in each gene being represented by a single band greater than 4.0 kb. The Southern blot showed three bands at 17500, 5600, and 4200 nucleotides. Should an additional heavy subunit gene exist, its DdeI and HindIII fragments would need to comigrate with hgl1–3 bands, be so divergent that they failed to hybridize with the hgl1 probe under very low stringency, or be too large to be resolved and transferred.

As to the genomic screening data, the genomic library was screened separately with a 5' and a 3' hgl specific probe, additional heavy subunit genes would be isolated even if they contained only partial identity with the gene family at only one end or even if one termini of an additional gene had been lost during library amplification. The library screen looked at more than $3.2 \times 10^8$ bases of genomic DNA in an organism with an estimated genome size of 1075 bases (Gelderman, A. H. et al. *J Parasitol* (1971) 57:906–911). Thus, a full genomic equivalent was screened at low stringency for genes containing identity at either end. Of 7 clones identified with the 5' heavy subunit-specific probe, 4 contained inserts that matched the reported sequence for hgl1, 2 matched the sequence of hgl2, and 1 clone represented hgl3. Of eight clones obtained using the 3' radiolabeled fragment, 1 matched the sequence for hgl1, 5 matched the sequence of hgl2, and 2 represented hgl3. No termini were found that did not match the sequence of hgl1, hgl2 or hgl3.

We claim:

1. A vaccine composition for immunizing a subject against E. histolytica infection comprising a recombinant, nonglycosylated, epitope-bearing peptide of the 170 kD subunit of E. histolytica Gal/GalNac adherence lectin, which subunit is encoded by an hgl gene of any strain of E. histolytica, which peptide bears at least one epitope that reacts with antibodies made in a subject infected with E. histolytica or immunized with said adherence lectin or an epitope-bearing portion thereof, with the proviso that said peptide is not (i) the full length 170 kDa subunit, or (ii) amino acid sequence residues 480–1138 of SEQ ID NO:3.

2. The composition of claim 1 wherein said epitope-bearing peptide is encoded by hgl1.

3. The composition of claim 1 wherein said epitope-bearing peptide is encoded by hgl2.

4. The composition of claim 1 wherein said epitope-bearing peptide is encoded by hgl3.

5. The composition of claim 1 wherein the epitope-bearing peptide has an amino acid sequence selected from the group consisting of:

(a) Peptide I, residues 596–1138 of SEQ ID NO:3 or a corresponding peptide of a naturally occurring variant of said 170 kD subunit encoded by an hgl gene of any strain of E. histolytica;

(b) Peptide II, residues 895–998, of SEQ ID NO:3 or a corresponding peptide of a naturally occurring variant of said 170 kD subunit encoded by an hgl gene of any strain of E. histolytica, and (c) Peptide III, residues 1033–1082 of SEQ ID NO:3 or a corresponding peptide of a naturally occurring variant of said 170 kD subunit encoded by an hgl gene of any strain of E. histolytica.

6. The composition of claim 5 wherein said epitope-bearing peptide is Peptide I.

7. The composition of claim 5 wherein said epitope-bearing peptide is Peptide II.

8. The composition of claim 5 wherein said epitope-bearing peptide is Peptide III.

9. A method to immunize a subject against Entamoeba histolytica infection which method comprises administering to said subject an effective amount of the composition of claim 1.

10. A method to immunize a subject against Entamoeba histolytica infection which method comprises administering to said subject an effective amount of the composition of claim 2.

11. A method to immunize a subject against Entamoeba histolytica infection which method comprises administering to said subject an effective amount of the composition of claim 3.

12. A method to immunize a subject against Entamoeba histolytica infection which method comprises administering to said subject an effective amount of the composition of claim 4.

13. A method to immunize a subject against Entamoeba histolytica infection which method comprises administering to said subject an effective amount of the composition of claim 5.

14. A method to immunize a subject against Entamoeba histolytica infection which method comprises administering to said subject an effective amount of the composition of claim 6.

15. A method to immunize a subject against Entamoeba histolytica infection which method comprises administering to said subject an effective amount of the composition of claim 7.

16. A method to immunize a subject against Entamoeba histolytica infection which method comprises administering to said subject an effective amount of the composition of claim 8.

17. The composition of claim 1 wherein said peptide is produced in prokaryotic cells.

18. A vaccine composition for immunizing a subject against E. histolytica infection comprising a fusion protein that includes the peptide of claim 1.

19. A vaccine composition for immunizing a subject against E. histolytica infection comprising a fusion protein that includes the peptide of claim 5.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 3892 base pairs
      (B) TYPE: nucleic acid
      (C) STRANDEDNESS: single
      (D) TOPOLOGY: linear (ix) FEATURE:
    (A) NAME/KEY: CDS
    (B) LOCATION: join(1..3873, 3877..3882, 3886..3891)

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AAA | TTA | TTA | TTA | TTA | AAT | ATC | TTA | TTA | TTA | TGT | TGT | CTT | GCA | GAT | 48 |
| Met | Lys | Leu | Leu | Leu | Leu | Asn | Ile | Leu | Leu | Leu | Cys | Cys | Leu | Ala | Asp | |
| 1 | | | | 5 | | | | | 10 | | | | | 15 | | |
| AAA | CTT | GAT | GAA | TTT | TCA | GCA | GAT | AAT | GAC | TAT | TAT | GAC | GGT | GGT | ATT | 96 |
| Lys | Leu | Asp | Glu | Phe | Ser | Ala | Asp | Asn | Asp | Tyr | Tyr | Asp | Gly | Gly | Ile | |
| | | | 20 | | | | | 25 | | | | | 30 | | | |
| ATG | TCT | CGT | GGA | AAG | AAT | GCA | GGT | TCA | TGG | TAT | CAT | TCT | TAC | ACT | CAC | 144 |
| Met | Ser | Arg | Gly | Lys | Asn | Ala | Gly | Ser | Trp | Tyr | His | Ser | Tyr | Thr | His | |
| | | 35 | | | | | 40 | | | | | 45 | | | | |
| CAA | TAT | GAT | GTT | TTC | TAT | TAT | TTA | GCT | ATG | CAA | CCA | TGG | AGA | CAT | TTT | 192 |
| Gln | Tyr | Asp | Val | Phe | Tyr | Tyr | Leu | Ala | Met | Gln | Pro | Trp | Arg | His | Phe | |
| | 50 | | | | | 55 | | | | | 60 | | | | | |
| GTA | TGG | ACT | ACA | TGC | GAT | AAA | AAT | GAT | AAT | ACA | GAA | TGT | TAT | AAA | TAT | 240 |
| Val | Trp | Thr | Thr | Cys | Asp | Lys | Asn | Asp | Asn | Thr | Glu | Cys | Tyr | Lys | Tyr | |
| 65 | | | | | 70 | | | | | 75 | | | | | 80 | |
| ACT | ATC | AAT | GAA | GAT | CAT | AAT | GTA | AAG | GTT | GAA | GAT | ATT | AAT | AAA | ACA | 288 |
| Thr | Ile | Asn | Glu | Asp | His | Asn | Val | Lys | Val | Glu | Asp | Ile | Asn | Lys | Thr | |
| | | | | 85 | | | | | 90 | | | | | 95 | | |
| AAT | ATT | AAA | CAA | GAT | TTT | TGT | CAA | AAA | GAA | TAT | GCA | TAT | CCA | ATT | GAA | 336 |
| Asn | Ile | Lys | Gln | Asp | Phe | Cys | Gln | Lys | Glu | Tyr | Ala | Tyr | Pro | Ile | Glu | |
| | | | 100 | | | | | 105 | | | | | 110 | | | |
| AAA | TAT | GAA | GTT | GAT | TGG | GAC | AAT | GTT | CCA | GTT | GAT | GAA | CAA | CGA | ATT | 384 |
| Lys | Tyr | Glu | Val | Asp | Trp | Asp | Asn | Val | Pro | Val | Asp | Glu | Gln | Arg | Ile | |
| | | 115 | | | | | 120 | | | | | 125 | | | | |
| GAA | AGT | GTA | GAT | ATT | AAT | GGA | AAA | ACT | TGT | TTT | AAA | TAT | GCA | GCT | AAA | 432 |
| Glu | Ser | Val | Asp | Ile | Asn | Gly | Lys | Thr | Cys | Phe | Lys | Tyr | Ala | Ala | Lys | |
| | 130 | | | | | 135 | | | | | 140 | | | | | |
| AGA | CCA | TTG | GCT | TAT | GTT | TAT | TTA | AAT | ACA | AAA | ATG | ACA | TAT | GCA | ACA | 480 |
| Arg | Pro | Leu | Ala | Tyr | Val | Tyr | Leu | Asn | Thr | Lys | Met | Thr | Tyr | Ala | Thr | |
| 145 | | | | | 150 | | | | | 155 | | | | | 160 | |
| AAA | ACT | GAA | GCA | TAT | GAT | GTT | TGT | AGA | ATG | GAT | TTC | ATT | GGA | GGA | AGA | 528 |
| Lys | Thr | Glu | Ala | Tyr | Asp | Val | Cys | Arg | Met | Asp | Phe | Ile | Gly | Gly | Arg | |
| | | | | 165 | | | | | 170 | | | | | 175 | | |
| TCA | ATT | ACA | TTC | AGA | TCA | TTT | AAC | ACA | GAG | AAT | AAA | GCA | TTT | ATT | GAT | 576 |
| Ser | Ile | Thr | Phe | Arg | Ser | Phe | Asn | Thr | Glu | Asn | Lys | Ala | Phe | Ile | Asp | |
| | | | 180 | | | | | 185 | | | | | 190 | | | |
| CAA | TAT | AAT | ACA | AAC | ACT | ACA | TCA | AAA | TGT | CTT | CTT | AAT | GTA | TAT | GAT | 624 |
| Gln | Tyr | Asn | Thr | Asn | Thr | Thr | Ser | Lys | Cys | Leu | Leu | Asn | Val | Tyr | Asp | |
| | | 195 | | | | | 200 | | | | | 205 | | | | |
| AAT | AAT | GTT | AAT | ACA | CAT | CTT | GCA | ATT | ATC | TTT | GGT | ATT | ACT | GAT | TCT | 672 |
| Asn | Asn | Val | Asn | Thr | His | Leu | Ala | Ile | Ile | Phe | Gly | Ile | Thr | Asp | Ser | |
| | 210 | | | | | 215 | | | | | 220 | | | | | |
| ACA | GTC | ATT | AAA | TCA | CTT | CAA | GAG | AAT | TTA | TCT | CTT | TTA | AGT | CAA | CTA | 720 |
| Thr | Val | Ile | Lys | Ser | Leu | Gln | Glu | Asn | Leu | Ser | Leu | Leu | Ser | Gln | Leu | |
| 225 | | | | | 230 | | | | | 235 | | | | | 240 | |
| AAA | ACA | GTC | AAA | GGA | GTA | ACA | CTC | TAC | TAT | CTT | AAA | GAT | GAT | ACT | TAT | 768 |
| Lys | Thr | Val | Lys | Gly | Val | Thr | Leu | Tyr | Tyr | Leu | Lys | Asp | Asp | Thr | Tyr | |
| | | | | 245 | | | | | 250 | | | | | 255 | | |
| TTT | ACA | GTT | AAT | ATT | ACT | TTA | GAT | CAA | TTA | AAA | TAT | GAT | ACA | CTT | GTC | 816 |
| Phe | Thr | Val | Asn | Ile | Thr | Leu | Asp | Gln | Leu | Lys | Tyr | Asp | Thr | Leu | Val | |
| | | | 260 | | | | | 265 | | | | | 270 | | | |
| AAA | TAC | ACA | GCA | GGA | ACA | GGA | CAA | GTT | GAT | CCA | CTT | ATT | AAT | ATT | GCT | 864 |
| Lys | Tyr | Thr | Ala | Gly | Thr | Gly | Gln | Val | Asp | Pro | Leu | Ile | Asn | Ile | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| AAG | AAT | GAT | TTA | GCT | ACT | AAA | GTT | GCA | GAT | AAA | AGT | AAA | GAT | AAA | AAT | 912 |
| Lys | Asn | Asp | Leu | Ala | Thr | Lys | Val | Ala | Asp | Lys | Ser | Lys | Asp | Lys | Asn | |
| | | | 290 | | | | 295 | | | | 300 | | | | | |
| GCA | AAT | GAT | AAA | ATC | AAA | AGA | GGA | ACT | ATG | ATT | GTG | TTA | ATG | GAT | ACT | 960 |
| Ala | Asn | Asp | Lys | Ile | Lys | Arg | Gly | Thr | Met | Ile | Val | Leu | Met | Asp | Thr | |
| 305 | | | | | 310 | | | | 315 | | | | | 320 | | |
| GCA | CTT | GGA | TCA | GAA | TTT | AAT | GCA | GAA | ACA | GAA | TTT | GAT | AGA | AAG | AAT | 1008 |
| Ala | Leu | Gly | Ser | Glu | Phe | Asn | Ala | Glu | Thr | Glu | Phe | Asp | Arg | Lys | Asn | |
| | | | | 325 | | | | | 330 | | | | | 335 | | |
| ATT | TCA | GTT | CAT | ACT | GTT | GTT | CTT | AAT | AGA | AAT | AAA | GAC | CCA | AAG | ATT | 1056 |
| Ile | Ser | Val | His | Thr | Val | Val | Leu | Asn | Arg | Asn | Lys | Asp | Pro | Lys | Ile | |
| | | | 340 | | | | | 345 | | | | | 350 | | | |
| ACA | CGT | AGT | GCA | TTG | AGA | CTT | GTT | TCA | CTT | GGA | CCA | CAT | TAT | CAT | GAA | 1104 |
| Thr | Arg | Ser | Ala | Leu | Arg | Leu | Val | Ser | Leu | Gly | Pro | His | Tyr | His | Glu | |
| | | 355 | | | | | 360 | | | | | 365 | | | | |
| TTT | ACA | GGT | AAT | GAT | GAA | GTT | AAT | GCA | ACA | ATC | ACT | GCA | CTT | TTC | AAA | 1152 |
| Phe | Thr | Gly | Asn | Asp | Glu | Val | Asn | Ala | Thr | Ile | Thr | Ala | Leu | Phe | Lys | |
| 370 | | | | | 375 | | | | | 380 | | | | | | |
| GGA | ATT | AGA | GCC | AAT | TTA | ACA | GAA | AGA | TGT | GAT | AGA | GAT | AAA | TGT | TCA | 1200 |
| Gly | Ile | Arg | Ala | Asn | Leu | Thr | Glu | Arg | Cys | Asp | Arg | Asp | Lys | Cys | Ser | |
| 385 | | | | 390 | | | | | 395 | | | | | 400 | | |
| GGA | TTT | TGT | GAT | GCA | ATG | AAT | AGA | TGC | ACA | TGT | CCA | ATG | TGT | TGT | GAG | 1248 |
| Gly | Phe | Cys | Asp | Ala | Met | Asn | Arg | Cys | Thr | Cys | Pro | Met | Cys | Cys | Glu | |
| | | | | 405 | | | | | 410 | | | | | 415 | | |
| AAT | GAT | TGT | TTC | TAT | ACA | TCC | TGT | GAT | GTA | GAA | ACA | GGA | TCA | TGT | ATT | 1296 |
| Asn | Asp | Cys | Phe | Tyr | Thr | Ser | Cys | Asp | Val | Glu | Thr | Gly | Ser | Cys | Ile | |
| | | | 420 | | | | | 425 | | | | | 430 | | | |
| CCA | TGG | CCT | AAA | GCT | AAA | CCA | AAA | GCA | AAG | AAA | GAA | TGT | CCA | GCA | ACA | 1344 |
| Pro | Trp | Pro | Lys | Ala | Lys | Pro | Lys | Ala | Lys | Lys | Glu | Cys | Pro | Ala | Thr | |
| | | | 435 | | | | | 440 | | | | | 445 | | | |
| TGT | GTA | GGC | TCA | TAT | GAA | TGT | AGA | GAT | CTT | GAA | GGA | TGT | GTT | GTT | ACA | 1392 |
| Cys | Val | Gly | Ser | Tyr | Glu | Cys | Arg | Asp | Leu | Glu | Gly | Cys | Val | Val | Thr | |
| 450 | | | | | 455 | | | | | 460 | | | | | | |
| AAA | TAT | AAT | GAC | ACA | TGC | CAA | CCA | AAA | GTG | AAA | TGC | ATG | GTA | CCA | TAT | 1440 |
| Lys | Tyr | Asn | Asp | Thr | Cys | Gln | Pro | Lys | Val | Lys | Cys | Met | Val | Pro | Tyr | |
| 465 | | | | 470 | | | | | 475 | | | | | 480 | | |
| TGT | GAT | AAT | GAT | AAG | AAT | CTA | ACT | GAA | GTA | TGT | AAA | CAA | AAA | GCT | AAT | 1488 |
| Cys | Asp | Asn | Asp | Lys | Asn | Leu | Thr | Glu | Val | Cys | Lys | Gln | Lys | Ala | Asn | |
| | | | | 485 | | | | | 490 | | | | | 495 | | |
| TGT | GAA | GCA | GAT | CAA | AAA | CCA | AGT | TCT | GAT | GGA | TAT | TGT | TGG | AGT | TAT | 1536 |
| Cys | Glu | Ala | Asp | Gln | Lys | Pro | Ser | Ser | Asp | Gly | Tyr | Cys | Trp | Ser | Tyr | |
| | | | 500 | | | | | 505 | | | | | 510 | | | |
| ACA | TGT | GAC | CAA | ACT | ACT | GGT | TTT | TGT | AAG | AAA | GAT | AAA | CGA | GGT | AAA | 1584 |
| Thr | Cys | Asp | Gln | Thr | Thr | Gly | Phe | Cys | Lys | Lys | Asp | Lys | Arg | Gly | Lys | |
| | | 515 | | | | | 520 | | | | | 525 | | | | |
| GAA | ATG | TGT | ACA | GGA | AAG | ACA | AAT | AAT | TGT | CAA | GAA | TAT | GTT | TGT | GAT | 1632 |
| Glu | Met | Cys | Thr | Gly | Lys | Thr | Asn | Asn | Cys | Gln | Glu | Tyr | Val | Cys | Asp | |
| 530 | | | | | 535 | | | | | 540 | | | | | | |
| TCA | GAA | CAA | AGA | TGT | AGT | GTT | AGA | GAT | AAA | GTA | TGT | GTA | AAA | ACA | TCA | 1680 |
| Ser | Glu | Gln | Arg | Cys | Ser | Val | Arg | Asp | Lys | Val | Cys | Val | Lys | Thr | Ser | |
| 545 | | | | 550 | | | | | 555 | | | | | 560 | | |
| CCA | TAC | ATT | GAA | ATG | TCA | TGT | TAT | GTA | GCC | AAG | TGT | AAT | CTC | AAT | ACA | 1728 |
| Pro | Tyr | Ile | Glu | Met | Ser | Cys | Tyr | Val | Ala | Lys | Cys | Asn | Leu | Asn | Thr | |
| | | | | 565 | | | | | 570 | | | | | 575 | | |
| GGT | ATG | TGT | GAG | AAC | AGA | TTA | TCA | TGT | GAT | ACA | TAC | TCA | TCA | TGT | GGT | 1776 |
| Gly | Met | Cys | Glu | Asn | Arg | Leu | Ser | Cys | Asp | Thr | Tyr | Ser | Ser | Cys | Gly | |
| | | | | 580 | | | | | 585 | | | | | 590 | | |
| GGA | GAT | TCT | ACA | GGA | TCA | GTA | TGT | AAA | TGT | GAT | TCT | ACA | ACT | GGT | AAT | 1824 |
| Gly | Asp | Ser | Thr | Gly | Ser | Val | Cys | Lys | Cys | Asp | Ser | Thr | Thr | Gly | Asn | |
| | | | 595 | | | | | 600 | | | | | 605 | | | |

```
AAA TGT CAA TGT AAT AAA GTA AAA AAT GGT AAT TAT TGT AAT TCT AAA      1872
Lys Cys Gln Cys Asn Lys Val Lys Asn Gly Asn Tyr Cys Asn Ser Lys
610             615                 620

AAC CAT GAA ATT TGT GAT TAT ACA GGA ACA ACA CCA CAA TGT AAA GTG      1920
Asn His Glu Ile Cys Asp Tyr Thr Gly Thr Thr Pro Gln Cys Lys Val
625             630                 635                 640

TCT AAT TGT ACA GAA GAT CTT GTT AGA GAT GGA TGT CTT ATT AAG AGA      1968
Ser Asn Cys Thr Glu Asp Leu Val Arg Asp Gly Cys Leu Ile Lys Arg
                645                 650                 655

TGC AAT GAA ACA AGT AAA ACA ACA TAT TGG GAG AAT GTT GAT TGT TCA      2016
Cys Asn Glu Thr Ser Lys Thr Thr Tyr Trp Glu Asn Val Asp Cys Ser
            660                 665                 670

AAC ACT AAG ATT GAA TTT GCT AAA GAT GAT AAA TCT GAA ACT ATG TGT      2064
Asn Thr Lys Ile Glu Phe Ala Lys Asp Asp Lys Ser Glu Thr Met Cys
        675                 680                 685

AAA CAA TAT TAT TCA ACT ACA TGT TTG AAT GGA AAA TGT GTT GTT CAA      2112
Lys Gln Tyr Tyr Ser Thr Thr Cys Leu Asn Gly Lys Cys Val Val Gln
    690                 695                 700

GCA GTT GGT GAT GTT TCT AAT GTA GGA TGT GGA TAT TGT TCA ATG GGA      2160
Ala Val Gly Asp Val Ser Asn Val Gly Cys Gly Tyr Cys Ser Met Gly
705                 710                 715                 720

ACA GAT AAT ATT ATT ACA TAT CAT GAT GAT TGT AAT TCA CGT AAA TCA      2208
Thr Asp Asn Ile Ile Thr Tyr His Asp Asp Cys Asn Ser Arg Lys Ser
                725                 730                 735

CAA TGT GGA AAC TTT AAT GGT AAA TGT ATT AAA GGC AGT GAC AAT TCT      2256
Gln Cys Gly Asn Phe Asn Gly Lys Cys Ile Lys Gly Ser Asp Asn Ser
                740                 745                 750

TAT TCT TGT GTA TTT GAA AAA GAT AAA ACT TCT TCT AAA TCA GAT AAT      2304
Tyr Ser Cys Val Phe Glu Lys Asp Lys Thr Ser Ser Lys Ser Asp Asn
            755                 760                 765

GAT ATT TGT GCT GAA TGT TCT AGT TTA ACA TGT CCA GCT GAT ACT ACA      2352
Asp Ile Cys Ala Glu Cys Ser Ser Leu Thr Cys Pro Ala Asp Thr Thr
        770                 775                 780

TAC AGA ACA TAT ACA TAT GAC TCA AAA ACA GGA ACA TGT AAA GCA ACT      2400
Tyr Arg Thr Tyr Thr Tyr Asp Ser Lys Thr Gly Thr Cys Lys Ala Thr
785                 790                 795                 800

GTT CAA CCA ACA CCA GCA TGT TCA GTA TGT GAA AGT GGT AAA TTT GTA      2448
Val Gln Pro Thr Pro Ala Cys Ser Val Cys Glu Ser Gly Lys Phe Val
                805                 810                 815

GAG AAA TGC AAA GAT CAA AAA TTA GAA CGT AAA GTC ACT TTA GAA AAT      2496
Glu Lys Cys Lys Asp Gln Lys Leu Glu Arg Lys Val Thr Leu Glu Asn
                820                 825                 830

GGA AAA GAA TAT AAA TAC ACC ATT CCA AAA GAT TGT GTC AAT GAA CAA      2544
Gly Lys Glu Tyr Lys Tyr Thr Ile Pro Lys Asp Cys Val Asn Glu Gln
            835                 840                 845

TGC ATT CCA AGA ACA TAC ATA GAT TGT TTA GGT AAT GAT GAT AAC TTT      2592
Cys Ile Pro Arg Thr Tyr Ile Asp Cys Leu Gly Asn Asp Asp Asn Phe
        850                 855                 860

AAA TCT ATT TAT AAC TTC TAT TTA CCA TGT CAA GCA TAT GTT ACA GCT      2640
Lys Ser Ile Tyr Asn Phe Tyr Leu Pro Cys Gln Ala Tyr Val Thr Ala
865                 870                 875                 880

ACC TAT CAT TAC AGT TCA TTA TTC AAT TTA ACT AGT TAT AAA CTT CAC      2688
Thr Tyr His Tyr Ser Ser Leu Phe Asn Leu Thr Ser Tyr Lys Leu His
                885                 890                 895

TTA CCA CAA AGT GAA GAA TTT ATG AAA GAG GCA GAC AAA GAA GCA TAT      2736
Leu Pro Gln Ser Glu Glu Phe Met Lys Glu Ala Asp Lys Glu Ala Tyr
                900                 905                 910

TGT ACA TAC GAA ATA ACA ACA AGA GAA TGT AAA ACA TGT TCA TTA ATT      2784
Cys Thr Tyr Glu Ile Thr Thr Arg Glu Cys Lys Thr Cys Ser Leu Ile
```

```
              915                 920                 925
GAA ACT AGA GAA AAA GTC CAA GAA GTT GAT TTG TGT GCA GAA GAA ACT          2832
Glu Thr Arg Glu Lys Val Gln Glu Val Asp Leu Cys Ala Glu Glu Thr
        930                 935                 940

AAG AAT GGA GGA GTT CCA TTC AAA TGT AAG AAT AAC AAT TGC ATT ATT          2880
Lys Asn Gly Gly Val Pro Phe Lys Cys Lys Asn Asn Asn Cys Ile Ile
945                 950                 955                 960

GAT CCT AAC TTT GAT TGT CAA CCT ATT GAA TGT AAG ATT CAA GAG ATT          2928
Asp Pro Asn Phe Asp Cys Gln Pro Ile Glu Cys Lys Ile Gln Glu Ile
                965                 970                 975

GTT ATT ACA GAA AAA GAT GGA ATA AAA ACA ACA TGT AAA AAT ACT              2976
Val Ile Thr Glu Lys Asp Gly Ile Lys Thr Thr Thr Cys Lys Asn Thr
            980                 985                 990

ACA AAA GCA ACA TGT GAC ACT AAC AAT AAG AGA ATA GAA GAT GCA CGT          3024
Thr Lys Ala Thr Cys Asp Thr Asn Asn Lys Arg Ile Glu Asp Ala Arg
        995                 1000                1005

AAA GCA TTC ATT GAA GGA AAA GAA GGA ATT GAG CAA GTA GAA TGT GCA          3072
Lys Ala Phe Ile Glu Gly Lys Glu Gly Ile Glu Gln Val Glu Cys Ala
    1010                1015                1020

AGT ACT GTT TGT CAA AAT GAT AAT AGT TGT CCA ATT ATT ACT GAT GTA          3120
Ser Thr Val Cys Gln Asn Asp Asn Ser Cys Pro Ile Ile Thr Asp Val
1025                1030                1035                1040

GAA AAA TGT AAT CAA AAC ACA GAA GTA GAT TAT GGA TGT AAA GCA ATG          3168
Glu Lys Cys Asn Gln Asn Thr Glu Val Asp Tyr Gly Cys Lys Ala Met
                1045                1050                1055

ACA GGA GAA TGT GAT GGT ACT ACA TAT CTT TGT AAA TTT GTA CAA CTT          3216
Thr Gly Glu Cys Asp Gly Thr Thr Tyr Leu Cys Lys Phe Val Gln Leu
            1060                1065                1070

ACT GAT GAT CCA TCA TTA GAT AGT GAA CAT TTT AGA ACT AAA TCA GGA          3264
Thr Asp Asp Pro Ser Leu Asp Ser Glu His Phe Arg Thr Lys Ser Gly
        1075                1080                1085

GTT GAA CTT AAC AAT GCA TGT TTG AAA TAT AAA TGT GTT GAG AGT AAA          3312
Val Glu Leu Asn Asn Ala Cys Leu Lys Tyr Lys Cys Val Glu Ser Lys
    1090                1095                1100

GGA AGT GAT GGA AAA ATC ACA CAT AAA TGG GAA ATT GAT ACA GAA CGA          3360
Gly Ser Asp Gly Lys Ile Thr His Lys Trp Glu Ile Asp Thr Glu Arg
1105                1110                1115                1120

TCA AAT GCT AAT CCA AAA CCA AGA AAT CCA TGC GAA ACC GCA ACA TGT          3408
Ser Asn Ala Asn Pro Lys Pro Arg Asn Pro Cys Glu Thr Ala Thr Cys
                1125                1130                1135

AAT CAA ACA ACT GGA GAA ACT ATT TAC ACA AAG AAA ACA TGT ACT GTT          3456
Asn Gln Thr Thr Gly Glu Thr Ile Tyr Thr Lys Lys Thr Cys Thr Val
            1140                1145                1150

TCA GAA TTC CCA ACA ATC ACA CCA AAT CAA GGA AGA TGT TTC TAT TGT          3504
Ser Glu Phe Pro Thr Ile Thr Pro Asn Gln Gly Arg Cys Phe Tyr Cys
        1155                1160                1165

CAA TGT TCA TAT CTT GAC GGT TCA TCA GTT CTT ACT ATG TAT GGA GAA          3552
Gln Cys Ser Tyr Leu Asp Gly Ser Ser Val Leu Thr Met Tyr Gly Glu
    1170                1175                1180

ACA GAT AAA GAA TAT TAT GAT CTT GAT GCA TGT GGT AAT TGT CGT GTT          3600
Thr Asp Lys Glu Tyr Tyr Asp Leu Asp Ala Cys Gly Asn Cys Arg Val
1185                1190                1195                1200

TGG AAT CAG ACA GAT AGA ACA CAA CAA CTT AAT AAT CAC ACC GAG TGT          3648
Trp Asn Gln Thr Asp Arg Thr Gln Gln Leu Asn Asn His Thr Glu Cys
                1205                1210                1215

ATT CTC GCA GGA GAA ATT AAT AAT GTT GGA GCT ATT GCA GCG GCA ACT          3696
Ile Leu Ala Gly Glu Ile Asn Asn Val Gly Ala Ile Ala Ala Ala Thr
            1220                1225                1230

ACT GTG GCT GCT GTT ATA GTT GCA GTT GTA GTT GCA TTA ATT GTT GTT          3744
```

```
Thr Val Ala Ala Val Ile Val Ala Val Val Ala Leu Ile Val Val
    1235                1240                1245

TCT ATT GGA TTA TTT AAG ACT TAT CAA CTT GTT TCA TCA GCT ATG AAG        3792
Ser Ile Gly Leu Phe Lys Thr Tyr Gln Leu Val Ser Ser Ala Met Lys
    1250                1255                1260

AAT GCC ATT ACA ATA ACT AAT GAA AAT GCA GAA TAT GTT GGA GCA GAT        3840
Asn Ala Ile Thr Ile Thr Asn Glu Asn Ala Glu Tyr Val Gly Ala Asp
1265                1270                1275                1280

AAT GAA GCA ACT AAT GCA GCA ACA TTC AAT GGA TAA GAA CAA                3882
Asn Glu Ala Thr Asn Ala Ala Thr Phe Asn Gly     Glu Gln
                1285                1290

TAA TTA AGC C                                                          3892
    Leu Ser
        1295

(2) INFORMATION FOR SEQ ID NO:2:

(i) SEQUENCE CHARACTERISTICS:
        (A) LENGTH: 1295 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Leu Leu Leu Asn Ile Leu Leu Leu Cys Cys Leu Ala Asp
 1               5                   10                  15

Lys Leu Asp Glu Phe Ser Ala Asp Asn Asp Tyr Tyr Asp Gly Gly Ile
             20                  25                  30

Met Ser Arg Gly Lys Asn Ala Gly Ser Trp Tyr His Ser Tyr Thr His
         35                  40                  45

Gln Tyr Asp Val Phe Tyr Tyr Leu Ala Met Gln Pro Trp Arg His Phe
     50                  55                  60

Val Trp Thr Thr Cys Asp Lys Asn Asp Asn Thr Glu Cys Tyr Lys Tyr
 65                  70                  75                  80

Thr Ile Asn Glu Asp His Asn Val Lys Val Glu Asp Ile Asn Lys Thr
             85                  90                  95

Asn Ile Lys Gln Asp Phe Cys Gln Lys Glu Tyr Ala Tyr Pro Ile Glu
             100                 105                 110

Lys Tyr Glu Val Asp Trp Asp Asn Val Pro Val Asp Glu Gln Arg Ile
         115                 120                 125

Glu Ser Val Asp Ile Asn Gly Leu Thr Cys Phe Lys Tyr Ala Ala Lys
130                 135                 140

Arg Pro Leu Ala Tyr Val Tyr Leu Asn Thr Lys Met Thr Tyr Ala Thr
145                 150                 155                 160

Lys Thr Glu Ala Tyr Asp Val Cys Arg Met Asp Phe Ile Gly Gly Arg
                165                 170                 175

Ser Ile Thr Phe Arg Ser Phe Asn Thr Glu Asn Lys Ala Phe Ile Asp
            180                 185                 190

Gln Tyr Asn Thr Asn Thr Thr Ser Lys Cys Leu Leu Asn Val Tyr Asp
        195                 200                 205

Asn Asn Val Asn Thr His Leu Ala Ile Ile Phe Gly Ile Thr Asp Ser
    210                 215                 220

Thr Val Ile Lys Ser Leu Gln Glu Asn Leu Ser Leu Ser Gln Leu
225                 230                 235                 240

Lys Thr Val Lys Gly Val Thr Leu Tyr Tyr Leu Lys Asp Asp Thr Tyr
                245                 250                 255
```

-continued

```
Phe Thr Val Asn Ile Thr Leu Asp Gln Leu Lys Tyr Asp Thr Leu Val
            260                 265                 270
Lys Tyr Thr Ala Gly Thr Gly Gln Val Asp Pro Leu Ile Asn Ile Ala
        275                 280                 285
Lys Asn Asp Leu Ala Thr Lys Val Ala Asp Lys Ser Lys Asp Lys Asn
290                 295                 300
Ala Asn Asp Lys Ile Lys Arg Gly Thr Met Ile Val Leu Met Asp Thr
305                 310                 315                 320
Ala Leu Gly Ser Glu Phe Asn Ala Glu Thr Glu Phe Asp Arg Lys Asn
                325                 330                 335
Ile Ser Val His Thr Val Leu Asn Arg Asn Lys Asp Pro Lys Ile
                    340                 345                 350
Thr Arg Ser Ala Leu Arg Leu Val Ser Leu Gly Pro His Tyr His Glu
        355                 360                 365
Phe Thr Gly Asn Asp Glu Val Asn Ala Thr Ile Thr Ala Leu Phe Lys
    370                 375                 380
Gly Ile Arg Ala Asn Leu Thr Glu Arg Cys Asp Arg Asp Lys Cys Ser
385                 390                 395                 400
Gly Phe Cys Asp Ala Met Asn Arg Cys Thr Cys Pro Met Cys Cys Glu
                405                 410                 415
Asn Asp Cys Phe Tyr Thr Ser Cys Asp Val Glu Thr Gly Ser Cys Ile
                420                 425                 430
Pro Trp Pro Lys Ala Lys Pro Lys Ala Lys Lys Glu Cys Pro Ala Thr
            435                 440                 445
Cys Val Gly Ser Tyr Glu Cys Arg Asp Leu Glu Gly Cys Val Val Thr
        450                 455                 460
Lys Tyr Asn Asp Thr Cys Gln Pro Lys Val Lys Cys Met Val Pro Tyr
465                 470                 475                 480
Cys Asp Asn Asp Lys Asn Leu Thr Glu Val Cys Lys Gln Lys Ala Asn
                485                 490                 495
Cys Glu Ala Asp Gln Lys Pro Ser Ser Asp Gly Tyr Cys Trp Ser Tyr
                500                 505                 510
Thr Cys Asp Gln Thr Thr Gly Phe Cys Lys Lys Asp Lys Arg Gly Lys
        515                 520                 525
Glu Met Cys Thr Gly Lys Thr Asn Asn Cys Gln Glu Tyr Val Cys Asp
    530                 535                 540
Ser Glu Gln Arg Cys Ser Val Arg Asp Lys Val Cys Val Lys Thr Ser
545                 550                 555                 560
Pro Tyr Ile Glu Met Ser Cys Tyr Val Ala Lys Cys Asn Leu Asn Thr
                565                 570                 575
Gly Met Cys Glu Asn Arg Leu Ser Cys Asp Thr Tyr Ser Ser Cys Gly
                580                 585                 590
Gly Asp Ser Thr Gly Ser Val Cys Lys Cys Asp Ser Thr Thr Gly Asn
        595                 600                 605
Lys Cys Gln Cys Asn Lys Val Lys Asn Gly Asn Tyr Cys Asn Ser Lys
    610                 615                 620
Asn His Glu Ile Cys Asp Tyr Thr Gly Thr Thr Pro Gln Cys Lys Val
625                 630                 635                 640
Ser Asn Cys Thr Glu Asp Leu Val Arg Asp Gly Cys Leu Ile Lys Arg
                645                 650                 655
Cys Asn Glu Thr Ser Lys Thr Thr Tyr Trp Glu Asn Val Asp Cys Ser
                660                 665                 670
Asn Thr Lys Ile Glu Phe Ala Lys Asp Asp Lys Ser Glu Thr Met Cys
```

-continued

```
            675                 680                 685
Lys Gln Tyr Tyr Ser Thr Thr Cys Leu Asn Gly Lys Cys Val Val Gln
    690                 695                 700

Ala Val Gly Asp Val Ser Asn Val Gly Cys Gly Tyr Cys Ser Met Gly
705                 710                 715                 720

Thr Asp Asn Ile Ile Thr Tyr His Asp Asp Cys Asn Ser Arg Lys Ser
                725                 730                 735

Gln Cys Gly Asn Phe Asn Gly Lys Cys Ile Lys Gly Ser Asp Asn Ser
            740                 745                 750

Tyr Ser Cys Val Phe Glu Lys Asp Lys Thr Ser Ser Lys Ser Asp Asn
        755                 760                 765

Asp Ile Cys Ala Glu Cys Ser Ser Leu Thr Cys Pro Ala Asp Thr Thr
    770                 775                 780

Tyr Arg Thr Tyr Thr Tyr Asp Ser Lys Thr Gly Thr Cys Lys Ala Thr
785                 790                 795                 800

Val Gln Pro Thr Pro Ala Cys Ser Val Cys Glu Ser Gly Lys Phe Val
                805                 810                 815

Glu Lys Cys Lys Asp Gln Lys Leu Glu Arg Lys Val Thr Leu Glu Asn
            820                 825                 830

Gly Lys Glu Tyr Lys Tyr Thr Ile Pro Lys Asp Cys Val Asn Glu Gln
        835                 840                 845

Cys Ile Pro Arg Thr Tyr Ile Asp Cys Leu Gly Asn Asp Asp Asn Phe
    850                 855                 860

Lys Ser Ile Tyr Asn Phe Tyr Leu Pro Cys Gln Ala Tyr Val Thr Ala
865                 870                 875                 880

Thr Tyr His Tyr Ser Ser Leu Phe Asn Leu Thr Ser Tyr Lys Leu His
                885                 890                 895

Leu Pro Gln Ser Glu Glu Phe Met Lys Glu Ala Asp Lys Glu Ala Tyr
            900                 905                 910

Cys Thr Tyr Glu Ile Thr Thr Arg Glu Cys Lys Thr Cys Ser Leu Ile
        915                 920                 925

Glu Thr Arg Glu Lys Val Gln Glu Val Asp Leu Cys Ala Glu Glu Thr
    930                 935                 940

Lys Asn Gly Gly Val Pro Phe Lys Cys Lys Asn Asn Cys Ile Ile
945                 950                 955                 960

Asp Pro Asn Phe Asp Cys Gln Pro Ile Glu Cys Lys Ile Gln Glu Ile
                965                 970                 975

Val Ile Thr Glu Lys Asp Gly Ile Lys Thr Thr Thr Cys Lys Asn Thr
            980                 985                 990

Thr Lys Ala Thr Cys Asp Thr Asn Asn Lys Arg Ile Glu Asp Ala Arg
        995                 1000                1005

Lys Ala Phe Ile Glu Gly Lys Glu Gly Ile Glu Gln Val Glu Cys Ala
    1010                1015                1020

Ser Thr Val Cys Gln Asn Asp Asn Ser Cys Pro Ile Ile Thr Asp Val
1025                1030                1035                1040

Glu Lys Cys Asn Gln Asn Thr Glu Val Asp Tyr Gly Cys Lys Ala Met
                1045                1050                1055

Thr Gly Glu Cys Asp Gly Thr Thr Tyr Leu Cys Lys Phe Val Gln Leu
            1060                1065                1070

Thr Asp Asp Pro Ser Leu Asp Ser Glu His Phe Arg Thr Lys Ser Gly
        1075                1080                1085

Val Glu Leu Asn Asn Ala Cys Leu Lys Tyr Lys Cys Val Glu Ser Lys
    1090                1095                1100
```

-continued

```
Gly Ser Asp Gly Lys Ile Thr His Lys Trp Glu Ile Asp Thr Glu Arg
1105                1110                1115                1120

Ser Asn Ala Asn Pro Lys Pro Arg Asn Pro Cys Glu Thr Ala Thr Cys
            1125                1130                1135

Asn Gln Thr Thr Gly Glu Thr Ile Tyr Thr Lys Lys Thr Cys Thr Val
        1140                1145                1150

Ser Glu Phe Pro Thr Ile Thr Pro Asn Gln Gly Arg Cys Phe Tyr Cys
            1155                1160                1165

Gln Cys Ser Tyr Leu Asp Gly Ser Ser Val Leu Thr Met Tyr Gly Glu
        1170                1175                1180

Thr Asp Lys Glu Tyr Tyr Asp Leu Asp Ala Cys Gly Asn Cys Arg Val
1185                1190                1195                1200

Trp Asn Gln Thr Asp Arg Thr Gln Gln Leu Asn Asn His Thr Glu Cys
            1205                1210                1215

Ile Leu Ala Gly Glu Ile Asn Asn Val Gly Ala Ile Ala Ala Ala Thr
            1220                1225                1230

Thr Val Ala Ala Val Ile Val Ala Val Val Ala Leu Ile Val Val
            1235                1240                1245

Ser Ile Gly Leu Phe Lys Thr Tyr Gln Leu Val Ser Ser Ala Met Lys
            1250                1255                1260

Asn Ala Ile Thr Ile Thr Asn Glu Asn Ala Glu Tyr Val Gly Ala Asp
1265                1270                1275                1280

Asn Glu Ala Thr Asn Ala Ala Thr Phe Asn Gly Glu Gln Leu Ser
            1285                1290                1295

(2) INFORMATION FOR SEQ ID NO:3:

(i) SEQUENCE CHARACTERISTICS:
        (A) LENGTH: 1291 amino acids
        (B) TYPE: amino acid
        (C) STRANDEDNESS: single
        (D) TOPOLOGY: linear (xi) SEQUENCE DESCRIPTION: SEQ ID NO:3:

Met Lys Leu Leu Leu Leu Asn Ile Leu Leu Leu Cys Cys Leu Ala Asp
1               5                   10                  15

Lys Leu Asp Glu Phe Ser Ala Asp Asn Asp Tyr Tyr Asp Gly Gly Ile
            20                  25                  30

Met Ser Arg Gly Lys Asn Ala Gly Ser Trp Tyr His Ser Tyr Thr His
            35                  40                  45

Gln Tyr Asp Val Phe Tyr Tyr Leu Ala Met Gln Pro Trp Arg His Phe
        50                  55                  60

Val Trp Thr Thr Cys Asp Lys Asn Asp Asn Thr Glu Cys Tyr Lys Tyr
65                  70                  75                  80

Thr Ile Asn Glu Asp His Asn Val Lys Val Glu Asp Ile Asn Lys Thr
                85                  90                  95

Asn Ile Lys Gln Asp Phe Cys Gln Lys Glu Tyr Ala Tyr Pro Ile Glu
            100                 105                 110

Lys Tyr Glu Val Asp Trp Asp Asn Val Pro Val Asp Glu Gln Arg Ile
        115                 120                 125

Glu Ser Val Asp Ile Asn Gly Lys Thr Cys Phe Lys Tyr Ala Ala Lys
        130                 135                 140

Arg Pro Leu Ala Tyr Val Tyr Leu Asn Thr Lys Met Thr Tyr Ala Thr
145                 150                 155                 160

Lys Thr Glu Ala Tyr Asp Val Cys Arg Met Asp Phe Ile Gly Gly Arg
```

-continued

```
                165                 170                 175
Ser Ile Thr Phe Arg Ser Phe Asn Thr Glu Asn Lys Ala Phe Ile Asp
                    180                 185                 190

Gln Tyr Asn Thr Asn Thr Thr Ser Lys Cys Leu Leu Asn Val Tyr Asp
                195                 200                 205

Asn Asn Val Asn Thr His Leu Ala Ile Ile Phe Gly Ile Thr Asp Ser
210                 215                 220

Thr Val Ile Lys Ser Leu Gln Glu Asn Leu Ser Leu Leu Ser Gln Leu
225                 230                 235                 240

Lys Thr Val Lys Gly Val Thr Leu Tyr Tyr Leu Lys Asp Asp Thr Tyr
                    245                 250                 255

Phe Thr Val Asn Ile Thr Leu Asp Gln Leu Lys Tyr Asp Thr Leu Val
                260                 265                 270

Lys Tyr Thr Ala Gly Thr Gly Gln Val Asp Pro Leu Ile Asn Ile Ala
            275                 280                 285

Lys Asn Asp Leu Ala Thr Lys Val Ala Asp Lys Ser Lys Asp Lys Asn
        290                 295                 300

Ala Asn Asp Lys Ile Lys Arg Gly Thr Met Ile Val Leu Met Asp Thr
305                 310                 315                 320

Ala Leu Gly Ser Glu Phe Asn Ala Glu Thr Glu Phe Asp Arg Lys Asn
                    325                 330                 335

Ile Ser Val His Thr Val Leu Asn Arg Asn Lys Asp Pro Lys Ile
                340                 345                 350

Thr Arg Ser Ala Leu Arg Leu Val Ser Leu Gly Pro His Tyr His Glu
            355                 360                 365

Phe Thr Gly Asn Asp Glu Val Asn Ala Thr Ile Thr Ala Leu Phe Lys
        370                 375                 380

Gly Ile Arg Ala Asn Leu Thr Glu Arg Cys Asp Arg Asp Lys Cys Ser
385                 390                 395                 400

Gly Phe Cys Asp Ala Met Asn Arg Cys Thr Cys Pro Met Cys Cys Glu
                    405                 410                 415

Asn Asp Cys Phe Tyr Thr Ser Cys Asp Val Glu Thr Gly Ser Cys Ile
                420                 425                 430

Pro Trp Pro Lys Ala Lys Pro Lys Ala Lys Lys Glu Cys Pro Ala Thr
            435                 440                 445

Cys Val Gly Ser Tyr Glu Cys Arg Asp Leu Glu Gly Cys Val Val Thr
        450                 455                 460

Lys Tyr Asn Asp Thr Cys Gln Pro Lys Val Lys Cys Met Val Pro Tyr
465                 470                 475                 480

Cys Asp Asn Asp Lys Asn Leu Thr Glu Val Cys Lys Gln Lys Ala Asn
                    485                 490                 495

Cys Glu Ala Asp Gln Lys Pro Ser Ser Asp Gly Tyr Cys Trp Ser Tyr
                500                 505                 510

Thr Cys Asp Gln Thr Thr Gly Phe Cys Lys Lys Asp Lys Arg Gly Lys
            515                 520                 525

Glu Met Cys Thr Gly Lys Thr Asn Asn Cys Gln Glu Tyr Val Cys Asp
        530                 535                 540

Ser Glu Gln Arg Cys Ser Val Arg Asp Lys Val Cys Val Lys Thr Ser
545                 550                 555                 560

Pro Tyr Ile Glu Met Ser Cys Tyr Val Ala Lys Cys Asn Leu Asn Thr
                    565                 570                 575

Gly Met Cys Glu Asn Arg Leu Ser Cys Asp Thr Tyr Ser Ser Cys Gly
                580                 585                 590
```

-continued

```
Gly Asp Ser Thr Gly Ser Val Cys Lys Cys Asp Ser Thr Thr Gly Asn
            595                 600                 605
Lys Cys Gln Cys Asn Lys Val Lys Asn Gly Asn Tyr Cys Asn Ser Lys
    610                 615                 620
Asn His Glu Ile Cys Asp Tyr Thr Gly Thr Thr Pro Gln Cys Lys Val
625                 630                 635                 640
Ser Asn Cys Thr Glu Asp Leu Val Arg Asp Gly Cys Leu Ile Lys Arg
                645                 650                 655
Cys Asn Glu Thr Ser Lys Thr Thr Tyr Trp Glu Asn Val Asp Cys Ser
            660                 665                 670
Asn Thr Lys Ile Glu Phe Ala Lys Asp Lys Ser Glu Thr Met Cys
    675                 680                 685
Lys Gln Tyr Tyr Ser Thr Thr Cys Leu Asn Gly Lys Cys Val Val Gln
    690                 695                 700
Ala Val Gly Asp Val Ser Asn Val Gly Cys Gly Tyr Cys Ser Met Gly
705                 710                 715                 720
Thr Asp Asn Ile Ile Thr Tyr His Asp Asp Cys Asn Ser Arg Lys Ser
                725                 730                 735
Gln Cys Gly Asn Phe Asn Gly Lys Cys Ile Lys Gly Ser Asp Asn Ser
            740                 745                 750
Tyr Ser Cys Val Phe Glu Lys Asp Lys Thr Ser Ser Lys Ser Asp Asn
    755                 760                 765
Asp Ile Cys Ala Glu Cys Ser Ser Leu Thr Cys Pro Ala Asp Thr Thr
    770                 775                 780
Tyr Arg Thr Tyr Thr Tyr Asp Ser Lys Thr Gly Thr Cys Lys Ala Thr
785                 790                 795                 800
Val Gln Pro Thr Pro Ala Cys Ser Val Cys Glu Ser Gly Lys Phe Val
                805                 810                 815
Glu Lys Cys Lys Asp Gln Lys Leu Glu Arg Lys Val Thr Leu Glu Asn
            820                 825                 830
Gly Lys Glu Tyr Lys Tyr Thr Ile Pro Lys Asp Cys Val Asn Glu Gln
    835                 840                 845
Cys Ile Pro Arg Thr Tyr Ile Asp Cys Leu Gly Asn Asp Asp Asn Phe
    850                 855                 860
Lys Ser Ile Tyr Asn Phe Tyr Leu Pro Cys Gln Ala Tyr Val Thr Ala
865                 870                 875                 880
Thr Tyr His Tyr Ser Ser Leu Phe Asn Leu Thr Ser Tyr Lys Leu His
                885                 890                 895
Leu Pro Gln Ser Glu Glu Phe Met Lys Glu Ala Asp Lys Glu Ala Tyr
            900                 905                 910
Cys Thr Tyr Glu Ile Thr Thr Arg Glu Cys Lys Thr Cys Ser Leu Ile
    915                 920                 925
Glu Thr Arg Glu Lys Val Gln Glu Val Asp Leu Cys Ala Glu Glu Thr
    930                 935                 940
Lys Asn Gly Gly Val Pro Phe Cys Lys Asn Asn Cys Ile Ile
945                 950                 955                 960
Asp Pro Asn Phe Asp Cys Gln Pro Ile Glu Cys Lys Ile Gln Glu Ile
                965                 970                 975
Val Ile Thr Glu Lys Asp Gly Ile Lys Thr Thr Thr Cys Lys Asn Thr
            980                 985                 990
Thr Lys Ala Thr Cys Asp Thr Asn Asn Lys Arg Ile Glu Asp Ala Arg
    995                 1000                1005
```

```
Lys Ala Phe Ile Glu Gly Lys Glu Gly Ile Glu Gln Val Glu Cys Ala
    1010                1015                1020

Ser Thr Val Cys Gln Asn Asp Asn Ser Cys Pro Ile Ile Thr Asp Val
1025                1030                1035                1040

Glu Lys Cys Asn Gln Asn Thr Glu Val Asp Tyr Gly Cys Lys Ala Met
                1045                1050                1055

Thr Gly Glu Cys Asp Gly Thr Thr Tyr Leu Cys Lys Phe Val Gln Leu
        1060                1065                1070

Thr Asp Asp Pro Ser Leu Asp Ser Glu His Phe Arg Thr Lys Ser Gly
    1075                1080                1085

Val Glu Leu Asn Asn Ala Cys Leu Lys Tyr Lys Cys Val Glu Ser Lys
1090                1095                1100

Gly Ser Asp Gly Lys Ile Thr His Lys Trp Glu Ile Asp Thr Glu Arg
1105                1110                1115                1120

Ser Asn Ala Asn Pro Lys Pro Arg Asn Pro Cys Glu Thr Ala Thr Cys
                1125                1130                1135

Asn Gln Thr Thr Gly Glu Thr Ile Tyr Thr Lys Lys Thr Cys Thr Val
            1140                1145                1150

Ser Glu Phe Pro Thr Ile Thr Pro Asn Gln Gly Arg Cys Phe Tyr Cys
        1155                1160                1165

Gln Cys Ser Tyr Leu Asp Gly Ser Ser Val Leu Thr Met Tyr Gly Glu
    1170                1175                1180

Thr Asp Lys Glu Tyr Tyr Asp Leu Asp Ala Cys Gly Asn Cys Arg Val
1185                1190                1195                1200

Trp Asn Gln Thr Asp Arg Thr Gln Gln Leu Asn Asn His Thr Glu Cys
                1205                1210                1215

Ile Leu Ala Gly Glu Ile Asn Asn Val Gly Ala Ile Ala Ala Ala Thr
            1220                1225                1230

Thr Val Ala Ala Val Ile Val Ala Val Val Ala Leu Ile Val Val
        1235                1240                1245

Ser Ile Gly Leu Phe Lys Thr Tyr Gln Leu Val Ser Ser Ala Met Lys
    1250                1255                1260

Asn Ala Ile Thr Ile Thr Asn Glu Asn Ala Glu Tyr Val Gly Ala Asp
1265                1270                1275                1280

Asn Glu Ala Thr Asn Ala Ala Thr Phe Asn Gly
                1285                1290

(2) INFORMATION FOR SEQ ID NO:4:

(i) SEQUENCE CHARACTERISTICS:
        (A) LENGTH: 4090 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 61..3936

(xi) SEQUENCE DESCRIPTION: SEQ ID NO:4:

TTCTGTTAAA TAGGAAAGGC AAGTGATTTA AACAAGACAA TGAACTAGAA AGACAAAGAT     60

ATG AAA TTA TTA TTA TTA AAT ATC TTA TTA TTA TGT TGT CTT GCA GAT    108
Met Lys Leu Leu Leu Leu Asn Ile Leu Leu Leu Cys Cys Leu Ala Asp
                1300                1305                1310

AAA CTT AAT GAA TTT TCA GCA GAT ATT GAT TAT TAT GAC CTT GGT ATT    156
Lys Leu Asn Glu Phe Ser Ala Asp Ile Asp Tyr Tyr Asp Leu Gly Ile
            1315                1320                1325
```

```
ATG TCT CGT GGA AAG AAT GCA GGT TCA TGG TAT CAT TCT TAT GAA CAT      204
Met Ser Arg Gly Lys Asn Ala Gly Ser Trp Tyr His Ser Tyr Glu His
            1330                1335                1340

CAA TAT GAT GTT TTC TAT TAT TTA GCT ATG CAA CCA TGG AGA CAT TTT      252
Gln Tyr Asp Val Phe Tyr Tyr Leu Ala Met Gln Pro Trp Arg His Phe
            1345                1350                1355

GTA TGG ACT ACT TGT ACA ACA ACT GAT GGC AAT AAA GAA TGT TAT AAA      300
Val Trp Thr Thr Cys Thr Thr Thr Asp Gly Asn Lys Glu Cys Tyr Lys
1360                1365                1370                1375

TAT ACT ATC AAT GAA GAT CAT AAT GTA AAG GTT GAA GAT ATT AAT AAA      348
Tyr Thr Ile Asn Glu Asp His Asn Val Lys Val Glu Asp Ile Asn Lys
            1380                1385                1390

ACA GAT ATT AAA CAA GAT TTT TGT CAA AAA GAA TAT GCA TAT CCA ATT      396
Thr Asp Ile Lys Gln Asp Phe Cys Gln Lys Glu Tyr Ala Tyr Pro Ile
            1395                1400                1405

GAA AAA TAT GAA GTT GAT TGG GAC AAT GTT CCA GTT GAT GAA CAA CGA      444
Glu Lys Tyr Glu Val Asp Trp Asp Asn Val Pro Val Asp Glu Gln Arg
            1410                1415                1420

ATT GAA AGT GTA GAT ATT AAT GGA AAA ACT TGT TTT AAA TAT GCA GCT      492
Ile Glu Ser Val Asp Ile Asn Gly Lys Thr Cys Phe Lys Tyr Ala Ala
            1425                1430                1435

AAA AGA CCA TTG GCT TAT GTT TAT TTA AAT ACA AAA ATG ACA TAT GCA      540
Lys Arg Pro Leu Ala Tyr Val Tyr Leu Asn Thr Lys Met Thr Tyr Ala
1440                1445                1450                1455

ACA AAA ACT GAA GCA TAT GAT GTT TGT AGA ATG GAT TTC ATT GGA GGA      588
Thr Lys Thr Glu Ala Tyr Asp Val Cys Arg Met Asp Phe Ile Gly Gly
            1460                1465                1470

AGA TCA ATT ACA TTC AGA TCA TTT AAC ACA GAG AAT AAA GCA TTT ATT      636
Arg Ser Ile Thr Phe Arg Ser Phe Asn Thr Glu Asn Lys Ala Phe Ile
            1475                1480                1485

GAT CAA TAT AAT ACA AAC ACT ACA TCA AAA TGT CTT CTT AAA GTA TAT      684
Asp Gln Tyr Asn Thr Asn Thr Thr Ser Lys Cys Leu Leu Lys Val Tyr
            1490                1495                1500

GAT AAT AAT GTT AAT ACA CAT CTT GCA ATT ATC TTT GGT ATT ACT GAT      732
Asp Asn Asn Val Asn Thr His Leu Ala Ile Ile Phe Gly Ile Thr Asp
            1505                1510                1515

TCT ACA GTC ATT AAA TCA CTT CAA GAG AAC TTA TCT CTT TTA AAT AAA      780
Ser Thr Val Ile Lys Ser Leu Gln Glu Asn Leu Ser Leu Leu Asn Lys
1520                1525                1530                1535

TTA ACA ACA GTC AAA GGA GTA ACA CTC TAC TAT CTT AAA GAT GAT ACT      828
Leu Thr Thr Val Lys Gly Val Thr Leu Tyr Tyr Leu Lys Asp Asp Thr
            1540                1545                1550

TAT TTT ACA GTT AAT ATT ACT TTA AAT GAT TTG AAA TAT GAG ACA CTT      876
Tyr Phe Thr Val Asn Ile Thr Leu Asn Asp Leu Lys Tyr Glu Thr Leu
            1555                1560                1565

GTC CAA TAC ACA GCA GGA ACA GGA CAA GTT GAT CCA CTT ATT AAT ATT      924
Val Gln Tyr Thr Ala Gly Thr Gly Gln Val Asp Pro Leu Ile Asn Ile
            1570                1575                1580

GCT AAG AAT GAC TTA ACT GCT AAA GTT GCA GAT AAA AGT AAA GAT AAA      972
Ala Lys Asn Asp Leu Thr Ala Lys Val Ala Asp Lys Ser Lys Asp Lys
1585                1590                1595

AAT GCA AAT GAT AAA ATC AAA AGA GGA ACT ATG ATT GTG TTA ATG GAT     1020
Asn Ala Asn Asp Lys Ile Lys Arg Gly Thr Met Ile Val Leu Met Asp
1600                1605                1610                1615

ACT GCA CTT GGA TCA GAA TTT AAT GCG GAA ACA GAA TTT GAT AGA AAG     1068
Thr Ala Leu Gly Ser Glu Phe Asn Ala Glu Thr Glu Phe Asp Arg Lys
            1620                1625                1630

AAT ATT TCA GTT CAT ACT GTT GTT CTT AAT AGA AAT AAA GAC CCA AAG     1116
Asn Ile Ser Val His Thr Val Val Leu Asn Arg Asn Lys Asp Pro Lys
            1635                1640                1645
```

```
ATT ACA CGT AGT GCA TTG AGA CTT GTT TCA CTT GGA CCA CAT TAT CAT    1164
Ile Thr Arg Ser Ala Leu Arg Leu Val Ser Leu Gly Pro His Tyr His
        1650                1655                1660

GAA TTT ACA GGT AAT GAT GAA GTT AAT GCA ACA ATC ACT GCA CTT TTC    1212
Glu Phe Thr Gly Asn Asp Glu Val Asn Ala Thr Ile Thr Ala Leu Phe
            1665                1670                1675

AAA GGA ATT AGA GCC AAT TTA ACA GAA AGA TGT GAT AGA GAT AAA TGT    1260
Lys Gly Ile Arg Ala Asn Leu Thr Glu Arg Cys Asp Arg Asp Lys Cys
1680                1685                1690                1695

TCA GGA TTT TGT GAT GCA ATG AAT AGA TGC ACA TGT CCA ATG TGT TGT    1308
Ser Gly Phe Cys Asp Ala Met Asn Arg Cys Thr Cys Pro Met Cys Cys
                1700                1705                1710

GAG AAT GAT TGT TTC TAT ACA TCC TGT GAT GTA GAA ACA GGA TCA TGT    1356
Glu Asn Asp Cys Phe Tyr Thr Ser Cys Asp Val Glu Thr Gly Ser Cys
            1715                1720                1725

ATT CCA TGG CCT AAA GCT AAA CCA AAA GCA AAG AAA GAA TGT CCA GCA    1404
Ile Pro Trp Pro Lys Ala Lys Pro Lys Ala Lys Lys Glu Cys Pro Ala
        1730                1735                1740

ACA TGT GTA GGC TCA TAT GAA TGT AGA GAT CTT GAA GGA TGT GTT GTT    1452
Thr Cys Val Gly Ser Tyr Glu Cys Arg Asp Leu Glu Gly Cys Val Val
        1745                1750                1755

AAA CAA TAT AAT ACA TCT TGT GAA CCA AAA GTG AAA TGC ATG GTA CCA    1500
Lys Gln Tyr Asn Thr Ser Cys Glu Pro Lys Val Lys Cys Met Val Pro
1760                1765                1770                1775

TAT TGT GAT AAT GAT AAG AAT CTA ACT GAA GTA TGT AAA CAA AAA GCT    1548
Tyr Cys Asp Asn Asp Lys Asn Leu Thr Glu Val Cys Lys Gln Lys Ala
                1780                1785                1790

AAT TGT GAA GCA GAT CAA AAA CCA AGT TCT GAT GGA TAT TGT TGG AGT    1596
Asn Cys Glu Ala Asp Gln Lys Pro Ser Ser Asp Gly Tyr Cys Trp Ser
            1795                1800                1805

TAT ACA TGT GAC CAA ACT ACT GGT TTT TGT AAG AAA GAT AAA CGT GGT    1644
Tyr Thr Cys Asp Gln Thr Thr Gly Phe Cys Lys Lys Asp Lys Arg Gly
        1810                1815                1820

GAA AAT ATG TGT ACA GGA AAG ACA AAT AAC TGT CAA GAA TAT GTT TGT    1692
Glu Asn Met Cys Thr Gly Lys Thr Asn Asn Cys Gln Glu Tyr Val Cys
        1825                1830                1835

GAT GAA AAA CAA AGA TGT ACT GTT CAA GAA AAG GTA TGT GTA AAA ACA    1740
Asp Glu Lys Gln Arg Cys Thr Val Gln Glu Lys Val Cys Val Lys Thr
1840                1845                1850                1855

TCA CCT TAT ATT GAA ATG TCA TGT TAT GTA GCC AAG TGT AAT CTC AAT    1788
Ser Pro Tyr Ile Glu Met Ser Cys Tyr Val Ala Lys Cys Asn Leu Asn
                1860                1865                1870

ACA GGT ATG TGT GAG AAC AGA TTA TCA TGT GAT ACA TAC TCA TCA TGT    1836
Thr Gly Met Cys Glu Asn Arg Leu Ser Cys Asp Thr Tyr Ser Ser Cys
            1875                1880                1885

GGT GGA GAT TCT ACA GGA TCA GTA TGT AAA TGT GAT TCT ACA ACT AAT    1884
Gly Gly Asp Ser Thr Gly Ser Val Cys Lys Cys Asp Ser Thr Thr Asn
        1890                1895                1900

AAC CAA TGT CAA TGT ACT CAA GTA AAA AAC GGT AAT TAT TGT GAT TCT    1932
Asn Gln Cys Gln Cys Thr Gln Val Lys Asn Gly Asn Tyr Cys Asp Ser
        1905                1910                1915

AAT AAA CAT CAA ATT TGT GAT TAT ACA GGA AAA ACA CCA CAA TGT AAA    1980
Asn Lys His Gln Ile Cys Asp Tyr Thr Gly Lys Thr Pro Gln Cys Lys
1920                1925                1930                1935

GTG TCT AAT TGT ACA GAA GAT CTT GTT AGA GAT GGA TGT CTT ATT AAG    2028
Val Ser Asn Cys Thr Glu Asp Leu Val Arg Asp Gly Cys Leu Ile Lys
                1940                1945                1950

AGA TGT AAT GAA ACA AGT AAA ACA ACA TAT TGG GAG AAT GTT GAT TGT    2076
Arg Cys Asn Glu Thr Ser Lys Thr Thr Tyr Trp Glu Asn Val Asp Cys
```

-continued

```
           1955                 1960                 1965
TCT AAA ACT GAA GTT AAA TTC GCT CAA GAT GGT AAA TCT GAA AAT ATG        2124
Ser Lys Thr Glu Val Lys Phe Ala Gln Asp Gly Lys Ser Glu Asn Met
            1970                1975                1980

TGT AAA CAA TAT TAT TCA ACT ACA TGT TTG AAT GGA CAA TGT GTT GTT        2172
Cys Lys Gln Tyr Tyr Ser Thr Thr Cys Leu Asn Gly Gln Cys Val Val
        1985                1990                1995

CAA GCA GTT GGT GAT GTT TCT AAT GTA GGA TGT GGA TAT TGT TCA ATG        2220
Gln Ala Val Gly Asp Val Ser Asn Val Gly Cys Gly Tyr Cys Ser Met
2000                2005                2010                2015

GGA ACA GAT AAT ATT ATT ACA TAT CAT GAT GAT TGT AAT TCA CGT AAA        2268
Gly Thr Asp Asn Ile Ile Thr Tyr His Asp Asp Cys Asn Ser Arg Lys
                2020                2025                2030

TCA CAA TGT GGA AAC TTT AAT GGT AAG TGT GTA GAA AAT AGT GAC AAA        2316
Ser Gln Cys Gly Asn Phe Asn Gly Lys Cys Val Glu Asn Ser Asp Lys
            2035                2040                2045

TCA TAT TCT TGT GTA TTT AAT AAG GAT GTT TCT TCT ACA TCA GAT AAT        2364
Ser Tyr Ser Cys Val Phe Asn Lys Asp Val Ser Ser Thr Ser Asp Asn
        2050                2055                2060

GAT ATT TGT GCA AAA TGT TCT AGT TTA ACA TGT CCA GCT GAT ACT ACA        2412
Asp Ile Cys Ala Lys Cys Ser Ser Leu Thr Cys Pro Ala Asp Thr Thr
    2065                2070                2075

TAC AGA ACA TAT ACA TAT GAC TCA AAA ACA GGA ACA TGT AAA GCA ACT        2460
Tyr Arg Thr Tyr Thr Tyr Asp Ser Lys Thr Gly Thr Cys Lys Ala Thr
2080                2085                2090                2095

GTT CAA CCA ACA CCA GCA TGT TCA GTA TGT GAA AGT GGT AAA TTT GTA        2508
Val Gln Pro Thr Pro Ala Cys Ser Val Cys Glu Ser Gly Lys Phe Val
                2100                2105                2110

GAA AAA TGC AAA GAT CAA AAA TTA GAA CGT AAA GTT ACT TTA GAA AAT        2556
Glu Lys Cys Lys Asp Gln Lys Leu Glu Arg Lys Val Thr Leu Glu Asn
            2115                2120                2125

GGA AAA GAA TAT AAA TAC ACC ATT CCA AAA GAT TGT GTC AAT GAA CAA        2604
Gly Lys Glu Tyr Lys Tyr Thr Ile Pro Lys Asp Cys Val Asn Glu Gln
        2130                2135                2140

TGC ATT CCA AGA ACA TAC ATA GAT TGT TTA GGT AAT GAT GAT AAC TTT        2652
Cys Ile Pro Arg Thr Tyr Ile Asp Cys Leu Gly Asn Asp Asp Asn Phe
    2145                2150                2155

AAA TCT ATT TAT AAC TTC TAT TTA CCA TGT CAA GCA TAT GTT ACA GCT        2700
Lys Ser Ile Tyr Asn Phe Tyr Leu Pro Cys Gln Ala Tyr Val Thr Ala
2160                2165                2170                2175

ACC TAT CAT TAC AGT TCA TTA TTC AAT TTA ACT AGT TAT AAA CTT CAT        2748
Thr Tyr His Tyr Ser Ser Leu Phe Asn Leu Thr Ser Tyr Lys Leu His
                2180                2185                2190

TTA CCA CAA AGT GAA GAA TTT ATG AAA GAG GCA GAC AAA GAA GCA TAT        2796
Leu Pro Gln Ser Glu Glu Phe Met Lys Glu Ala Asp Lys Glu Ala Tyr
        2195                2200                2205

TGT ACA TAC GAA ATA ACA ACA AGA GAA TGT AAA ACA TGT TCA TTA ATT        2844
Cys Thr Tyr Glu Ile Thr Thr Arg Glu Cys Lys Thr Cys Ser Leu Ile
    2210                2215                2220

GAA ACT AGA GAA AAA GTC CAA GAA GTT GAT TTG TGT GCA GAA GAG ACT        2892
Glu Thr Arg Glu Lys Val Gln Glu Val Asp Leu Cys Ala Glu Glu Thr
2225                2230                2235

AAG AAT GGA GGA GTT CCA TTC AAA TGT AAG AAT AAC AAT TGC ATT ATT        2940
Lys Asn Gly Gly Val Pro Phe Lys Cys Lys Asn Asn Asn Cys Ile Ile
2240                2245                2250                2255

GAT CCT AAC TTT GAT TGT CAA CCT ATT GAA TGT AAG ATT CAA GAG ATT        2988
Asp Pro Asn Phe Asp Cys Gln Pro Ile Glu Cys Lys Ile Gln Glu Ile
                2260                2265                2270

GTT ATT ACA GAA AAA GAT GGA ATA AAA ACA ACA ACA TGT AAA AAT ACC        3036
```

-continued

```
                Val Ile Thr Glu Lys Asp Gly Ile Lys Thr Thr Thr Cys Lys Asn Thr
                                2275                2280                2285

ACA AAA ACA ACA TGT GAC ACT AAC AAT AAG AGA ATA GAA GAT GCA CGT                  3084
Thr Lys Thr Thr Cys Asp Thr Asn Asn Lys Arg Ile Glu Asp Ala Arg
            2290                2295                2300

AAA GCA TTC ATT GAA GGA AAA GAA GGA ATT GAG CAA GTA GAA TGT GCA                  3132
Lys Ala Phe Ile Glu Gly Lys Glu Gly Ile Glu Gln Val Glu Cys Ala
        2305                2310                2315

AGT ACT GTT TGT CAA AAT GAT AAT AGT TGT CCA ATT ATT ACT GAT GTA                  3180
Ser Thr Val Cys Gln Asn Asp Asn Ser Cys Pro Ile Ile Thr Asp Val
2320                2325                2330                2335

GAA AAA TGT AAT CAA AAC ACA GAA GTA GAT TAT GGA TGT AAA GCA ATG                  3228
Glu Lys Cys Asn Gln Asn Thr Glu Val Asp Tyr Gly Cys Lys Ala Met
            2340                2345                2350

ACA GGA GAA TGT GAT GGT ACT ACA TAT CTT TGT AAA TTT GTA CAA CTT                  3276
Thr Gly Glu Cys Asp Gly Thr Thr Tyr Leu Cys Lys Phe Val Gln Leu
        2355                2360                2365

ACT GAT GAT CCA TCA TTA GAT AGT GAA CAT TTT AGA ACT AAA TCA GGA                  3324
Thr Asp Asp Pro Ser Leu Asp Ser Glu His Phe Arg Thr Lys Ser Gly
    2370                2375                2380

GTT GAA CTT AAC AAT GCA TGT TTG AAA TAT AAA TGT GTT GAG AGT AAA                  3372
Val Glu Leu Asn Asn Ala Cys Leu Lys Tyr Lys Cys Val Glu Ser Lys
        2385                2390                2395

GGA AGT GAT GGA AAA ATC ACA CAT AAA TGG GAA ATT GAT ACA GAA CGA                  3420
Gly Ser Asp Gly Lys Ile Thr His Lys Trp Glu Ile Asp Thr Glu Arg
2400                2405                2410                2415

TCA AAT GCT AAT CCA AAA CCA AGA AAT CCA TGC GAA ACC GCA ACA TGT                  3468
Ser Asn Ala Asn Pro Lys Pro Arg Asn Pro Cys Glu Thr Ala Thr Cys
            2420                2425                2430

AAT CAA ACA ACT GGA GAA ACT ATT TAC ACA AAG AAA ACA TGT ACT GTT                  3516
Asn Gln Thr Thr Gly Glu Thr Ile Tyr Thr Lys Lys Thr Cys Thr Val
        2435                2440                2445

TCA GAA GAA TTC CCA ACA ATC ACA CCA AAT CAA GGA AGA TGT TTC TAT                  3564
Ser Glu Glu Phe Pro Thr Ile Thr Pro Asn Gln Gly Arg Cys Phe Tyr
    2450                2455                2460

TGT CAA TGT TCA TAT CTT GAC GGT TCA TCA GTT CTT ACT ATG TAT GGA                  3612
Cys Gln Cys Ser Tyr Leu Asp Gly Ser Ser Val Leu Thr Met Tyr Gly
        2465                2470                2475

GAA ACA GAT AAA GAA TAT TAT GAT CTT GAT GCA TGT GGT AAT TGT CGT                  3660
Glu Thr Asp Lys Glu Tyr Tyr Asp Leu Asp Ala Cys Gly Asn Cys Arg
2480                2485                2490                2495

GTT TGG AAT CAG ACA GAT AGA ACA CAA CAA CTT AAT AAT CAC ACC GAG                  3708
Val Trp Asn Gln Thr Asp Arg Thr Gln Gln Leu Asn Asn His Thr Glu
            2500                2505                2510

TGT ATT CTC GCA GGA GAA ATT AAT AAT GTT GGA GCT ATT GCA GCG GCA                  3756
Cys Ile Leu Ala Gly Glu Ile Asn Asn Val Gly Ala Ile Ala Ala Ala
        2515                2520                2525

ACT ACT GTG GCT GTA GTT GTA GTT GCA GTC GTA GTT GCA TTA ATT GTT                  3804
Thr Thr Val Ala Val Val Val Val Ala Val Val Val Ala Leu Ile Val
    2530                2535                2540

GTT TCT ATT GGA TTA TTT AAG ACT TAT CAA CTT GTT TCA TCA GCT ATG                  3852
Val Ser Ile Gly Leu Phe Lys Thr Tyr Gln Leu Val Ser Ser Ala Met
        2545                2550                2555

AAG AAT GCC ATT ACA ATA ACT AAT GAA AAT GCA GAA TAT GTT GGA GCA                  3900
Lys Asn Ala Ile Thr Ile Thr Asn Glu Asn Ala Glu Tyr Val Gly Ala
2560                2565                2570                2575

GAT AAT GAA GCA ACT AAT GCA GCA ACA TTC AAT GGA TAAGAACAAT                       3946
Asp Asn Glu Ala Thr Asn Ala Ala Thr Phe Asn Gly
            2580                2585
```

AATTAAGAGA ATTGAATAAC ATTTTATGTT TTTAGATTAA AAATAAAAAG AAGAATAAAT    4006

TGAGTGATAA ACAATGAATA AAATAAATAA AAATAAACAA GAATAAAGTG AACATCATTT    4066

TTATTTTCAT ATTTTAACAA CACT    4090

(2) INFORMATION FOR SEQ ID NO:5:

(i) SEQUENCE CHARACTERISTICS:
        (A) LENGTH: 1292 amino acids
        (B) TYPE: amino acid
        (D) TOPOLOGY: linear (ii) MOLECULE TYPE: protein (xi) SEQUENCE DESCRIPTION: SEQ ID NO:5:

```
Met Lys Leu Leu Leu Asn Ile Leu Leu Cys Cys Leu Ala Asp
  1               5                  10                  15

Lys Leu Asn Glu Phe Ser Ala Asp Ile Asp Tyr Tyr Asp Leu Gly Ile
            20                  25                  30

Met Ser Arg Gly Lys Asn Ala Gly Ser Trp Tyr His Ser Tyr Glu His
        35                  40                  45

Gln Tyr Asp Val Phe Tyr Tyr Leu Ala Met Gln Pro Trp Arg His Phe
    50                  55                  60

Val Trp Thr Thr Cys Thr Thr Thr Asp Gly Asn Lys Glu Cys Tyr Lys
 65                  70                  75                  80

Tyr Thr Ile Asn Glu Asp His Asn Val Lys Val Glu Asp Ile Asn Lys
                 85                  90                  95

Thr Asp Ile Lys Gln Asp Phe Cys Gln Lys Glu Tyr Ala Tyr Pro Ile
            100                 105                 110

Glu Lys Tyr Glu Val Asp Trp Asp Asn Val Pro Val Asp Glu Gln Arg
        115                 120                 125

Ile Glu Ser Val Asp Ile Asn Gly Lys Thr Cys Phe Lys Tyr Ala Ala
    130                 135                 140

Lys Arg Pro Leu Ala Tyr Val Tyr Leu Asn Thr Lys Met Thr Tyr Ala
145                 150                 155                 160

Thr Lys Thr Glu Ala Tyr Asp Val Cys Arg Met Asp Phe Ile Gly Gly
                165                 170                 175

Arg Ser Ile Thr Phe Arg Ser Phe Asn Thr Glu Asn Lys Ala Phe Ile
            180                 185                 190

Asp Gln Tyr Asn Thr Asn Thr Thr Ser Lys Cys Leu Leu Lys Val Tyr
        195                 200                 205

Asp Asn Asn Val Asn Thr His Leu Ala Ile Ile Phe Gly Ile Thr Asp
    210                 215                 220

Ser Thr Val Ile Lys Ser Leu Gln Glu Asn Leu Ser Leu Leu Asn Lys
225                 230                 235                 240

Leu Thr Thr Val Lys Gly Val Thr Leu Tyr Tyr Leu Lys Asp Asp Thr
                245                 250                 255

Tyr Phe Thr Val Asn Ile Thr Leu Asn Asp Leu Lys Tyr Glu Thr Leu
            260                 265                 270

Val Gln Tyr Thr Ala Gly Thr Gly Gln Val Asp Pro Leu Ile Asn Ile
        275                 280                 285

Ala Lys Asn Asp Leu Thr Ala Lys Val Ala Asp Lys Ser Lys Asp Lys
    290                 295                 300

Asn Ala Asn Asp Lys Ile Lys Arg Gly Thr Met Ile Val Leu Met Asp
305                 310                 315                 320

Thr Ala Leu Gly Ser Glu Phe Asn Ala Glu Thr Glu Phe Asp Arg Lys
```

-continued

```
                    325                 330                 335
Asn Ile Ser Val His Thr Val Leu Asn Arg Asn Lys Asp Pro Lys
                340                 345                 350
Ile Thr Arg Ser Ala Leu Arg Leu Val Ser Leu Gly Pro His Tyr His
                355                 360                 365
Glu Phe Thr Gly Asn Asp Glu Val Asn Ala Thr Ile Thr Ala Leu Phe
    370                 375                 380
Lys Gly Ile Arg Ala Asn Leu Thr Glu Arg Cys Asp Arg Asp Lys Cys
385                 390                 395                 400
Ser Gly Phe Cys Asp Ala Met Asn Arg Cys Thr Cys Pro Met Cys Cys
                405                 410                 415
Glu Asn Asp Cys Phe Tyr Thr Ser Cys Asp Val Glu Thr Gly Ser Cys
                420                 425                 430
Ile Pro Trp Pro Lys Ala Lys Pro Lys Ala Lys Lys Glu Cys Pro Ala
                435                 440                 445
Thr Cys Val Gly Ser Tyr Glu Cys Arg Asp Leu Glu Gly Cys Val Val
                450                 455                 460
Lys Gln Tyr Asn Thr Ser Cys Glu Pro Lys Val Lys Cys Met Val Pro
465                 470                 475                 480
Tyr Cys Asp Asn Asp Lys Asn Leu Thr Glu Val Cys Lys Gln Lys Ala
                485                 490                 495
Asn Cys Glu Ala Asp Gln Lys Pro Ser Ser Asp Gly Tyr Cys Trp Ser
                500                 505                 510
Tyr Thr Cys Asp Gln Thr Thr Gly Phe Cys Lys Lys Asp Lys Arg Gly
                515                 520                 525
Glu Asn Met Cys Thr Gly Lys Thr Asn Asn Cys Gln Glu Tyr Val Cys
                530                 535                 540
Asp Glu Lys Gln Arg Cys Thr Val Gln Glu Lys Val Cys Val Lys Thr
545                 550                 555                 560
Ser Pro Tyr Ile Glu Met Ser Cys Tyr Val Ala Lys Cys Asn Leu Asn
                565                 570                 575
Thr Gly Met Cys Glu Asn Arg Leu Ser Cys Asp Thr Tyr Ser Ser Cys
                580                 585                 590
Gly Gly Asp Ser Thr Gly Ser Val Cys Lys Cys Asp Ser Thr Thr Asn
                595                 600                 605
Asn Gln Cys Gln Cys Thr Gln Val Lys Asn Gly Asn Tyr Cys Asp Ser
                610                 615                 620
Asn Lys His Gln Ile Cys Asp Tyr Thr Gly Lys Thr Pro Gln Cys Lys
625                 630                 635                 640
Val Ser Asn Cys Thr Glu Asp Leu Val Arg Asp Gly Cys Leu Ile Lys
                645                 650                 655
Arg Cys Asn Glu Thr Ser Lys Thr Thr Tyr Trp Glu Asn Val Asp Cys
                660                 665                 670
Ser Lys Thr Glu Val Lys Phe Ala Gln Asp Gly Lys Ser Glu Asn Met
                675                 680                 685
Cys Lys Gln Tyr Tyr Ser Thr Cys Leu Asn Gly Gln Cys Val Val
                690                 695                 700
Gln Ala Val Gly Asp Val Ser Asn Val Gly Cys Gly Tyr Cys Ser Met
705                 710                 715                 720
Gly Thr Asp Asn Ile Ile Thr Tyr His Asp Asp Cys Asn Ser Arg Lys
                725                 730                 735
Ser Gln Cys Gly Asn Phe Asn Gly Lys Cys Val Glu Asn Ser Asp Lys
                740                 745                 750
```

```
Ser Tyr Ser Cys Val Phe Asn Lys Asp Val Ser Ser Thr Ser Asp Asn
        755                 760                 765

Asp Ile Cys Ala Lys Cys Ser Ser Leu Thr Cys Pro Ala Asp Thr Thr
        770                 775                 780

Tyr Arg Thr Tyr Thr Tyr Asp Ser Lys Thr Gly Thr Cys Lys Ala Thr
785             790                 795                     800

Val Gln Pro Thr Pro Ala Cys Ser Val Cys Glu Ser Gly Lys Phe Val
                805                 810                 815

Glu Lys Cys Lys Asp Gln Lys Leu Glu Arg Lys Val Thr Leu Glu Asn
                820                 825                 830

Gly Lys Glu Tyr Lys Tyr Thr Ile Pro Lys Asp Cys Val Asn Glu Gln
                835                 840                 845

Cys Ile Pro Arg Thr Tyr Ile Asp Cys Leu Gly Asn Asp Asp Asn Phe
        850                 855                 860

Lys Ser Ile Tyr Asn Phe Tyr Leu Pro Cys Gln Ala Tyr Val Thr Ala
865             870                 875                     880

Thr Tyr His Tyr Ser Ser Leu Phe Asn Leu Thr Ser Tyr Lys Leu His
                885                 890                 895

Leu Pro Gln Ser Glu Glu Phe Met Lys Glu Ala Asp Lys Glu Ala Tyr
                900                 905                 910

Cys Thr Tyr Glu Ile Thr Thr Arg Glu Cys Lys Thr Cys Ser Leu Ile
        915                 920                 925

Glu Thr Arg Glu Lys Val Gln Glu Val Asp Leu Cys Ala Glu Glu Thr
        930                 935                 940

Lys Asn Gly Gly Val Pro Phe Lys Cys Lys Asn Asn Cys Ile Ile
945                 950                 955                 960

Asp Pro Asn Phe Asp Cys Gln Pro Ile Glu Cys Lys Ile Gln Glu Ile
                965                 970                 975

Val Ile Thr Glu Lys Asp Gly Ile Lys Thr Thr Thr Cys Lys Asn Thr
                980                 985                 990

Thr Lys Thr Thr Cys Asp Thr Asn Asn Lys Arg Ile Glu Asp Ala Arg
                995                1000                1005

Lys Ala Phe Ile Glu Gly Lys Glu Gly Ile Glu Gln Val Glu Cys Ala
        1010                1015                1020

Ser Thr Val Cys Gln Asn Asp Asn Ser Cys Pro Ile Ile Thr Asp Val
1025                1030                1035                1040

Glu Lys Cys Asn Gln Asn Thr Gly Val Asp Tyr Gly Cys Lys Ala Met
                1045                1050                1055

Thr Gly Glu Cys Asp Gly Thr Thr Tyr Leu Cys Lys Phe Val Gln Leu
                1060                1065                1070

Thr Asp Asp Pro Ser Leu Asp Ser Glu His Phe Arg Thr Lys Ser Gly
        1075                1080                1085

Val Glu Leu Asn Asn Ala Cys Leu Lys Tyr Lys Cys Val Glu Ser Lys
        1090                1095                1100

Gly Ser Asp Gly Lys Ile Thr His Lys Trp Glu Ile Asp Thr Glu Arg
1105                1110                1115                1120

Ser Asn Ala Asn Pro Lys Pro Arg Asn Pro Cys Glu Thr Ala Thr Cys
                1125                1130                1135

Asn Gln Thr Thr Gly Glu Thr Ile Tyr Thr Lys Lys Thr Cys Thr Val
                1140                1145                1150

Ser Glu Glu Phe Pro Thr Ile Thr Pro Asn Gln Gly Arg Cys Phe Tyr
                1155                1160                1165
```

-continued

```
Cys Gln Cys Ser Tyr Leu Asp Gly Ser Ser Val Leu Thr Met Tyr Gly
        1170                1175                1180
Glu Thr Asp Lys Glu Tyr Tyr Asp Leu Asp Ala Cys Gly Asn Cys Arg
1185                1190                1195                1200
Val Trp Asn Gln Thr Asp Arg Thr Gln Gln Leu Asn Asn His Thr Glu
                1205                1210                1215
Cys Ile Leu Ala Gly Glu Ile Asn Asn Val Gly Ala Ile Ala Ala Ala
        1220                1225                1230
Thr Thr Val Ala Val Val Val Ala Val Val Ala Leu Ile Val
                1235                1240                1245
Val Ser Ile Gly Leu Phe Lys Thr Tyr Gln Leu Val Ser Ser Ala Met
        1250                1255                1260
Lys Asn Ala Ile Thr Ile Thr Asn Glu Asn Ala Glu Tyr Val Gly Ala
1265                1270                1275                1280
Asp Asn Glu Ala Thr Asn Ala Ala Thr Phe Asn Gly
                1285                1290
```

(2) INFORMATION FOR SEQ ID NO:6:

(i) SEQUENCE CHARACTERISTICS:
        (A) LENGTH: 1292 amino acids
        (B) TYPE: amino acid
        (C) STRANDEDNESS: single
        (D) TOPOLOGY: linear (xi) SEQUENCE DESCRIPTION: SEQ ID NO:6:

```
Met Lys Leu Leu Leu Leu Asn Ile Leu Leu Leu Cys Cys Leu Ala Asp
1               5                   10                  15
Lys Leu Asn Glu Phe Ser Ala Asp Ile Asp Tyr Tyr Asp Leu Gly Ile
                20                  25                  30
Met Ser Arg Gly Lys Asn Ala Gly Ser Trp Tyr His Ser Tyr Glu His
            35                  40                  45
Gln Tyr Asp Val Phe Tyr Tyr Leu Ala Met Gln Pro Trp Arg His Phe
    50                  55                  60
Val Trp Thr Thr Cys Thr Thr Thr Asp Gly Asn Lys Glu Cys Tyr Lys
65                  70                  75                  80
Tyr Thr Ile Asn Glu Asp His Asn Val Lys Val Glu Asp Ile Asn Lys
                85                  90                  95
Thr Asp Ile Lys Gln Asp Phe Cys Gln Lys Glu Tyr Ala Tyr Pro Ile
            100                 105                 110
Glu Lys Tyr Glu Val Asp Trp Asp Asn Val Pro Val Asp Glu Gln Arg
    115                 120                 125
Ile Glu Ser Val Asp Ile Asn Gly Lys Thr Cys Phe Lys Tyr Ala Ala
    130                 135                 140
Lys Arg Pro Leu Ala Tyr Val Tyr Leu Asn Thr Lys Met Thr Tyr Ala
145                 150                 155                 160
Thr Lys Thr Glu Ala Tyr Asp Val Cys Arg Met Asp Phe Ile Gly Gly
                165                 170                 175
Arg Ser Ile Thr Phe Arg Ser Phe Asn Thr Glu Asn Lys Ala Phe Ile
            180                 185                 190
Asp Gln Tyr Asn Thr Asn Thr Thr Ser Lys Cys Leu Leu Lys Val Tyr
    195                 200                 205
Asp Asn Asn Val Asn Thr His Leu Ala Ile Ile Phe Gly Ile Thr Asp
    210                 215                 220
Ser Thr Val Ile Lys Ser Leu Gln Glu Asn Leu Ser Leu Leu Asn Lys
225                 230                 235                 240
```

```
Leu Thr Thr Val Lys Gly Val Thr Leu Tyr Tyr Leu Lys Asp Asp Thr
                245                 250                 255

Tyr Phe Thr Val Asn Ile Thr Leu Asn Asp Leu Lys Tyr Glu Thr Leu
                260                 265                 270

Val Gln Tyr Thr Ala Gly Thr Gly Gln Val Asp Pro Leu Ile Asn Ile
                275                 280             285

Ala Lys Asn Asp Leu Thr Ala Lys Val Ala Asp Lys Ser Lys Asp Lys
            290                 295                 300

Asn Ala Asn Asp Lys Ile Lys Arg Gly Thr Met Ile Val Leu Met Asp
305                 310                 315                 320

Thr Ala Leu Gly Ser Glu Phe Asn Ala Glu Thr Glu Phe Asp Arg Lys
                325                 330                 335

Asn Ile Ser Val His Thr Val Leu Asn Arg Asn Lys Asp Pro Lys
                340                 345                 350

Ile Thr Arg Ser Ala Leu Arg Leu Val Ser Leu Gly Pro His Tyr His
                355                 360                 365

Glu Phe Thr Gly Asn Asp Glu Val Asn Ala Thr Ile Thr Ala Leu Phe
        370                 375                 380

Lys Gly Ile Arg Ala Asn Leu Thr Glu Arg Cys Asp Arg Asp Lys Cys
385                 390                 395                 400

Ser Gly Phe Cys Asp Ala Met Asn Arg Cys Thr Cys Pro Met Cys Cys
                405                 410                 415

Glu Asn Asp Cys Phe Tyr Thr Ser Cys Asp Val Glu Thr Gly Ser Cys
                420                 425                 430

Ile Pro Trp Pro Lys Ala Lys Pro Lys Ala Lys Lys Glu Cys Pro Ala
                435                 440                 445

Thr Cys Val Gly Ser Tyr Glu Cys Arg Asp Leu Glu Gly Cys Val Val
                450                 455                 460

Lys Gln Tyr Asn Thr Ser Cys Glu Pro Lys Val Lys Cys Met Val Pro
465                 470                 475                 480

Tyr Cys Asp Asn Asp Lys Asn Leu Thr Glu Val Cys Lys Gln Lys Ala
                485                 490                 495

Asn Cys Glu Ala Asp Gln Lys Pro Ser Ser Asp Gly Tyr Cys Trp Ser
            500                 505                 510

Tyr Thr Cys Asp Gln Thr Thr Gly Phe Cys Lys Lys Asp Lys Arg Gly
            515                 520                 525

Glu Asn Met Cys Thr Gly Lys Thr Asn Asn Cys Gln Glu Tyr Val Cys
        530                 535                 540

Asp Glu Lys Gln Arg Cys Thr Val Gln Glu Lys Val Cys Val Lys Thr
545                 550                 555                 560

Ser Pro Tyr Ile Glu Met Ser Cys Tyr Val Ala Lys Cys Asn Leu Asn
                565                 570                 575

Thr Gly Met Cys Glu Asn Arg Leu Ser Cys Asp Thr Tyr Ser Ser Cys
                580                 585                 590

Gly Gly Asp Ser Thr Gly Ser Val Cys Lys Cys Asp Ser Thr Thr Asn
                595                 600                 605

Asn Gln Cys Gln Cys Thr Gln Val Lys Asn Gly Asn Tyr Cys Asp Ser
                610                 615                 620

Asn Lys His Gln Ile Cys Asp Tyr Thr Gly Lys Thr Pro Gln Cys Lys
625                 630                 635                 640

Val Ser Asn Cys Thr Glu Asp Leu Val Arg Asp Gly Cys Leu Ile Lys
                645                 650                 655
```

-continued

```
Arg Cys Asn Glu Thr Ser Lys Thr Thr Tyr Trp Glu Asn Val Asp Cys
            660                 665                 670

Ser Lys Thr Glu Val Lys Phe Ala Gln Asp Gly Lys Ser Glu Asn Met
        675                 680                 685

Cys Lys Gln Tyr Tyr Ser Thr Thr Cys Leu Asn Gly Gln Cys Val Val
    690                 695                 700

Gln Ala Val Gly Asp Val Ser Asn Val Gly Cys Gly Tyr Cys Ser Met
705                 710                 715                 720

Gly Thr Asp Asn Ile Ile Thr Tyr His Asp Asp Cys Asn Ser Arg Lys
                725                 730                 735

Ser Gln Cys Gly Asn Phe Asn Gly Lys Cys Val Glu Asn Ser Asp Lys
            740                 745                 750

Ser Tyr Ser Cys Val Phe Asn Lys Asp Val Ser Ser Thr Ser Asp Asn
        755                 760                 765

Asp Ile Cys Ala Lys Cys Ser Ser Leu Thr Cys Pro Ala Asp Thr Thr
    770                 775                 780

Tyr Arg Thr Tyr Thr Tyr Asp Ser Lys Thr Gly Thr Cys Lys Ala Thr
785                 790                 795                 800

Val Gln Pro Thr Pro Ala Cys Ser Val Cys Glu Ser Gly Lys Phe Val
                805                 810                 815

Glu Lys Cys Lys Asp Gln Lys Leu Glu Arg Lys Val Thr Leu Glu Asn
            820                 825                 830

Gly Lys Glu Tyr Lys Tyr Thr Ile Pro Lys Asp Cys Val Asn Glu Gln
        835                 840                 845

Cys Ile Pro Arg Thr Tyr Ile Asp Cys Leu Gly Asn Asp Asp Asn Phe
    850                 855                 860

Lys Ser Ile Tyr Asn Phe Tyr Leu Pro Cys Gln Ala Tyr Val Thr Ala
865                 870                 875                 880

Thr Tyr His Tyr Ser Ser Leu Phe Asn Leu Thr Ser Tyr Lys Leu His
                885                 890                 895

Leu Pro Gln Ser Glu Glu Phe Met Lys Glu Ala Asp Lys Glu Ala Tyr
            900                 905                 910

Cys Thr Tyr Glu Ile Thr Thr Arg Glu Cys Lys Thr Cys Ser Leu Ile
        915                 920                 925

Glu Thr Arg Glu Lys Val Gln Glu Val Asp Leu Cys Ala Glu Glu Thr
    930                 935                 940

Lys Asn Gly Gly Val Pro Phe Lys Cys Lys Asn Asn Cys Ile Ile
945                 950                 955                 960

Asp Pro Asn Phe Asp Cys Gln Pro Ile Glu Cys Lys Ile Gln Glu Ile
                965                 970                 975

Val Ile Thr Glu Lys Asp Gly Ile Lys Thr Thr Cys Lys Asn Thr
            980                 985                 990

Thr Lys Thr Thr Cys Asp Thr Asn Asn Lys Arg Ile Glu Asp Ala Arg
        995                 1000                1005

Lys Ala Phe Ile Glu Gly Lys Glu Gly Ile Glu Gln Val Glu Cys Ala
    1010                1015                1020

Ser Thr Val Cys Gln Asn Asp Asn Ser Cys Pro Ile Ile Thr Asp Val
1025                1030                1035                1040

Glu Lys Cys Asn Gln Asn Thr Glu Val Asp Tyr Gly Cys Lys Ala Met
                1045                1050                1055

Thr Gly Glu Cys Asp Gly Thr Thr Tyr Leu Cys Lys Phe Val Gln Leu
            1060                1065                1070

Thr Asp Asp Pro Ser Leu Asp Ser Glu His Phe Arg Thr Lys Ser Gly
```

```
            1075                1080                1085
Val Glu Leu Asn Asn Ala Cys Leu Lys Tyr Lys Cys Val Glu Ser Lys
    1090                1095                1100
Gly Ser Asp Gly Lys Ile Thr His Lys Trp Glu Ile Asp Thr Glu Arg
1105                1110                1115                1120
Ser Asn Ala Asn Pro Lys Pro Arg Asn Pro Cys Glu Thr Ala Thr Cys
            1125                1130                1135
Asn Gln Thr Thr Gly Glu Thr Ile Tyr Thr Lys Lys Thr Cys Thr Val
            1140                1145                1150
Ser Glu Glu Phe Pro Thr Ile Thr Pro Asn Gln Gly Arg Cys Phe Tyr
            1155                1160                1165
Cys Gln Cys Ser Tyr Leu Asp Gly Ser Ser Val Leu Thr Met Tyr Gly
            1170                1175                1180
Glu Thr Asp Lys Glu Tyr Tyr Asp Leu Asp Ala Cys Gly Asn Cys Arg
1185                1190                1195                1200
Val Trp Asn Gln Thr Asp Arg Thr Gln Gln Leu Asn Asn His Thr Glu
            1205                1210                1215
Cys Ile Leu Ala Gly Glu Ile Asn Asn Val Gly Ala Ile Ala Ala Ala
            1220                1225                1230
Thr Thr Val Ala Val Val Val Ala Val Val Ala Leu Ile Val
            1235                1240                1245
Val Ser Ile Gly Leu Phe Lys Thr Tyr Gln Leu Val Ser Ser Ala Met
1250                1255                1260
Lys Asn Ala Ile Thr Ile Thr Asn Glu Asn Ala Glu Tyr Val Gly Ala
1265                1270                1275                1280
Asp Asn Glu Ala Thr Asn Ala Ala Thr Phe Asn Gly
            1285                1290
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

TTTGTCACTA TTTTCTAC                                              18

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

TATCTCCATT TGGTTGA                                               17

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

TTTGTCACTA TTTTCTAC                                              18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:10:

CCCAAGCATA TTTGAATG          18